US006235787B1

(12) United States Patent
Broadhurst et al.

(10) Patent No.: US 6,235,787 B1
(45) Date of Patent: May 22, 2001

(54) HYDRAZINE DERIVATIVES

(75) Inventors: Michael John Broadhurst, Royston; William Henry Johnson, Hitchin; Daryl Simon Walter, Knebworth, all of (GB)

(73) Assignee: Hoffmann-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/098,235

(22) Filed: Jun. 16, 1998

(30) Foreign Application Priority Data

Jun. 30, 1997 (GB) ................................. 9713833
Feb. 17, 1998 (GB) ................................. 9803335

(51) Int. Cl.$^7$ .................. A61K 31/15; A61K 31/16; A61K 31/18; C07C 243/26; C07C 311/03
(52) U.S. Cl. .................. 514/614; 514/601; 514/625; 514/837; 514/861; 514/863; 514/885; 514/903; 564/81; 564/95; 564/148; 564/151; 564/154
(58) Field of Search .................. 514/664, 666, 514/837, 861, 863, 885, 903, 601, 614, 625; 564/148, 151, 153, 154, 81, 95

(56) References Cited

U.S. PATENT DOCUMENTS 5,304,549 4/1994 Broadhurst et al. .................. 514/80
5,399,589 3/1995 Rentzea et al. ...................... 514/615

FOREIGN PATENT DOCUMENTS

99/40063 8/1999 (WO).

OTHER PUBLICATIONS

Chernyk et al., "Biologically Active Substances in Hydrazide Derivatives of Succinic Heterylamides", Khimiko–farmatsevticheskii Zhurnal, vol. 23, No. 7, pp. 825–828, Jul. 1989.*
Kratasyuk et al., "The effect of succinic acid sulfoderivatives on bacterial luminescence", Prikl. Biokhim. Mikrobiol., vol. 27(1): 127–133, 1991.*
Makurina et al., "Study of the lyophilic (sic) properties and ionization constants of biologically active sulfahydrazides of dicarboylic acids and their derivatives", Farm. Zh. (Kiev), vol. 5, pp. 55–59, 1985.*
Lauterbach et al., "Pentoxifylline reduces plasma tumour necrosis factor–alpha concentration in premature infants with sepsis", Eur. J. Pediatr., vol. 155: 404–409, 1996.*
Plata–Salaman et al., "Cytokine–induced fever in obese (fa/fa) and lean (Fa/Fa) Zucker rats", Am. J. Physiol. (Regul. Integr. Comp. Physiol. 44), vol. 275: R1353–1357, 1998.*

Bahrami et al., "Significance of TNF in hemorrhage–related hemodynamic alterations, organ injury, and mortality in rats", Am. J. Physiol. (Heart Circ. Physio. 41), vol. 272: H2219–H2226, 1997.*
Carrieri et al., "Profile of Cerebrospinal Fluid and Serum Cytokines in Patients with Relapsing–Remitting Multiple Sclerosis: A Correlation with Clinical Activity", Immunopharmacology and Immunotoxicology, vol. 20(3): 373–382, 1998.*
Chem. Abstract vol. 104, No. 9 (Mar. 3, 1986), Abstract No. 61519.
Chemical Abstr., General Substances Index, vol. 11$^{th}$ Collective, 1982–1986, p. 14, 583 CS, Compound with RN 87362–025 which is 2–(phenylsulfonyl)hydrazide.
Coffrey, R. J. et al., Nature (1987) 328, pp. 817–820.
Karashima, T. et al., Dermatol. Sci. (1996) 12, pp. 246–254.
Olanrian A. et al., Arch. Dermatol. Res. (1995) 287, pp. 231–236.

* cited by examiner

Primary Examiner—Howard C. Lee
(74) Attorney, Agent, or Firm—George W. Johnston; Dennis P. Tramaloni

(57) ABSTRACT

Hydrazine derivatives of the formula

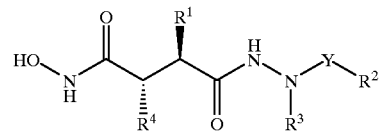

(I)

wherein Y is CO or $SO_2$; $R^1$ is lower alkyl, lower alkenyl, lower cycloalkyl, lower cycloalkyl-lower alkyl, aryl or aryl-lower alkyl; $R^2$ is lower alkyl, halo-lower alkyl, aryl-lower alkyl, aryl-lower alkenyl or aryl when Y is $SO_2$ and is lower alkyl, halo-lower alkyl, lower alkoxy, lower alkoxycarbonyl, acyl, lower cycloalkyl, aryl, aryl-lower alkyl, aryl-lower alkoxy or $NR^5R^6$ when Y is CO; and $R^3$ is hydrogen, lower alkyl optionally substituted by cyano, amino, hydroxy, lower alkoxy, lower alkoxycarbonyl, heterocyclyl or heterocyclylcarbonyl, lower alkenyl, lower alkynyl, lower cycloalkyl, lower cycloalkyl-lower alkyl, aryl-lower alkyl, aryl-lower alkenyl, aryl or heterocyclyl; or $R^2$ and $R^3$ together form the residue of a 5-, 6- or 7-membered cyclic amide, cyclic imide, cyclic sulphonamide or cyclic urethane group; $R^4$ is lower alkyl, hydroxy-lower alkyl, lower alkenyl, lower cycloalkyl, lower cycloalkyl-lower alkyl or a group of the formula X-aryl, X-heteroaryl or —$(CH_2)_{1-2}$—CH=$CR^7R^8$; X is a spacer group; $R^5$ and $R^6$ each individually are hydrogen, lower alkyl or aryl-lower alkyl; and $R^7$ and $R^8$ together represent a lower alkylene group in which one methylene group is optionally replaced by a hetero atom; and their pharmaceutically acceptable salts inhibit not only the release of tumour necrosis factor (TNF-α) and transforming growth factor (TGF-α) from cells, but also keratinocyte proliferation. They are useful as medicaments, especially for the treatment of inflammation, fever, hemorrhage, sepsis, rheumatoid arthritis, osteoarthritis, multiple sclerosis or psoriasis.

28 Claims, No Drawings

HYDRAZINE DERIVATIVES

BACKGROUND OF THE INVENTION

Release of such cytokines as tumor necrosis factor α(TNF-α) and transforming growth factor α(TGF-α) can cause adverse reactions ranging from fever to sepsis. Many of these reactions are related to inflammation or autoinmuune conditions, such as psoriasis and arthritis.

Hydroxamic acid derivatives are known to have some inhibitory effect against the release of certain cytokines, however they also inhibit matrix metalloproteinase enzymes (MMPs) such as collagenases, stromolysins, and gelatinases, leading to undesirable side effects. Thus it is desirable to find compounds capable of inhibiting TNF-α and TGF-α release which do not have these side effects. It has been discovered that, in contrast to structurally related hydroxamic acid derivatives, the hydrazine derivatives provided by the present invention show only weak inhibitory activity against the matrix metalloproteinase (MMP) family of enzymes, such as collagenases, stromelysins and gelatinases.

SUMMARY OF THE INVENTION

The novel hydrazine derivatives provided by the present invention are compounds of the general formula:

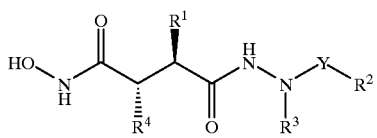

(I)

wherein

Y is CO or $SO_2$;

$R^1$ is lower alkyl, lower alkenyl, lower cycloalkyl, lower cycloalkyl-lower alkyl, aryl or aryl-lower alkyl;

$R^2$ is lower alkyl, halo-lower alkyl, aryl-lower alky, aryl-lower alkenyl or aryl when Y is $SO_2$ and is lower alkyl, halo-lower alkyl, lower alkoxy, lower alkoxycarbonyl, acyl, lower cycloalkyl, aryl, aryl-lower alky, aryl-lower alkoxy or $NR^5R^6$ when Y is CO; and $R^3$ is hydrogen, lower alkyl optionally substituted by cyano, amino, hydroxy, lower alkoxy, lower alkoxycarbonyl, heterocyclyl or heterocyclylcarbonyl, lower alkenyl, lower alkynyl, lower cycloalkyl, lower cycloalkyl-lower alkyl, aryl-lower alkyl, aryl-lower alkenyl, aryl or heterocyclyl; or $R^2$ and $R^3$ together form the residue of a 5-, 6- or 7-membered cyclic amide, cyclic imide, cyclic sulphonamide or cyclic urethane group;

$R^4$ is lower alkyl, lower alkenyl, lower cycloalkyl, lower cycloalkyl-lower alkyl or a group of the formula X-aryl, X-heteroaryl or $—(CH_2)_{1-2}—CH=CR^7R^8$;

X is a spacer group;

$R^5$ and $R^6$ each individually are hydrogen, lower alkyl or aryl-lower alkyl; and $R^7$ and $R^8$ together represent a lower alkylene group in which one methylene group is optionally replaced by a hetero atom;

and pharmaceutically acceptable salts thereof.

The hydrazine derivatives provided by the present invention are inhibitors of TNF-α and TGF-α release from cells. They also inhibit the proliferation of keratinocytes.

Accordingly, the present hydrazine derivatives can be used as medicaments for the treatment of conditions related to release of these cytokines, especially in inflammation, fever, haemorrhage, sepsis, rheumatoid arthritis, osteoarthritis, multiple sclerosis and psoriasis.

DETAILED DESCRIPTION OF THE INVENTION

As used herein, the term "lower alkyl", alone or in combination as in e.g. "halo-lower alkyl" and "lower cycloalkyl-lower alkyl", means a straight-chain or branched-chain alkyl group containing up to 7, preferably up to 4, carbon atoms, e.g. methyl, ethyl, n-propyl, isopropyl, n-butyl, isobutyl, sec.butyl, tert-butyl, n-pentyl and n-hexyl. Trifluoromethyl is an example of a halo-lower alkyl group. The term "lower alkoxy", alone or in combination as in "lower alkoxycarbonyl", means a lower alkyl group as defined above which is bonded via an oxygen atom, e.g. methoxy, ethoxy, n-propoxy, isopropoxy, n-butoxy, isobutoxy and tert-butoxy. Methoxycarbonyl, ethoxycarbonyl and the like are examples of lower alkoxycarbonyl groups.

The term "lower cycloalkyl", alone or in combination as in "lower cycloalkyl-lower alkyl", means a cycloalkyl group containing 3 to 7 carbon atoms, i.e. cyclopropyl, cyclobutyl, cyclopentyl, cyclohexyl and cycloheptyl. Cyclopropylmethyl, 2-cyclobutyl-ethyl and 3-cyclohexyl-propyl are examples of lower cycloalkyl-lower alkyl groups.

The term "lower alkenyl", alone or in combination as in "aryl-lower alkenyl", means an alkenyl group containing from 2 to 7 carbon atoms, e.g. allyl, vinyl and butenyl, and the term "lower alkynyl" means an alkynyl group containing from 2 to 7 carbon atoms, e.g. propargyl or butynyl.

The term "lower alkylene" means an alkylene group containing from 2 to 6 carbon atoms, e.g. dimethylene, trimethylene, tetramethylene etc. Thus, $R^7$ and $R^8$ together with the carbon atom to which they are attached can represent, for example, a cyclopentane, cyclohexane or tetrahydropyranyl ring.

The term "acyl" denotes an acyl group derived from a lower alkanecarboxylic acid, i.e. an alkanecarboxylic acid containing up to 6 carbon atoms, or from an aromatic carboxylic acid. Examples of such acyl groups are acetyl, propionyl, butyryl, isobutyryl, pivaloyl, benzoyl, p-chlorobenzoyl, and the like.

The term "aryl" means phenyl or naphthyl optionally substituted by halogen, i.e. fluorine, chlorine, bromine or iodine, lower alkyl, lower alkoxy, trifluoromethyl, hydroxy, lower alkoxycarbonyl, nitro, phenyl or the like, e.g. phenyl, 1-naphthyl, 2-methylphenyl, 4-methoxyphenyl, 2,4-difluorophenyl, 4-nitrophenyl and 4-methoxycarbonylphenyl. Benzyl, 4-chlorobenzyl, 4-bromobenzyl, 3-hydroxybenzyl, 4-methoxybenzyl, 4-nitrobenzyl, 2-phenylethyl, 3,4-dimethoxy-phenethyl and the like are typical examples of aryl-lower alkyl groups and benzyloxy, 4-chlorobenzyloxy and 4-nitro-benzyloxy are typical examples of aryl-lower alkoxy groups. 2-Phenylvinyl and 3-phenylallyl can be mentioned as examples of aryl-lower alkenyl groups.

The term "heterocyclyl" means a 4-, 5- or 6-membered saturated or partially unsaturated or 5- or 6-membered aromatic heterocyclic group which is bonded via a C atom or secondary N atom (i.e. —NH—), which contains one or more hetero atoms selected from nitrogen, sulphur and oxygen and which is optionally substituted by e.g. halogen, lower alkyl, lower alkoxy and/or oxo and/or optionally benz-fused. Examples of heterocyclyl groups are pyrrolidinyl, pyrrolinyl, pyrazolinyl, piperidinyl, morpholinyl, thiamorpholinyl, tetrahydropyranyl, tetrahydrothiopyranyl, furyl, thienyl, thiazolyl, oxazolyl, isoxazolyl, oxetanyl, imidazolidinyl, dioxolanyl, pyrrolyl, pyridyl, pyrimidinyl, benzofuranyl, benzothienyl, benzthiazolyl, indolyl, isoindolyl, e.g. phthalimido, quinolyl and isoquinolyl.

The term "heterocyclylcarbonyl" means a heterocyclyl group as previously defined which is bonded to C(O) via a secondary N atom. Morpholinocarbonyl is a typical example of such a heterocyclylcarbonyl group.

The term "heteroaryl" means an aromatic heterocyclic group within the definition of "heterocyclyl".

The cyclic amide, imide, sulphonamide or urethane group formed by $R^2$, $R^3$ and the atoms to which they are attached, i.e. the C or S atom of Y and, respectively, the N atom, can be, for example, a group of formulae (a)–(g) hereinafter in which n stands for 3, 4 or 5 and $R^a$ and $R^b$ together form the reminder of an aromatic or cycloalkane ring:

(a)
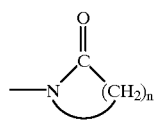

(b)
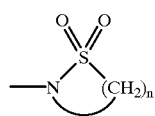

(c)
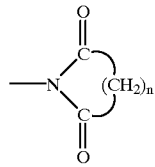

(d)
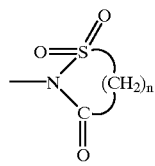

(e)
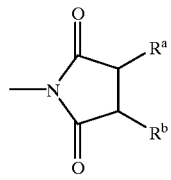

(f)
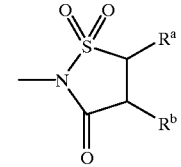

(g)
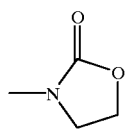

Preferred spacer groups denoted by X are groups of the formulae —$(CH_2)_{1-5}$—, —$CH_2$—CH=CH—, —$CH_2$—C≡C—, —$CH_2NHCO$—, —$(CH_2)_1$ or $_2NHCONH$—, —$(CH_2)_{1-5}$—S—, especially —$CH_2S$—, —$CH_2NHSO_2$—, —$CH_2NHCH_2$—, —$(CH_2)_{1-5}$—O—, —O—$(CH_2)_{1-5}$— and —S—.

The compounds of formula I form pharmaceutically acceptable salts with bases such as alkali metal hydroxides, e.g. sodium hydroxide and potassium hydroxide, alkaline earth metal hydroxides, e.g. calcium hydroxide, barium hydroxide and magnesium hydroxide, and the like. Those compounds of formula I which are basic can form pharmaceutically acceptable salts with inorganic acids, e.g. with hydrohalic acids such as hydrochloric acid and hydrobromic acid, sulphuric acid, nitric acid and phosphoric acid, and with organic acids, e.g. with acetic acid, tartaric acid, succinic acid, fumaric acid, maleic acid, malic acid, salicylic acid, citric acid methanesulphonic acid and p-toluenesulphonic acid. Such salts are part of this invention. Thus each compound described below includes its pharmaceutically acceptable salt.

It will be appreciated that, although the formulae presented herein show the respective compounds in their absolute stereochemistry, the invention embraces not only the depicted stereo-isomers, but also the corresponding racemates and diastereoisomeric mixtures. Further, when the spacer group denoted by X contains an olefinic double bond, as in —$CH_2$—CH=CH—, this can have the (E) or (Z) configuration, preferably the (E) configuration.

Compounds of formula I where $R^1$ is lower alkyl, especially isobutyl, or where $R^2$ is lower alkyl, especially methyl, or where $R^3$ is lower alkyl, lower alkenyl, aryl-lower alkyl or aryl, especially isobutyl, 2-methylbutyl, 2-methylallyl, unsubstituted benzyl or unsubstituted phenyl, or where $R^4$ is X-aryl especially X-phenyl, or where X is —$(CH_2)_{1-5}$—, —$CH_2$—CH=CH—, —$CH_2$—C≡C—, —$CH_2NHCO$—, —$(CH_2)_1$ or $_2NHCONH$—, —$(CH_2)_{1-5}$—S—, —, —$CH_2NHSO_2$—, —$CH_2NHCH_2$—, —$(CH_2)_{1-5}$—O—, —O—$(CH_2)_{1-5}$— and —S—, especially —$CH_2S$—, —$(CH_2)_{1-5}$—, —$CH_2$—CH=CH—, —$CH_2$—C≡C—, —$CH_2NHCO$—, —$(CH_2)_1$ or $_2NHCONH$, —$(CH_2)_{1-5}$—S—, and —$CH_2NHSO_2$, are part of this invention. So is any such compound in which at least two or more of these conditions are met, especially where $R^4$ is X-phenyl and X is —$CH_2$—CH=CH—.

Preferred compounds of this invention are compounds of formula I where Y is CO or $SO_2$; $R^1$ is lower alkyl, lower cycloalkyl, lower cycloalkyl-lower alkyl, aryl or aryl-lower alkyl; $R^2$ is lower alkyl, aryl-lower alkyl or aryl when Y is $SO_2$ and is lower alkyl, lower alkoxy, lower cycloalkyl, aryl-lower alkoxy or $NR^5R^6$ when Y is CO; and $R^3$ is hydrogen, lower alkyl optionally substituted by cyano or amino, lower alkenyl, lower alkynyl, lower cycloalkyl, lower cycloalkyl-lower alkyl, aryl-lower alkyl, aryl or heterocyclyl; or $R^2$ and $R^3$ together form the residue of a 5-, 6- or 7-membered cyclic amide, cyclic imide or cyclic sulphonamide group; $R^4$ is a group of the formula X-aryl or X-heteroaryl; X is a spacer group; heteroaryl is C-bonded; and $R^5$ and $R^6$ each individually are hydrogen, lower alkyl or aryl-lower alkyl. In any such compound, $R^1$ may be lower alkyl (especially isobutyl), or $R^2$ may be lower alkoxy (especially methoxy) when Y is CO, $R^2$ may be lower alkyl (especially methyl) when Y is $SO_2$, or $R^3$ may be lower alkyl, lower alkenyl, aryl-lower alkyl or aryl (especially isobutyl, 2-methylbutyl, 2-methylallyl, unsubstituted benzyl or unsubstituted phenyl), or $R^4$ may be X-aryl (especially X-phenyl), or X may be —$(CH_2)_{1-5}$—, —$CH_2$—CH=CH—, —$CH_2C \equiv C$—, —$CH_2NHCO$—, —$(CH_2)_1$ or $_2NHCONH$—, —$(CH_2)_{1-5}$—S—, —$CH_2NHSO_2$—, —$CH_2NHCH_2$—, —$(CH_2)_{1-5}$—O—, —O—$(CH_2)_{1-5}$— or —S—, especially —$(CH_2)_{1-5}$—, —$CH_2$—CH=CH—, —$CH_2$—$C \equiv C$—, —$CH_2NHCO$—, —$(CH_2)_1$ or $_2NHCONH$—, —$CH_2S$—, —$CH_2NHSO_2$— or —$CH_2NHCH_2$—, and particularly —$CH_2$—CH=CH—, or R4 may be X-phenyl where X is —$CH_2$—CH=CH—. Any such compound as described in this paragraph in which at least one and preferably two or more of these conditions are met, is contemplated by this invention.

Other preferred compounds of formula I are those in which Y is CO and $R^2$ is lower alkoxy, especially methoxy, or where Y is $SO_2$ and $R^2$ is lower alkyl, especially methyl. In either compound, $R^1$ preferably is lower alkyl, especially isobutyl. $R^3$ preferably is lower alkyl, especially isobutyl or 2-methylbutyl, lower alkenyl, especially 2-methylallyl, aryl-lower alkyl, especially unsubstituted benzyl, or aryl, especially unsubstituted phenyl. $R^4$ preferably is a group of the formula X-aryl such as phenyl, especially when X is a spacer group of the formula —$(CH_2)_{1-5}$—; —$CH_2$—CH=CH—, —$CH_2$—$C \equiv C$—, —$CH_2NHCO$—, —$(CH_2)_1$ or $_2NHCONH$—, —$(CH_2)_{1-5}$—S—, —$CH_2NHSO_2$—, —$CH_2NHCH_2$—, —$(CH_2)_{1-5}$—O—, —O—$(CH_2)_{1-5}$— or —S—, especially —$CH_2$—CH=CH—.

Particularly preferred compounds of formula I are:

(E)-2(R)-[1(S)-(Hydroxyarbamoyl)-4-phenyl-3-butenyl]-2'-isobutyl-2'-(methanesulphonyl)-4-methylvalerohydrazide;

(E)-2(R)-[1(S)-(hydroxycarbamoyl)-4-phenyl-3-butenyl]-2'-(methanesulphonyl)-4-methyl-2'-phenylvalerohydrazide;

(E)-2(R)-[1(S)-(hydroxycarbamoyl)-4-phenyl-3-butenyl]-2'-(methanesulphonyl)-4-methyl-2'-(2(S)-methylbutyl)valerohydrazide;

(E)-2(R)-[1(S)-(hydroxycarbamoyl)-4-phenyl-3-butenyl]-2'-(methanesulphonyl)-4-methyl-2'-(2-methylallyl)valerohydrazide; and methyl (E)-3-[2(R)-[1(S)-(hydroxycarbamoyl)-4-phenyl-3-butenyl]-4-methylvaleryl]-2-isobutylcarbazate.

According to the process provided by the present invention, the novel hydrazine derivatives defined earlier are manufactured by cleaving off the protecting group denoted by $R^9$ from a compound of the general formula:

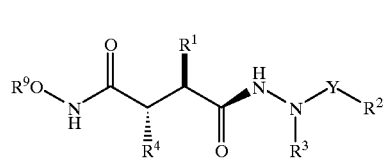

(II)

wherein Y, $R^1$, $R^2$, $R^3$ and $R^4$ have the significance given earlier and $R^9$ is a protecting group, and, if desired, converting a compound of formula I obtained into a pharmaceutically acceptable salt.

The protecting group denoted by $R^9$ in a compound of formula II can be any conventional protecting group, but is preferably tetrahydropyranyl, 4-methoxybenzyl, benzyl or tri(lower alkyl)silyl, especially tert-butyldimethylsilyl.

The cleavage of the protecting group denoted by $R^9$ from a compound of formula II is carried out according to methods known per se. For example, the tetrahydropyranyl group can be cleaved off by treatment with a sulphonic acid, e.g. methanesulphonic acid or p-toluenesulphonic acid, in a lower alkanol, e.g. methanol. Cleavage of the 4-methoxybenzyl group can be effected, for example, using trifluoroacetic acid. Hydrogenolysis in the presence of a catalyst, e.g. palladium, and in a lower alkanol, e.g. methanol, can be used for the cleavage of the benzyl protecting group. A tri(lower alkyl)silyl protecting groupcan be cleaved off using water or low pH; with this cleavage typically taking place during the working up of the respective compound of formula II from the medium in which it is prepared (i.e. the cleavage takes place in situ).

The conversion of compounds of formula I obtained into pharmaceutically acceptable salts is effected by treatment with an appropriate acid or base in a known manner.

The compounds of formula II used as starting materials in the foregoing process are novel and form a further object of the present invention. They can be prepared by various routes as illustrated in the following Reaction Schemes in which Y, $R^1$, $R^2$, $R^3$, $R^4$ and $R^9$ have the significances given earlier, $^tBu$ is tert-butyl and Me is methyl.

Reaction Scheme A

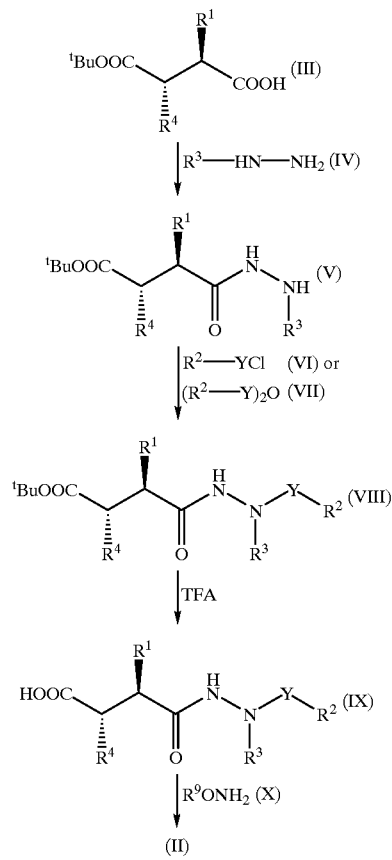

Having regard to Reaction Scheme A, in the first step a compound of formula III is condensed with hydrazine or a substituted hydrazine of formula IV to give a hydrazide of formula V. This condensation is carried out under the known conditions of peptide coupling reactions and using the coupling reagents known per se for such couplings, e.g. 1-hydroxybenzotriazole in the presence of 1-ethyl-3-(3-dimethylaminopropyl)carbodiimide hydrochloride.

A hydrazide of formula V is then reacted either with a chloride of formula VI or with an anhydride of formula VII to give a compound of formula VIII. This reaction is carried out in a known manner, e.g. in an organic solvent which is inert under the conditions of the reaction and in the presence of an organic base at about 0° C. to about room temperature. Suitable solvents are halogenated hydrocarbons, e.g. dichloromethane. Examples of organic bases which can be used are tri(lower alkyl)-amines, e.g. triethylamine, pyridine, 4-dimethylaminopyridine and the like. When the base is liquid under the reaction conditions it may be used in excess and in this case it can serve as the sole solvent.

Subsequently, in the next step a compound of formula VIII is deprotected with trifluoroacetic acid (TFA) to give a carboxylic acid of formula IX. This deprotection is carried out in a manner known per se, e.g. in an organic solvent which is inert under the conditions of the reaction, such as a halogenated hydrocarbon, e.g. dichloromethane, at about room temperature.

Finally, a carboxylic acid of formula IX is converted into a starting material of formula II by condensation with an O-protected hydroxylamine of formula X. This condensation is carried out in a manner known per se for peptide coupling reactions and using conventional coupling reagents, e.g. 1-hydroxybenzotriazole in the presence of 1-ethyl-3-(3-dimethylaminopropyl)carbodiimide hydrochloride.

If desired, compounds occurring in or prepared by Reaction Scheme A can be interconverted or substituted.

Thus, a compound of formula V in which $R^3$ represents hydrogen can be converted into a corresponding compound of formula V in which $R^3$ represents lower alkyl, lower alkenyl, lower alkynyl, lower cycloalkyl or aryl-lower alkyl in a manner known per se. For example, a compound of formula V in which $R^3$ represents hydrogen can be condensed with an aldehyde of the general formula $R^{30}$-CHO, wherein $R^{30}$ is lower alkyl, lower alkenyl, lower alkynyl, lower cycloalkyl, aryl-lower alkyl or aryl, e.g. in the presence of p-toluenesulphonic acid and molecular sieves, and the resulting substituted imine can be reduced, preferably in situ, using an alkali metal cyanoborohydride, especially sodium cyanoborohydride. Alternatively, a compound of formula V in which $R^3$ represents hydrogen can be reacted with a cyclic anhydride of the general formula:

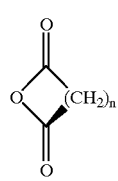

(XI)

wherein n has the significance given earlier, e.g. glutaric anhydride, conveniently in the presence of an organic base, e.g. a tri(lower alkyl)amine such as triethylamine, and in an organic solvent which is inert under the conditions of the reaction, e.g. an aromatic hydrocarbon such as benzene, toluene etc., at an elevated temperature, suitably at the reflux temperature of the reaction mixture. There is thus obtained a compound of formula VIII in which $R^2$, $R^3$ and the atoms to which they are attached together are a group of formula (c) hereinbefore.

A compound of formula II in which $R^3$ represents hydrogen can be converted into a corresponding compound of formula II in which $R^{30}$ has the significance given earlier by reaction with a known compound of the general formula $R^{30}$-X, wherein $R^{30}$ has the significance given earlier and X represents halogen, conveniently in the presence of a base, e.g. an alkali metal carbonate such as sodium carbonate or potassium carbonate, and in an organic solvent which is inert under the conditions of the reaction, e.g. dimethylformamide.

Further, a compound of formula VIII in which $R^4$ represents phthalimido-lower alkyl can be treated with hydrazine hydrate, conveniently in an organic solvent which is inert under the conditions of the reaction, e.g. a lower alkanol such as methanol or ethanol, at about room temperature, and the resulting product, a compound corresponding to formula VIII, but in which $R^4$ represents amino-lower alkyl, can be reacted with an appropriate (hetero)aromatic carboxylic acid or sulphonic acid halide, (hetero)aromatic isocyanate or (hetero)aromatic carboxylic acid in the presence of a coupling reagent in the presence of a base to introduce a desired group $R^4$.

The carboxylic acids of formula IX in Reaction Scheme A are novel and form a further object of the present invention.

The compounds of formulae III used in Reaction Scheme A, insofar as they are not known compounds or analogues of known compounds, can be prepared as described in the following Examples or in analogy thereto. Moreover, the compounds of formulae IV, VI, VII and X also used in Reaction Scheme A as well as the aldehydes of formula $R^{30}$-CHO and the cyclic anhydrides of formula XI are known compounds or analogues of known compounds.

Reaction Scheme B

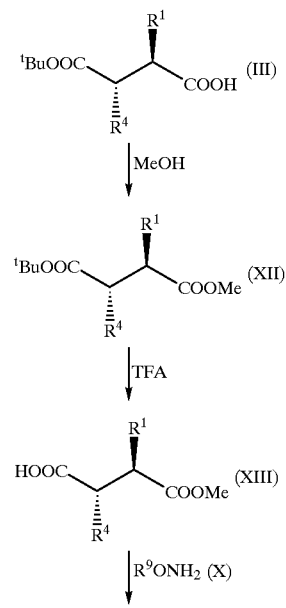

-continued

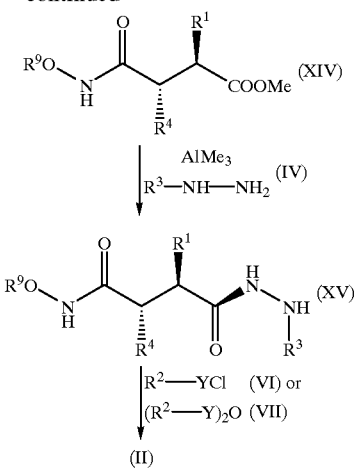

(II)

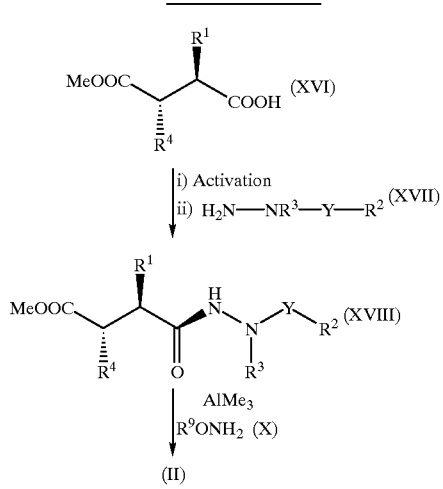

Having regard to reaction Scheme B, the first step comprises the conversion of a carboxylic acid of formula III into a corresponding methyl ester of formula XII. This is effected in a known manner, e.g. by reaction with methanol in the presence of a tertiary organic base such as 4-dimethylaminopyridine and a condensation agent, e.g. a diimide such as 1-ethyl-3-(3-dimethylaminopropyl)-carbodiimide.

Then, the methyl ester of formula XII is deprotected at the tert-butoxycarbonyl group by treatment with trifluoroacetic acid. This deprotection is carried out in a manner known per se, e.g. in an organic solvent which is inert under the conditions of the reaction, such as a halogenated hydrocarbon, e.g. dichloromethane, at about room temperature.

The resulting compound of formula XIII is subsequently condensed with an O-protected hydroxylamine of formula X to give a compound of formula XIV. This condensation is performed in a manner known per se for peptide coupling reactions and using conventional coupling reagents, e.g. 1-hydroxybenzotriazole in the presence of 1-ethyl-3-(3-dimethylaminopropyl)carbodiimide hydrochloride.

In the next step a compound of formula XIV is reacted with trimethylaluminium and hydrazine or a substituted hydrazine of formula IV to give a compound of formula XV. This reaction is conveniently carried out in an organic solvent which is inert under the reaction conditions, e.g. a halogenated hydrocarbon such as dichloromethane, and at a temperature in the approximate range of room temperature to 60° C.

Finally, the desired starting material of formula II is obtained by reacting a compound of formula XV with a chloride of formula VI or an anhydride of formula VII. This reaction is carried out in a known manner, e.g. in an organic solvent which is inert under the conditions of the reaction and in the presence of an organic base at about 0° C. to about room temperature. Suitable solvents are halogenated hydrocarbons, e.g. dichloromethane. Examples of organic bases which can be used are tri(lower alkyl)amines, e.g. triethylamine, pyridine, 4-dimethylaminopyridine and the like. When the base is liquid under the reaction conditions it may be used in excess and in this case it can simultaneously serve as the solvent.

In the first step of Reaction Scheme C a carboxylic acid of formula XVI is activated, e.g. by treatment with oxalyl chloride, and then reacted with a substituted hydrazine of formula XVII to give a compound of formula XVIII. This reaction is conveniently carried out in the presence of a base, especially a tertiary organic amine such as triethylamine, and in an organic solvent which is inert under the reaction conditions, e.g. a halogenated hydrocarbon such as dichloromethane, at about 0° C.

Subsequently, a compound of formula XVIII is converted into a desired starting material of formula II by reaction with trimethylaluminium and an O-protected hydroxylamine of formula X. This reaction is conveniently carried out in an organic solvent which is inert under the reaction conditions, e.g. a halogenated hydrocarbon such as dichloromethane, and at a temperature of about room temperature to about 60° C.

The carboxylic acids of formula XVI and the substituted hydrazines of formula XVII used in Reaction Scheme C are known compounds or analogues of known compounds which can be prepared in a manner analogous to the known compounds.

As mentioned earlier, the hydrazine derivatives provided by the present invention inhibit the release of TNF-α and TGF-α as well as the proliferation of keratinocytes. These activities can be demonstrated using the in vitro tests described hereinafter. Thus any compound of formula I which is active to inhibit release of TNF-α and/or TGF-α and/or the proliferation of keratinocytes is a compound of this invention. Assays to measure these three indicators of pharmacological activity are known in the art. Examples of such assays are also provided below.

Test A: Inhibition of TNF-α Release

THP1 cells were cultivated in RPMI 1640 medium supplemented with antibiotics and 10% foetal calf serum, harvested by centrifugation and diluted to $5 \times 10^5$ cells/ml in the above medium supplemented with 20 mM HEPES buffer. Aliquots (200 ml) of the cell suspension were plated out on 96 well culture plates and incubated for 0.5 hour at 37° C. prior to the addition of the test compounds. The latter were dissolved in dimethyl sulphoxide (DMSO) to a stock concentration of 1.2 mM which was diluted with phosphate buffered saline/10% DMSO solution to provide test compounds in final concentrations of $10^{-9}$ to $10^{-5}$ M, with each concentration being tested in duplicate. The cells were incubated with the test compounds for 0.5 hour at 37° C., LPS (bacterial lipopolysaccharide) was then added to a concentration of 2 mg/mg and incubation was continued for 3 hours at 37° C. in an atmosphere containing 5% $CO_2$ and at 95% relative humidity. After centrifugation at 260 g for 10 minutes an aliquot of each supernatant was removed and the amount of TNF-a was estimated by ELISA (R & D Systems Europe Ltd., Abingdon, England). The concentration of test compound which brings about 50% inhibition of LPS-induced TNF-a release ($IC_{50}$) was computed from the dose-response curve.

Test B: Inhibition of TGF-α Release

This test is an adaptation of the method described by R. J. Coffrey, R. Derynk, J. N. Wilcox, T. S. Bringman, A. S. Goustin, H. L. Moses and M. R. Pittelkow, Nature, (1987), 328, 816–820. Normal human epidermal keratinocytes (NHEK) (neonatal and adult) were supplied by Clonetics Corporation, San Diego, Calif., USA and at the third passage were plated out on 96 well culture plates at $2\times10^3$ to $10^4$ cells per well and grown in a humidified incubator having a 5% $CO_2$ atmosphere at 37° C. for 5 days in serum-free keratocyte growth medium (KGM; Clonetics Corporation). Test compounds were dissolved in DMSO and then diluted 10 times in keratinocyte basal medium (KBM; Clonetics Corporation). Serial dilutions of the test compounds were made in 10% DMSO in KBM to provide concentrations 12 times higher than the final assay concentration. The test compound dilutions (or vehicle only as controls) were added to the cells and incubation was then carried out at 37° C. for 0.5 hour. TGF-a release was then stimulated by the addition of 10 ng/ml TPA (phorbol 12-myristate 13-acetate). After further incubation at 37° C. for 24 hours the TGF-a content of the culture medium was carried out either by TGF-a ELISA (Oncogene Science Inc., Uniondale, N.Y., USA) or by an electrochemiluminescence-based detection system (Igen Inc., Gaithersburg, Md., USA) formatted with anti-human TGF-a (R & D Systems Europe Ltd.). The concentration of test compound which inhibited the release of TGF-a by 50% relative to the control ($IC_{50}$ nMol) was then calculated.

Test C: Inhibition of Keratinocyte Proliferation

This test is an adaptation the methods described by T. Karashima, H. Hachisuka and Y. Sasai, J. Dermatol. Sci., (1996), 12, 246–254 and A. Olaniran, B. S. Baker, J. J. Garioch, A. V. Powles and L. Fry, Arch. Dermatol. Res., (1995), 287, 231–236. Normal human epidermal kerati-nocytes (NHEK) (neonatal and adult) were plated out on 96 well culture plates at $2\times10^3$ cells per well. Following attachment of the cells to the plate by incubation for 24 hours in a humidified incubator having a 5% $CO_2$ atmosphere at 37° C. in serum-free KGM (see above), the medium was replaced with KBM (see above) for 4 days in order to arrest the growth of the cells. Test compounds were dissolved in DMSO and then diluted 10 times in KBM. Serial dilutions of the test compounds were made in 10% DMSO in KBM to provide concentrations 11 times higher than the final assay concentration. The cells were then returned to KGM and the test compound dilutions (or vehicle only for controls) were added immediately. After incubation for 3 days the cells were pulsed with 1 mCi/well $^3$H-thymidine, specific activity 5 Ci/mmol (Amersham International plc, Little Chalfont, Buckinghamshire, UK), for the last 16 hours. Cells were then detached using trypsin-EDTA and harvested. $^3$H-Thymidine incorporation as a measure of proliferation was determined by scintillation counting techniques. The concentration of test compound which inhibited $^3$H-thymidine incorporation by 50% relative to the control ($IC_{50}$ nMol) was calculated.

The results obtained in the foregoing tests with representative compounds of formula I are compiled in the following Table.

TABLE

| Compound | Test A $IC_{50}$ (nMol) | Test B $IC_{50}$ (nMol) | Test C $IC_{50}$ (nMol) |
| --- | --- | --- | --- |
| A | 437 | 210 | 1300 |
| B | 515 | 255 | 1100 |
| C | 365 | N/T | N/T |
| D | 408 | N/T | N/T |
| E | 531 | N/T | N/T |
| F | 1516 | N/T | N/T |
| G | 428 | N/T | N/T |
| H | 381 | N/T | N/T |
| I | 881 | N/T | N/T |
| J | 933 | N/T | N/T |

N/T Not tested.
A = (E)-2(R)-[1(S)-(Hydroxycarbamoyl)-4-phenyl-3-butenyl]-2'-(methanesulphonyl)-4-methyl-2'-phenylvalerohydrazide.
B = (E)-2(R)-[1(S)-Hydroxycabamoyl)-4-phenyl-3-butyl]-2'-(methanesulphonyl)-2'-(4-methoxyphenyl)-4-methylvalerohydrazide.
C = (E)-2'-Benzyl-2(R)-[1(S)-(hydroxycarbamoyl)-4-phenyl-3-butenyl]-2'-(methanesulphonyl)-4-methylvalerohydrazide.
D = (E)-2'-(Cyclohexylmethyl)-2(R)-[1(S)-(hydroxycarbamoyl)-4-phenyl-3-butenyl]-2'-(methanesulphonyl)-4-methylvalerohydrazide.
E = (E)-2(R)-[1(S)-(Hydroxycarbamoyl)-4-phenyl-3-butenyl]-2'-isobutyl-2'-(methanesulphonyl)-4-methylvalerohydrazide.
F = (E)-2(R)-[(1S)-(Hydroxycarbamoyl)-4-phenyl-3-butenyl]-4-methyl-N-(2,6-dioxopiperidino)valeramide.
G = (E)-2(R)-[1(S)-(hydroxycarbamoyl)-4-phenyl-3-butenyl]-2'-(methanesulphonyl)-4-methyl-2'-[2(S)-methylbutyl]valerohydrazide.
H = (E)-2(R)-[1(S)-(hydroxycarbamoyl-4-phenyl-3-butenyl]-2'-(methanesulphonyl)-4-methyl-2'-(2-methylallyl)valerohydrazide.
I = Methyl (E)-3-[2(R)-[1(S)-(hydroxycarbamoyl)-4-phenyl-3-butenyl]-4-methylvaleryl]-2-isobutylcarbazate.
J = (E)-2(R)-[(S)-(Hydroxycarbamoyl)-4-phenyl-3-butenyl]-2'-(isobutyl)-2'-(isopentanoyl)-4-methylvalerohydrazide.

The hydrazine derivatives provided by the present invention can be used as medicaments, for example in the form of pharmaceutical compositions. Such a pharmaceutical composition which comprises a compound of formula I and a therapeutically inert carrier material. The pharmaceutical compositions can be administered orally, e.g. in the form of tablets, coated tablets, dragees, hard and soft gelatine capsules, solutions, emulsions or suspensions. However, they can also be administered rectally, e.g. in the form of suppositories, or parenterally, e.g. in the form of injection solutions.

For the manufacture of pharmaceutical compositions the hydrazine derivatives can be formulated with therapeutically inert, inorganic or organic carriers. Lactose, corn starch or derivatives thereof, talc, stearic acid or its salts can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active ingredient no carriers are, however, generally required in the case of soft gelatine capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerine, vegetable oils and the like. Natural and hardened oils, waxes, fats, semi-liquid polyols and the like are suitable carriers for the manufacture of suppositories. The pharmaceutical compositions can also contain preservatives, stabilizers, wetting agents, emulsifiers, sweeteners, colorants, flavorants, salts for adjustment of the osmotic pressure buffers coating agents or antioxidants.

Medicaments containing an aforementioned hydrazine derivative and a therapeutically acceptable carrier as well as a process for the manufacture of such medicaments are also objects of the present invention. This process comprises bringing a compound of formula I or a pharmaceutically acceptable salt thereof into a galenical administration form together with a therapeutically inert carrier material and, if desired, one or more additional therapeutically active substances.

A further object of the invention comprises the use of the hydrazine derivatives provided by the invention in the treatment of illnesses, especially in the treatment of inflammation, fever, haemorrhage, sepsis, rheumatoid arthritis, osteoarthritis, multiple sclerosis and psoriasis. The dosage can vary within wide limits and will, of course, be adjusted to the individual requirements in each particular case. In general, in the case of administration to adults, a daily dosage of from about 5 mg to about 30 mg, preferably from about 10 mg to about 15 mg, should be appropriate, although the upper limit may be exceeded when this is found to be expedient. The daily dosage can be administered as a single dosage or in divided dosages. Thus part of this invention is a method of treating inflammation, fever, haemorrhage, sepsis, rheumatoid arthritis, osteoarthritis, multiple sclerosis or psoriasis which comprises providing to a patient an amount of the compound of formula I effective to alleviate the inflammation, fever, haemorrhage, sepsis, rheumatoid arthritis, osteoarthritis, multiple sclerosis or psoriasis.

The following Examples illustrate the present invention and are not intended to limit it in any way. The structure of the products and key intermediates was confirmed by NMR spectroscopy.

EXAMPLE 1

2(R)-[1(S)-(Hydroxycarbamoyl)-4-phenylbutyl]-2'-(methanesulphonyl)-4-methyl-2'-phenylvalerohydrazide A solution of 0.165 g of 2(R)-[1(S)-(carboxy)-4-phenylbutyl]-2'-(methanesulphonyl)-4-methyl-2'-phenylvalerohydrazide in 4 ml of dry dimethylformamide was cooled to 0° C. while stirring under nitrogen and 0.09 g of 1-hydroxybenzotriazole and 0.09 g of 1-ethyl-3-(3-dimethylaminopropyl)-carbodiimide hydrochloride were added in succession. After stirring for 40 minutes at 0° C. the solution was treated with 0.18 g of 0-(tert-butyldimethylsilyl)hydroxylamine and the mixture was left to come to room temperature and then stirred overnight. The solvent was evaporated and the residue was partitioned between ethyl acetate and 5% aqueous sodium hydrogen carbonate solution. The ethyl acetate layer was washed in succession with water, 2M sulphuric acid, water and brine and then dried over anhydrous magnesium sulphate. The solvent was evaporated to give a pale pink gum which on crystallization from ether gave 0.05 g of 2(R)-[1(S)-(hydroxycarbamoyl)-4-phenylbutyl]-2'-methanesulphonyl)-4-methyl-2'phenylvalerohydrazide in the form of an off-white solid.

MS: 476 (M+H)$^+$.

nmr (d$_6$ DMSO at 353K): 10.73 (1H, s); 10.30 (1H, br s); 8.46 (1H, br s); 7.50–7.44 (2H, m); 7.42–7.34 (2H, m); 7.30–7.21 (3H, m); 7.18–7.06 (3H, m); 3.17 (3H, s); 2.64–2.54 (1H, m); 2.50–2.30 (2H, m); 2.25–2.11 (1H, m); 1.59–1.23 (6H, m); 1.10–1.02 (1H, m); 0.84 (1H, d, J=6.5 Hz); 0.76 (1H, d, J=7 Hz).

HPLC: Gradient elution using solvent A containing 10% solvent B for 5 minutes increasing to 90% solvent B from 5 minutes to 15 minutes; flow rate 1 ml per minute. Retention time: 16.77 minutes. Solvent A: H$_2$O/0.1% TFA; solvent B: CH$_3$CN/0.085% TFA. Column type: HYPERPEP 300A.

The 2(R)-[1(S)-(carboxy)-4-phenylbutyl]-2'-(methanesulphonyl)-4-methyl-2'-phenylvalerohydrazide used as the starting material was prepared as follows:

(i) A solution of 0.35 g of 2(R)-[1(S)-(tert-butoxycarbonyl)-4-phenylbutyl]-4-methylvaleric acid, prepared in an analogous manner to that described in Example 2, parts (i) and (ii), in 5 ml of dimethylformamide was cooled to 0° C. and treated in succession with 0.1 ml of N-methylmorpholine, 0.16 g of 1-hydroxybenzotriazole, 0.16 g of phenylhydrazine and 0.27 g of 1-ethyl-3-(3-carbodimide hydrochloride. The solution was left to warm to room temperature and was stirred overnight. The solvent was evaporated and the residue was partitioned between ethyl acetate and 5% aqueous sodium hydrogen carbonate solution. The ethyl acetate layer was washed in succession with water, 5% citric acid solution, water and saturated sodium chloride solution, dried over anhydrous magnesium sulphate and evaporated. The residue was purified by flash chromatography on silica gel using hexane/ethyl acetate (6:1) for the elution. There was obtained 0.41 g of a yellow oil which, after crystallization from hexane/ether, gave 0.255 g of 2(R)-[1(S)-(tert-butoxycarbonyl)-4-phenylbutyl]-4-methyl-2'-phenylvalerohydrazide in the form of a white solid.

MS: 439 (M+H)$^+$.

(ii) A solution of 0.19 g of the product from part (i) in 3 ml of pyridine was cooled to 0° C. and 0.15 g of methanesulphonyl chloride was added. The solution was left to stand at room temperature and the solvent was evaporated. The residue was partitioned between ethyl acetate and 2M sulphuric acid and the ethyl acetate layer was washed in succession with 2M sulphuric acid, water, 5% aqueous sodium hydrogen carbonate solution and saturated sodium chloride solution. After drying over anhydrous magnesium sulphate the solvent was evaporated and the residue was purified by flash chromatography using hexane/ethyl acetate (6:1) for the elution. There was obtained 0.19 g of 2(R)-[1(S)-(tert-butoxycarbonyl)-4-phenylbutyl]-2'-(methanesulphonyl)-4-methyl-2-phenylvalerohydrazide in the form of a white solid.

MS: 517 (M+H)$^+$.

(iii) A solution of 0.19 g of the product from part (ii) was dissolved in a mixture of 8 ml of dichloromethane and 4 ml of trifluoroacetic acid and left to stand at room temperature for 5 hours. The solvent was evaporated and the residue was re-evaporated from toluene. This procedure was repeated a further twice to give a residue. This was triturated with ether and the solid was filtered off. There was obtained 0.165 g of 2(R)-[1(S)-(carboxy)-4-phenylbutyl]-2'-(methanesulphonyl)-4-methyl-2'-phenylvalerohydrazide in the form of a white solid.

MS: 461 (M+H)$^+$.

EXAMPLE 2

(E)-2(R)-[1(S)-(Hydroxycarbamoyl-4-phenyl-3-butenyl]-2'-(methanesulphonyl)-4-methyl-2'-phenylvalerohydrazide A solution of 0.095 g of (E)-2(R)-[1(S)-[(tetrahydro-2 (RS)-pyranyloxy)carbamoyl]-4-phenyl-3-butenyl]-2'-phenylvalerohydrazide in a mixture of 10 ml of methanol and 5 ml of dichloromethane was treated with 0.043 mg of 4-toluenesulphonic acid. The mixture was stirred for 3 hours at room temperature and then the solvent was evaporated. The residue was partitioned between ethyl acetate and water. The ethyl acetate layer was dried over anhydrous magnesium sulphate and the solvent was evaporated. The residue was triturated with ether to give 0.051 g of (E)-2(R)-[1(S)-(hydoxycarbamoyl)-4-phenyl-3-butenyl]-2'-(methanesulphonyl)-4-methyl-2'-phenylhydrazide in the form of a white solid.

MS: 474 (M+H)$^+$.

nmr (d$_6$ DMSO at 353K): 10.80 (1H, s); 10.30 (1H, br s); 8.48 (1H, br s); 7.51–7.45 (2H, m); 7.42–7.34 (2H, m); 7.32–7.23 (5H, m); 7.21–7.14 (1H, m); 6.22 (1H, d, J=15.5 Hz); 6.08–5.96 (1H, m); 3.20 (3H, s); 2.70–2.60 (1H, m); 2.42–2.12 (3H, m); 1.58–1.48 (1H, m); 1.46–1.35 (2H, m); 1.14–1.05 (1H, m); 0.85 (3H, d, J=6.5 Hz); 0.76 (3H, d, J=7.5 Hz).

HPLC: Gradient elution using solvent A containing 10% solvent B for 5 minutes increasing to 90% solvent B from 5 minutes to 15 minutes; flow rate 1 ml per minute. Retention time: 16.76 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-(methanesulphonyl)-4methyl-2'-phenyvalerohydrazide used as the starting material was prepared as follows:

(i) A solution of 5.19 g of 4-tert-butyl hydrogen 2(R)-isobutylsuccinate in 50 ml of dry tetrahydrofuran was cooled to −78° C. while stirring under nitrogen. 25 ml of a 2M solution of lithium diisopropylamide in tetrahydrofuran was added dropwise and the mixture was stirred at −78° C. for 15 minutes. A solution of 5.55 g of cinnamyl bromide in 25 ml of dry tetrahydrofuran was then added dropwise and the mixture was left to come to room temperature gradually. After stirring overnight the tetrahydrofuran was evaporated and the residue was partitioned between ethyl acetate and 5% citric acid solution. The ethyl acetate layer was washed with two further portions of 5% citric acid solution, water and saturated sodium chloride solution and then dried over anhydrous magnesium sulphate. The solvent was evaporated to give an orange oil. This was dissolved in 100 ml of hexane to which 2.35 g of cyclohexylamine were added. The mixture was left to stand for 2 hours and the solid formed was collected by filtration. The solid was suspended in ethyl acetate and shaken with two portions of 2M sulphuric acid to give a clear solution. The ethyl acetate solution was washed twice with water and then with saturated sodium chloride solution and subsequently dried over anhydrous magnesium sulphate. After evaporation of the solvent there were obtained 6.41 g of (E)-2(R)-[1(R)-(tert-butoxycarbonyl)-4-phenyl-3-butenyl]-4-methylvaleric acid in the form of a pale cream coloured solid.

(ii) The product obtained in part (i) was dissolved in 50 ml of dry tetrahydrofuran, cooled to −78° C. while stirring and 20.5 ml of a 2M solution of lithium diisopropylamide in tetrahydrofuran were added dropwise. After stirring for 1.75 hours at −78° C. 8 ml of methanol were added dropwise. The mixture was left to come to room temperature gradually and was then stirred overnight. The tetrahydrofuran was evaporated and the residue was partitioned between ethyl acetate and 5% citric acid solution. The ethyl acetate layer was washed in succession with two further portions of citric acid solution, two portions of water and saturated sodium chloride solution and then dried over magnesium sulphate. After evaporation there was obtained an orange oil which contained a mixture of the 1(S),2(R) and 1(R),2(R) isomers of E-2-[1-(tert-butoxycarbonyl)-4-phenyl-3-butenyl-4-methylvaleric acid. The above epimerization procedure was repeated three times to give a mixture substantially enriched in the 1(S),2(R) isomer. The crude product was dissolved in 100 ml of hexane and the solution was treated with 1.9 g of cyclohexylamine. After leaving to stand for 3 hours the precipitated salt was filtered off and dried. There were obtained 5.53 g of a pale cream solid which was converted into the free acid by an analogous procedure to that described in (i). There were obtained 4.36 g of (E)-2(R)-[1(S)-(tertbutoxycarbonyl)-4-phenyl-3-butenyl]-4methyvaleric acid in the form of a yellow solid.

(iii) In an analogous manner to that described in Example 1, part (i), starting from 0.7 g of the carboxylic acid prepared in part (ii) of this Example there was obtained 0.466 g of (E)-2(R)-1(S)-(tertbutoxycarbonyl)-4-phenyl-3-butenyl]-4-methyl-2'-phenylhydrazide in the form of a white solid.

MS: 437 (M+H)$^+$.

(iv) In an analogous manner to that described in Example 1, parts (ii) and (iii), starting from 0.15 g of (E)-2(R)-[1(S)-(tert-butoxycarbonyl)-4-phenyl-3-butenyl]-4-methyl-2'-phenylvalerohydrazide these were obtained 0.14 g of (E)-2(R)-[1(S) carboxy)-4-phenyl-3-butenyl]-2'-(methanesulphonyl)-4-methyl-2'-phenylvalerohydrazide in the form of a white solid.

(v) The carboxylic acid prepared in the preceding paragraph was dissolved in 3 ml of dimethylformamide, cooled to 0° C. and treated in succession with 0.064 g of O-(tetrahydro-2H-pyran-2(RS)-yl)hydroxylamine and 0.061 g of 1-ethyl-3-(3-dimethylaminopropyl) carbodiimide hydrochloride. The mixture was left to come to room temperature and was stirred overnight. The solvent was evaporated *and the residue was partitioned between 5% citric acid solution and ethyl acetate. The ethyl acetate layer was washed with water, 5% sodium hydrogen carbonate solution and saturated sodium chloride solution, then dried over anhydrous magnesium sulphate and evaporated. The resulting white solid was triturated with ether and filtered off to give 0.095 g of (E)-2(R)-[1(S)-[(tetrahydro-2(RS)-pyranyloxy)-carbonyl]-4-phenyl-3-butenyl]-2'-(methansulphony)-4-methyl-2'-phenylvalerohydrazide in the form of a white powder.

MS: 558 (M+H)$^+$.

EXAMPLE 3

Benzyl 3-[2(R)-[1(S)-(hydroxycarbamoyl)-4-phenylbutyl]-4-methylvaleryl]-2-phenylcarbazate In an analogous manner to that described in the first paragraph of Example 2, starting from 0.05 g of benzyl 3-[2(R)-[1(S)-[(tetrahydro-2(RS)-pyranyloxy)carbamoyl]-4-phenylbutyl]-4-methylvaleryl]-2-phenylcarbazate there was obtained 0.032 g of benzyl 3-[2(R)-[1(S)-(hydroxycarbamoyl)-4phenylbutyl]-4-methylvaleryl]-2-phenylcarbazate in the form of a pale cream coloured solid. MS: 532 M+H)$^+$.

nmr (d$_6$ DMSO at 353K): 10.83 (1H, s); 10.47 (1H, br s); 8.62 (1H, br s); 7.64 (2H, m); 7.54 (7H, m); 7.41 (3H, m); 7.33 (1H, m); 7.24 (2H, m); 5.40 (2H, s); 2.76–2.30 (4H, m);

1.75–1.45 (6H, m); 1.22 (1H, m); 0.97 (3H, d, J=7 Hz); 0.90 (3H, d, J=6.5 Hz).

HPLC: Gradient elution using solvent A containing 10% solvent B for 10 minutes increasing to 80% solvent B from 10 minutes to 20 minutes; flow rate 1 ml/minute. Retention time: 19.71 minutes. Solvent A: $H_2O/0.1\%$ TFA; solvent B: $CH_3CN/0.085\%$ TFA. Column type: HYPERPEP 300A.

The benzyl 3-[2(R)-[1(S)-[(tetrahydro-2(RS)-pyranyloxy)carbamoyl]-4-phenylbutyl]-4-methylvaleryl]-2-phenylcarbazate used as the starting material was prepared as follows:

(i) 0.5 g of 2(R)-[1(S)-(tert-butoxycarbonyl-4-phenylbutyl]-4-methyl-2'-phenylvalerohydrazide, prepared as described in Example 1, part (i), was dissolved in 10 ml of diethyl ether and stirred with 10 ml of saturated aqueous sodium hydrogen carbonate solution and 1.0 ml of benzyl chloroformate. After 24 hours the ether layer was separated, washed with saturated sodium chloride solution and dried over anhydrous magnesium sulphate. After removal of the solvent the residue was purified by flash chromatography on silica gel using hexane/ethyl acetate (9.1) for the elution. There was obtained 0.767 g of benzyl 3-[2(R)-[1(S)-(tert-butoxycarbonyl)-4-phenylbutyl]-4-methylvaleryl]-2-phenylcarbazate in the form of a white solid.

MS: 573 $(M+H)^+$.

(ii) In an analogous manner to that described in Example 2, parts (iv) and (v), starting from 0.115 g of the phenylcarbazate prepared in the preceding paragraph there was obtained 0.115 g of benzyl 3-[2(R)-[1(S)-[(tetrahydro-2(RS)-pyranyloxy)]-4-phenylbutyl]-4-methylvaleryl]-2-phenylcarbazate in the form of a colourless gum.

MS: 616 $(M+H)^+$.

EXAMPLE 4

2'-Acetyl-2(R)-[1(S)-(hydroxycarbamoyl)-4-phenylbutyl]-4-methyl-2'-phenylvalerohydrazide In an analogous manner to that described in the first paragraph of Example 2, starting from 0.09 g of 2'-acetyl-2(R)-[1(S)-[(tetrahydro-2(RS)-pyranyloxy)carbamoyl]-4-phenylbutyl]-4-methyl-2'-phenylvalerohydrazide there was obtained 0.062 g of 2'-acetyl-2(R)-[1(S)-[(tetrahydro-2-(RS)-pyranyloxy)carbamoyl]-4-phenylbutyl]-4-methyl-2'-phenylvalerohydrazide in the form of a white solid.

MS: 440 $(M+H)^+$.

HPLC: Gradient elution using solvent A containing 25% solvent B for 5 minutes and then increasing to 60% solvent B from 5 minutes to 20 minutes; flow rate 1 ml/minute. Retention time: 14.97 minutes. Solvent A: $H_2O/0.1\%$ TFA; solvent B: $CH_3CN/0.085\%$ TFA. Column type: HYPERPEP 300A.

The 2'-acetyl-2(R)-[1(S)-[(tetrahydro-2(RS)-pyranyloxy)carbamoyl]-4-phenylbutyl]-4-methyl-2'-phenylvalerohydrazide used as the starting material was prepared as follows:

(i) A mixture of 0.2 g of 2(R)-[1(S)-(tert-butylcarbonyl)-4-phenylbutyl]-4-methyl-2'-phenylvalerohydrazide, prepared as described in Example 1, part (i), 0.3 ml of acetic anhydride and 0.35 ml of N-methylmorpholine in 2 ml of dichloromethane was left to stand at room temperature for 3 days. The dichloromethane was evaporated and the residue was partitioned between ethyl acetate and 5% sodium hydrogen carbonate solution. The ethyl acetate solution was washed with 5% sodium hydrogen carbonate solution, water, 5% citric acid solution, water and saturated sodium chloride solution and then dried over anhydrous magnesium sulphate. The solvent was evaporated and the residue was purified by flash chromatography on silica gel using hexane/ethyl acetate (1.1) for the elution. There was obtained 0.21 g of 2'-acetyl-2(R)-[1(S)-(tert-butoxycarbonyl)-4-phenylbutyl]-4-methyl-2'-phenylvalerohydrazide in the form of a white solid

MS: 481 $(M+H)^+$.

(ii) In an analogous manner to that described in Example 2, parts (iv) and (v), starting from 0.21 g of the hydrazide prepared in the preceding paragraph there was obtained 0.09 g of 2'-acetyl-2(R)-[1(S)-[(tetrahydro-2(RS)-2-pyranyloxy)carbamoyl]-4-phenylbutyl]-4-methyl-2'-phenylvalerohydrazide in the form of a white solid.

MS: 524 $(M+H)^+$.

EXAMPLE 5

(E)-2(R)-[1(S)-(Hydroxycarbamoyl)-4-phenyl-3-butenyl]-2'-methanesulphonyl)-4-methyl-2'-(2-pyridyl)valerohydrazide In an analogous manner to that described in the first paragraph of Example 2, starting from 0.11 g of (E)-2(R)-[1(S)-[(tetrahydro-2(RS)-pyranyloxy)carbamoyl]-4-phenyl-3-butenyl]-2'-(methanesulphonyl)-4-methyl-2'-(2-pyridyl)valerohydrazide there was obtained, after washing the ethyl acetate solution of the product with 2% aqueous sodium hydrogen carbonate solution to give the free base, 0.052 g of (E)-2(R)-[1(S)-(hydroxycarbamoyl)-4-phenyl-3-butenyl]-2'-(methanesulphonyl)-4-methyl-2'-(2-pyridyl)valerohydrazide in the form of a white solid.

MS: 475 ($M+H^+$.

nmr ($d_6$ DMSO at 353K): 10.86 (1H, s); 10.27 (1H, br s); 8.45 (1H, br s); 8.35 (1H, m); 7.30 (1H, m); 7.34–7.12 (7H, m); 6.32 (1H, d, J=15.5 Hz); 6.13–6.04 (1H, m); 3.51 (3H, s); 2.79–2.69 (1H, m); 2.50–2.30 (3H, m); 1.53–1.50 (2H, m); 1.19–1.10 (1H, m); 0.91 (3H, d, J=7.0 Hz); 0.83 (3H, d, J=6.5 Hz).

HPLC: Gradient elution using solvent A containing 10% solvent B for 5 minutes increasing to 90% solvent B from 5 to 20 minutes; flow rate 1 ml per minute. Retention time: 16.20 minutes. Solvent A: $H_2O/0/1\%$ TFA; solvent B: $CH_3CN/0.085\%$ TFA. Column type: HYPERPEP 300A.

The (E)-2(R)-[1(S)-[(tetrahydro-2(RS)-pyranyloxy)carbamoyl]-4-phenyl-3-butenyl]-2'-(methanesulphonyl)-4-methyl-2'-(2-pyridyl)valerohydrazide used as the starting material was prepared as follows:

In an analogous manner to that described in Example 2, parts (iii)–(v), starting from (E)-(2R)-[1(S)-(tert-butoxycarbonyl)-4-phenyl-3-butenyl]-4-methylvaleric acid and 2-hydrazinopyridine there was obtained (E)-2(R)-[1(S)-(tetrahydro-2(RS)-pyranyloxy)carbamoyl]-4-phenyl-3-butenyl]-2'-(methanesulphonyl)-4-methyl-2'-(2-pyridyl)valerohydrazide in the form of a white solid.

MS: 559 $(M+H)^+$.

EXAMPLE 6

(E)-2'-(2-Benzothiazolyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.086 g of (E)-2'-(2- benzothiazolyl)-2(R)-[1(S)-[(tetrahydro-2(RS)-pyranyloxy) carbamoyl]-4-phenyl-3-butenyl]-2'-(methanesulphonyl)-4methylvalerohydrazide there was obtained, after washing the ethyl acetate solution of the product with a 2% solution of aqueous sodium hydrogen carbonate, 0.045 g of (E)-2'-(2-benzothiazolyl)-2(R)-[1(S)-(hydroxycarbamoyl)-4-phenyl-3-butenyl]-2'-(methanesulphonyl)-4-methylvalerohydrazide in the form of a white solid.

MS: 531 (M+H)$^+$.

HPLC: Gradient elution using solvent A containing 5% solvent B for 5 minutes and then increasing to 95% solvent B from 5 to 20 minutes; flow rate 1 ml/minute. Retention time: 18.16 minutes. Solvent A: H$_2$O/0.1% TFA; solvent B: CH$_3$CN/0.085% TFA. Column type: HYPERPEP 300A.

The (E)-2'-(2-benzothiazolyl)-2(R)-[1(S)-[(tetrahydro-2 (RS)-pyranyloxy)carbamoyl]-4-phenyl-3-butenyl]-2'-(methanesulphonyl)-4-methylvalerohydrazide used as the starting material was prepared as follows:

In an analogous manner to that described in Example 2, parts (iii)–(v), starting from (E)-2(R)[1(S)-(tert.butoxycarbonyl)-4-phenyl-3-butenyl]-4-methylavaric acid and 2-hydrazinobenzothiazole these was obtained (E)-2'-(2-benzothiazolyl)-2(R)-[1(S)-[(tetrahydro-2(RS)-pyranyloxy)carbamoyl]-4-phenyl-3-butenyl]-2'-(methanesulphonyl)-4-methylvalerohydrazide in the form of a white solid.

EXAMPLE 7

(E)-2(R)-[1(S-(Hydroxycarbamoyl)-4-phenyl-3-butenyl]-2'-(methanesulphonyl)-4-methyl-2'-(2-quinolyl)valerohydrazide In an analogous manner to that described in the first paragraph of Example 2, starting from 0.05 g of (E)-2(R)-[1(S)-[(tetrahydro-2(RS)-pyranyloxy)carbamoyl-4-phenyl-3-butenyl]-2'-(methanesulphony) 4-methyl-2'-(2-quinolyl) valerohydrazide there was obtained, after washing the ethyl acetate solution of the product with 2% aqueous sodium hydrogen carbonate solution, 0.026 g of (E)-2-(R)-[1(S)-(hydroxycarbamoyl)-4-phenyl-3-butenyl]-2'-(methanesulphonyl)-4-methyl-2'-(2-quinolyl) valerohydrazide in the form of a white solid.

MS: 524 (M+H)$^+$.

HPLC: Gradient elution using solvent A containing 10% solvent B for 5 minutes increasing to 90% solvent B from 5 to 20 minutes; flow rate 1 ml/minute. Retention time: 17.90 minutes. Solvent A: H$_2$O/0.1% TFA; solvent B:/CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-(methanesulphonyl) 4-methyl-2'-(2-quinolyl)valerohydrazide used as the starting material was prepared as follows:

In an analogous manner to that described in Example 2, parts (iii)–(v), starting from (E)-2(R)-[1(S)-(tert-butoxycarbonyl)-4-phenyl-3-butenyl]-4-methylvaleric acid and 2-hydrazinoquinoline there was obtained (E)-2(R)-[1 (S)-[(tetrahydro-2(RS)-pyranyloxy)carbamoyl]-4-phenyl-3-butenyl]-2'-(methanesulphonyl)4-methyl-2'-(2-quinolyl) valerohydrazide in the form of a white solid.

EXAMPLE 8

1(E)-2(R)-[1(S)-(Hydroxycarbamoyl)-4-phenyl-3-butenyl]-2'-(methanesulphonyl)-2'-(4-methoxyphenyl)-4-methylvalerohydrazide In an analogous manner to that described in the first paragraph of Example 2, starting from 0.338 g of (E)-2(R)-1(S)-[(tetrahydro-2(RS)-pyranyloxy)carbamoyl]-4-phenyl-3-butenyl]-2'-(methanesulphonyl)-2'-(methoxyphenyl)-4-methylvalerohydrazide there was obtained 0.195 g of 1(E)-2(R)-[1(S)-(hydroxycarbamoyl)-4-phenyl-3-butenyl]-2'-(methanesulphonyl)-2'-(4-methoxyphenyl)-4methylvalerohydrazide in the form of a cream coloured solid.

MS: 504 (M+H)$^+$.

HPLC: Gradient elution using solvent A containing 5% solvent B for 5 minutes increasing to 95% solvent B from 5 to 20 minutes; flow rate 1 ml/minute. Retention time: 16.53 minutes. Solvent A: H$_2$O/0.01% TFA: solvent B: CH$_3$CN/ 0.085% TFA. Column type: HYPERPEP 300A.

The (E)-2(R)-1(S)-[(tetrahydro-2(RS)-pyranyloxy) carbamoyl]-4-phenyl-3-butenyl]-2'-(methanesulphonyl)-2'-(methoxypheny)-4-methylvalerohydrazide used as the starting material was prepared as follows:

In an analogous manner to that described in Example 2, parts (iii)–(v), starting from (E)-2(R)-[1(S)-(tert-butoxycarbonyl)-4-phenyl-3-butenyl]-4-methylvaleric acid and 4-methoxyphenylhydrazine there was obtained (E)-2 (R)-[1(S)-[(tetrahydro-2(RS)-pyranyloxy)carbamoyl]-4-phenyl-3-butenyl]-2'-(methanesulphonyl)-2'-(methoxypheny)-4-methylvalerohydrazide in the form of a white solid.

EXAMPLE 9

(E)-2(R)-[1(S)-(Hydroxcarbamoyl)-4-phenyl-3-butenyl]-2'-(methanesulphony)-4-methyl-2'-(2-methylphenyl)valerohydrazide In an analogous manner to that described in the first paragraph of Example 2, starting from 0.37 g of (E)-2(R)-[1(S)-[(tetrahydro-2-(RS)-pyranyloxy)carbamoyl]-4-phenyl-3-butenyl]-2'-(methanesulphonyl)-4-methyl-2-'-(2-methylphenyl)valerohydrazide there was obtained 0.192 g of (E)-2(R)-[1(S)-(hydroxycarbamoyl)-4-phenyl-3-butenyl]-2'-(methanesulphonyl)-4-methyl-2'-(2-methylphenyl)valerohydrazide in the form of a cream coloured solid.

MS: 488 (M+H)$^+$.

HPLC: Gradient elution using solvent A containing 5% solvent B increasing to 95% solvent B over 15 minutes; flow rate 1 ml/minute. Retention time: 12.37 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2-(RS)-pyranyloxy) carbamoyl]-4-phenyl-3-butenyl]-2'-(methanesulphonyl)-4-methyl-2'-(2-methylphenyl)valerohydrazide used as the starting material was prepared as follows:

(i) In an analogous manner to that described in Example 1, part (i), starting from 0.7 g of (E)-2(R)-[1(S)-(tert-butoxycarbonyl)-4-phenyl-3-butenyl]-4-methylaric acid and o-tolylhydrazine there was obtained 0.5 g of (E)-2(R)-[1(S)-(tert-butoxycarbonyl)-4-phenyl-3-butenyl]-4-methyl-2'-(2-methylphenyl) valerohydrazide in the form of a cream coloured solid. MS: 451 (M+H)$^+$.

(ii) A solution of 0.15 g of (E)-2(R)-[1(S)-(tert-butoxycarbonyl)-4-phenyl-3-butenyl]-4-methyl-2'-(2-methylphenyl)valerohydrazide in 5 ml of dichloromethane was treated with 0.09 g of pyridine and 0.1 g of methanesulphonic anhydride. After stirring for 1.5 hours a further 0.05 g of pyridine and 0.06 g of methanesulphonic anhydride were added and the mixture was stirred for a further 2 hours. The solvent was evaporated and the residue was partitioned between ethyl acetate and 5% citric acid solution. The ethyl acetate solution was washed with water, 5% aqueous sodium hydrogen carbonate solution and saturated sodium chloride solution and then dried over anhydrous magnesium sulphate. After evaporation of the solvent the residue was purified by flash chromatography on silica gel using hexane/ethyl acetate (6:1) for the elution. There was obtained 0.16 g of (E)-2(R)-[1 (S)-(tert-butoxycarbonyl)-4-phenyl-3-butenyl]-2'-(methanesulphonyl)-4-methyl-2'-(2-methylphenyl) valerohydrazide in the form of a yellow gum.

(iii) The hydrazide prepared in the preceding paragraph was treated in an analogous manner to that described in Example 1, part (iii), followed by that described in Example 2, part (v), to give (E)-2(R)-1(S)-[(tetrahydro-2(RS)-pyranyloxy)carbamoyl]-4-phenyl-3-butenyl]-2'-(methanesulphonyl)-4-methyl-2'-(2-methylphenyl) valerohydrazide in the form of cream coloured solid. MS: 572 (M+H)$^+$.

EXAMPLE 10

(E)-2(R)-[1(S)-(Hydroxycarbonyl)-4-phenyl-3-butenyl]-2'-(methanesulphonyl)-4-methyl-2'-(1-naphthyl)valerohydrazide In an analogous manner to that described in the first paragraph of Example 2, starting from 0.09 g of (E)-2(R)-[1(S)-[(tetrahydro-2(RS)-pyranyloxy)carbamoyl]-4-phenyl-3-butenyl]-2'-(methanesulphonyl)-4-methyl-2'-(1-naphthyl) valerohydrazide there was obtained 0.053 g of (E)-2(R)-[1 (S)-(hydroxycarbamoyl)-4-phenyl-3-butenyl]-2'-(methanesulphonyl)-4-methyl-2'-(1-naphthyl) valerohydrazide in the form of a cream coloured solid. MS: 524 (M+H)$^+$.

HPLC: Gradient elution using solvent A containing 5% solvent B increasing to 95% solvent B over 15 minutes; flow rate 1 ml/minute. Retention time 12.83 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-(methanesulphonyl)-4methyl-2'-(1-naphthyl)valerohydrazide used as the starting material was prepared as follows:

In an analogous manner to that described in Example 9, parts (i)–(iii), starting from (E)-2(R)-[1(S)-(tert-butoxycarbonyl)-4-phenyl-3-butenyl)-4methylaric acid and 1-naphthylhydrazine there was obtained (E)-2(R)-[1(S)-[(tetrahydro-2(RS)-pyranyloxy)carbamoyl]-4-phenyl-3-butenyl]-2'-(methanesulphonyl)-4-methyl-2'-(1-naphthyl) valerohydrazide in the form of a cream coloured solid. MS: 608 (M+H)$^+$.

EXAMPLE 11

(E)-2'-(3-Hydroxybenzyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.375 g of (E)-2'-(3-hydroxybenzyl)-2(R)-[1(S)-[(tetrahydro-2(RS)-pyranyloxy) carbonyl]-4-phenyl-3-butenyl]-2'-(methanesulphonyl)-4-methylvalerohydrazide there was obtained 0.29 g of (E)-2'-(3hydroxybenzyl)-2(R)-[1(S)-(hydroxycarbamoyl)-4-phenyl-3-butenyl]-2'-(methanesulphonyl)-4-methylvalerohydrazide in the form of a white solid. MS: 503 (M+H)$^+$.

nmr (d$_6$ DMSO at 353K): 10.23 (1H, br s); 10.09 (1H, s); 8.98 (1H, s); 8.41 (1H, br s); 7.30 (4H, m); 7.18 (1H, m); 7.09 (1H, m) 6.83–6.73 (2H, m); 6.67 (1H, m); 6.24 (1H, d, J=15.5 Hz); 6.05–5.94 (1H, m); 4.56–4.48 (2H, m), 3.14 (3H, s); 2.55–2.45 (1H, m) 2.33–2.18 (2H, m); 2.16–2.02 (1H, m); 1.50–1.40 (1H, m); 1.38–1.21 (1H, m) 1.05–0.95 (1H, m); 0.75 (3H, d, J=7 Hz); 0.71 (3H, d, J=7 Hz).

HPLC: Gradient elution using solvent A containing 5% solvent B increasing to 95% solvent B over 15 minutes; flow rate 1 ml/minute. Retention time: 10.95 minutes. Solvent A: H$_2$O/0.1% TFA; Solvent B: CH$_3$CN/0.085% TFA. Column type: HYPERPEP 300A.

The (E)-2'-(3-hydroxybenzyl)-2(R)-[1(S)-[(tetrahydro-2(RS)-pyranyloxy)carbonyl]-4-phenyl-3-butenyl]-2'-(methanesulphonyl)-4-methylvalerohydrazide used as the starting material was prepared as follows:

In an analogous manner to that described in Example 9, parts (i)–(iii), starting from (E)-2(R)[1(S)-(tert-butoxycarbonyl)-4-phenyl-3-butenyl]-4-methylaric acid and 3-hydroxybenzylhydrazine there was obtained (E)-2'-(3-hydroxybenzyl)-2(R)-[1(S)-[(tetrahydro-2(RS)-pyranyloxy) carbamoyl]-4-phenyl-3-butenyl]-2'-(methanesulphonyl)-4-methylvalerohydrazide in the form of a white solid. MS: 588 (M+H)$^+$.

EXAMPLE 12

(E)-2'-(2,4-Difluorophenyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.13 g of (E)-2'-(2, 4-difluorophenyl)-2(R)-[1(S)-[(tetrahydro-2(RS)-pyranyloxy)carbamoyl]-4-phenyl-3-butenyl]-2'-(methanesulphonyl)-4methylvalerohydrazide there was obtained 0.083 g of (E)-2'-(2,4-difluorophenyl)-2(R)-[1(S)-(hydroxycarbonyl)-4-phenyl-3-butenyl]-2'-(methanesulphonyl)-4-methylvalerohydrazide in the form of a white solid. MS: 510 (M+H)$^+$.

HPLC: Gradient elution using solvent A containing 5% solvent B increasing to 95% solvent B over 15 minutes; flow rate 1 ml/minute. Retention time: 12.37 minutes. Solvent A: H$_2$O/0.1% TFA; solvent B: CH$_3$CN/0.085% TFA. Column type: HYPERPEP 300A.

The (E)-2'-(2,4-difluorophenyl)-2(R)-[1(S)-[(tetrahydro-2(RS)-pyranyloxy)carbamoyl]-4-phenyl-3butenyl]-2'-(methanesulphonyl)-4-methylvalerohydrazide used as the starting material was prepared as follows:

In an analogous manner to that described in Example 2, parts (iii)–(v), starting from E-2(R)-[1(S)-(tert-butoxycarbonyl)-4-phenyl-3-butenyl]-4-methylvaleric acid and 2,4-difluorophenylhydrazine there was obtained (E)-2'-(2,4-difluorophenyl)-2(R)-[1(S)-[(tetrahydro-2(RS)-pyranyloxy)carbamoyl]-4-phenyl-3-butenyl]-2'-(methanesulphonyl)-4-methylvalarohydrazide in the form of a white solid.

EXAMPLE 13

(E)-2(R)-[1(S)-(Hydroxcarbamoyl)-4-phenyl-3-butenyl]-2'-(methanesulphonyl)-4-methyl-2'-(4-nitrophenyl)valerohydrazide In an analogous manner to that described in the first paragraph of Example 2, starting from 0.1 g of (E)-2(R)-[(tetrahydro-2(RS)-pyranyloxy)carbamoyl]-4-phenyl-3-butenyl]-2'-(methanesulphonyl)-4-methyl-2'-(4- nitrophenyl)valerohydrazide there was obtained 0.06 g of (E)-2(R)-[1(S)-(hydroxycarbamoyl)-4-phenyl-3-butenyl]-2'-(methanesulphonyl)-4-methyl-2'-(4-nitrophenyl) valerohydrazide in the form of a yellow solid.
MS: 519 (M+H)+.

HPLC: Gradient elution using solvent A containing 5% solvent B increasing to 95% solvent B over 15 minutes; flow rate 1 ml/minute. Retention time 12.54 minutes. Solvent A: H₂O; solvent B: CH₃CN. Column type: HYPERPEP 300A.

The (E)-2(R)-[(tetrahydro-2(RS)-pyranyloxy) carbamoyl]-4-phenyl-3-butenyl]-2'-(methanesulphonyl)-4-methyl-2'-(4-nitrophenyl)valerohydrazide used as the starting material was prepared as follows:

In an analogous manner to that described in Example 2, parts (iii)–(v), starting from E-2(R)-[1(S)-(tert-butoxycarbonyl)-4-phenyl-3-butenyl]-4-methylvaleric acid and 4-nitrophenylhydrazine there was obtained (E)-2(R)-[1 (S)-[(tetrahydro-2(RS)-pyranyloxy)carbamoyl]-4-phenyl-3-butenyl]-2'-(methanesulphonyl)-4-methyl-2'-(4-nitrophenyl)valerohydrazide in the form of a yellow solid.

EXAMPLE 14

(E)-2'-Acetyl-2(R)-[1(S)-(hydroxycarbamoyl)-4-phenyl-3-butenyl]-4-methyl-2'-(2-pyridyl) valerohydrazide In a manner to that described in the first paragraph of Example 2, starting from 0.1 g of (E)-2'-acetyl-2(R)-[1(S)-[(tetrahydro-2(RS)-pyranyloxy)carbamoyl]-4-phenyl-3-butenyl]-4-methyl-2'-(2-pyridyl)valerohydrazide there was obtained, after washing the ethyl acetate solution of the product with 2% aqueous sodium hydrogen carbonate solution to give the free base, 0.035 g of (E)-2'-acetyl-2(R)-[1 (S)-(hydroxycarbomoyl)-4-methyl-2'-(2-pyridyl) valerohydrazide in the form of a cream coloured solid.
MS: 439 (M+H)+.

HPLC: Gradient elution using solvent A containing 5% solvent B for 5 minutes increasing to 95% solvent B from 5 minutes to 20 minutes; flow rate 1 ml/minute. Retention time: 15.67 minutes. Solvent A: H₂O/0.1% TFA; solvent B: CH₃CN/0.085% TFA. Column type: HYPERPEP 300A.

The (E)-2'-acetyl-2(R)-[1(S)-[(tetrahydro-2(RS)-pyranyloxy)carbamoyl]-4-phenyl-3-butenyl]-4-methyl-2'-(2-pyridyl)valerohydrazide used as the starting material was prepared as follows.

In an analogous manner to that described in Example 4, parts (i) and (ii), starting from (E)-2(R)-[1(S)-(tert-butoxycarbonyl)-4-phenyl-3-butenyl]-4-methyl-2'-(2-pyridyl)valerohydrazide there was obtained (E)-2'-acetyl-2 (R)-[1(S)-[(tetrahydro-2(RS)-pyranyloxy)carbamoyl]-4-phenyl-3-butenyl]-4-methyl-2'-(2-pyridyl)valerohydrazide in the form of a white solid.

EXAMPLE 15

(E)-2(R)-[1(S)-(Hydroxcarbamoyl)-4-phenyl-3-butenyl]-2'-(methanesulphonyl)-2',4-dimethylvalerohydrazide In an analogous manner to that described in the first paragraph of Example 2, starting from 0.122 g of (E)-2(R)-[1(S)-[(tetrahydro-2(RS)-pyranyloxy)carbamoyl]-4-phenyl-3-butenyl]-2-(methanesulphonyl)-2',4-dimethylvalerohydrazide there was obtained 0.033 g of (E)-2(R)-[1(S)-(hydroxycarbamoyl)-4-phenyl-3-butenyl]-2'-(methanesulphonyl)-2',4-dimethylvalerohydrazide in the form of an off-white solid.
MS: 412 (M+H)+.

nmr (d₆ DMSO): 10.56 (1H, s); 10.46 (1H, s); 8.75 (1H, s); 7.35–7.25 (4H, m); 7.23–7.15 (1H, m); 6.31 (1H, d, J=15.5 Hz); 6.10–6.00 (1H, m); 3.06 (3H, s); 3.04 (3H, s); 2.55–2.45 (1H, m); 2.37 (3H, m); 1.54–1.36 (2H, m); 1.02–0.93 (1H, m); 0.84 (3H, d, J=7 Hz); 0.81 (3H, d, J=7.5 Hz).

HPLC: Gradient elution using solvent A containing 10% solvent B for 5 minutes increasing to 90% solvent B from 5 minutes to 20 minutes; flow rate 1 ml/minute. Retention time: 14.72 minutes. Solvent A: H₂O/0.1% TFA; solvent B: CH₃CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2-(methanesulphonyl)-2', 4-dimethylvalerohydrazide used as the starting material was prepared as follows:

(i) A mixture of 11 g of pentafluorophenol and 4.12 g of 1,3-dicyclohexylcarbodiimide in 50 ml of hexane was stirred at room temperature for 5 minutes. The resulting solid was filtered off, washed with hexane, dried and then added to a solution of 5.0 g of (E)-2(R)-[1(S)-(tert-butoxycarbonyl)-4-phenyl-3-butenyl]-4-phenyl-3-3-butenyl]-4-methylvaleric acid in 50 ml of dimethoxyethane. The mixture was left to stand at 4° C. over-night and then filtered to remove dicyclohexylurea. The filtrate was evaporated, the residue was dissolved in 50 ml of dichloromethane and 3 ml of hydrazine hydrate were added to the solution obtained. The mixture was stirred for 6 hours and then washed in succession with 5% citric acid solution, saturated sodium hydrogen carbonate solution, water and saturated sodium chloride solution, dried over anhydrous magnesium sulphate and evaporated. The residue was triturated with hexane/ethyl acetate (4:1) and the resulting solid was filtered off. There were obtained 4.68 g of (E)-2(R)-[1(S)-(tert-butoxycarbonyl)-4-phenyl-3-butenyl]-4-methylvalerohydrazide in the form of an off-white solid.
MS: 361 (M+H)+.

(ii) In an analogous manner to that described in Example 9, parts (ii) and (iii), starting from 8.96 g of (E)-2(R)-[1(S)-(tert-butoxycarbonyl)-4-phenyl-3-butenyl]-4-methylvalerohydrazide there were obtained 2.83 g of (E)-2(R)-[1(S)-[(tetrahydro-2(RS)-pyranyloxy) carbamoyl]-4-phenyl-3-butenyl]-2'-(methanesulphonyl)-4-methylvalerohydrazide in the form of a white solid.
MS: 482 (M+H)+.

(iii) A solution of 0.34 g of the hydrazide prepared in the part (ii) in 7 ml of dimethylformamide was treated with 0.126 g of methyl iodide and 0.293 g of anhydrous potassium carbonate. The mixture was stirred at room temperature for 3 hours and the volatiles were removed by evaporation. The residue was partitioned between ethyl acetate and 5% citric acid solution. The ethyl acetate phase was washed with water and with saturated sodium chloride solution and then dried over anhydrous magnesium sulphate. After evaporation of the solvent the residue was purified by flash chromatography on silica gel using hexane/ethyl acetate (4:1) and then hexane/ethyl acetate (2:1) for the elution. There was obtained 0.122 g of (E)-2(R)-[1(S)-[(tetrahydro-2(RS)-pyranyloxy)carbamoyl]-4-phenyl-3-butenyl]-2'-(methanesulphony)-4-methylvalerohydrazide in the form of a white solid.

EXAMPLE 16

(E)-2(R)-[1(S)-(Hydroxycarbamoyl)-4-phenyl-3-butenyl]-2'-(methanesulphonyl)-4-methylvalerohydrazide In an analogous manner to that described in the first paragraph of Example 2, starting from 0.151 g of (E)-2(R)-

[1(S)-[(tetrahydro-2(RS)-pyranyloxy)carbamoyl]-4-phenyl-3-butenyl]-2'-(methanesulphonyl)-4-methylvalerohydrazide there was obtained 0.06 g of (E)-2(R)-[1(S)-(hydroxycarbamoyl)-4-phenyl-3-butenyl]-2'-(methanesulphonyl)-4-methylvalerohydrazide in the form of a off-white solid.
MS: 398 (M+H)+.

nmr (d$_6$ DMSO):10.55 (1H, s); 10.34 (1H, s); 9.52 (1H, s); 8.85 (1H, s); 7.36–7.25 (4H, m); 7.23–7.16 (1H, m); 6.30 (1H, d, J=15.5 Hz); 6.08–5.98 (1H, m); 2.96 (3H, s); 2.56–2.46 (1H, m); 2.39–2.13 (3H, m); 1.53–1.33 (2H, m); 1.01–0.93 (1H, m); 0.83 (3H, d, J=6.5 Hz); 0.80 (3H, d, J=7 Hz).

HPLC: Gradient elution using solvent A containing 10% solvent B for 5 minutes increasing to 90% solvent B from 5 minutes to 20 minutes; flow rate 1 ml/minute. Retention time: 14.13 minutes. Solvent A: H$_2$O/0.1% TFA; solvent B: CH$_3$CN/0.085% TFA. Column type: HYPERPEP 300A.

EXAMPLE 17

(E)-2'-Benzyl-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, from 0.183 g of (E)-2'-benzyl-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.142 g of (E)-2'-benzyl-2(R)-[1(S)-(hydroxycarbamoyl)-4-phenyl-3-butenyl]-2'-(methanesulphonyl)-4-methylvalerohydrazide in the form of an off-white solid.
MS: 488 (M+H)+.

nmr (d$_6$ DMSO at 353K); 10.22 (1H, br s); 10.1 (1H,s); 8.40 (1H, br s); 7.40–7.24 (9H, m); 7.22–7.15 (1H, m); 6.23 (1H, d, J=15 Hz); 6.05–5.94 (1H, m); 4.63 (2H, m); 3.15 (3H, s); 2.54–2.44 (1H, m); 2.31–2.17 (2H, m); 2.14–2.01 (1H, m); 1.51–1.49 (1H, m); 1.34–1.18 (1H, m); 1.04–0.95 (1H, m); 0.74 (3H, d, J=6.5 Hz); 0.70 (3H, d, J=7.0 Hz).

HPLC: Gradient elution using solvent A containing 5% solvent B increasing to 95% solvent B over 15 minutes; flow rate 1 ml/minute. Retention time: 12.18 minutes. Solvent A: H$_2$O/0.1% TFA; solvent B: CH$_3$CN/0.085% TFA. Column type: HYPERPEP 300A.

The (E)-2'-benzyl-2(R)-[1(S)-[(tetrahydro-2(RS)-pyranyloxy)carbamoyl]-4-phenyl-3-butenyl]-2'-(methanesulphonyl)-4-methylvalerohydrazide used as the starting material was prepared in an analogous manner to that described in Example 15, part (iii), starting from (E)-(2R)-[1(S)-[(tetrahydro-2(RS)-pyranyloxy)carbamoyl]-4-phenyl-3-butenyl]-2'-(methanesulphonyl)-4-methylvalerohydrazide by reaction with benzyl bromide.

EXAMPLE 18

(E)-2(R)-[1(S)-(Hydroxycarbamoyl)-4-phenyl-3-butenyl]-2'-(methanesulphonyl)-2'-(4-methoxybenzyl)-4-methylvalerohydrazide In an analogous manner to that described in the first paragraph of Example 2, starting from 0.105 g of (E)-2(R)-[1(S)-[(tetrahydro-2(RS)-pyranyloxy)carbamoyl]-4-phenyl-3-butenyl]-2'-(methanesulphonyl)-2'-(4-methoxybenzyl)-4-methylvalerohydrazide there was obtained 0.061 g of (E)-2(R)-[1(S)-(hydroxycarbamoyl)-4-phenyl-3-butenyl]-2'-(methanesulphonyl)-2'-(methanesulphonyl)-2'-(4-methoxybenzyl)-4-methylvalerohydrazide valerohydrazide in the form of a white solid.
MS: 518 (M+H)+.

HPLC: Gradient elution using solvent A containing 35% solvent B for 5 minutes increasing to 85% solvent B from 5 minutes to 20 minutes; flow rate 1 ml/minute. Retention time 7.20 minutes. Solvent A: H$_2$O/0.1% TFA; solvent B: CH$_3$CN/0.085% TFA. Column type: HYPERSIL 300A.

The (E)-2(R)-[1(S)-[(tetrahydro-2(RS)-pyranyloxy)carbamoyl]-4-phenyl-3-butenyl]-2'-(methanesulphonyl)-2'-(4-methoxybenzyl)-4-methylvalerohydrazide used as the starting material was prepared in an analogous manner to that described in Example 15, part (iii), starting from (E)-(2R)-[1(S)-[(tetrahydro-2(RS)-pyranyloxy)carbamoyl]-4-phenyl-3-butenyl]-2'-(methanesuophonyl)-4-methylvalerohydrazide by reaction with 4-methoxybenzyl bromide.

EXAMPLE 19

(E)-2'-Allyl-2(R)-[1(S)-(hydroxycarbamoyl)-4-phenyl-3-butenyl]-2'-(methanesulphonyl)-4-methylvalerohyrazide In an analogous manner to that described in the first paragraph of Example 2, starting from 0.168 g of (E)-2'-allyl-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.013 g of (E)-2'-allyl-2(R)-[1(S)-(hydroxycarbamoyl)-4-phenyl-3-butenyl]-2'-(methanesulphonyl)-4-methylvalerohydrazide in the form of a white solid.
MS: 438 (M+H)+.

nmr (d$_6$ DMSO at 353K): 10.26 (1H, br s); 10.08 (1H, s); 8.44 (1H, br s); 7.35–7.25 (4H, m); 7.22≧7.15 (1H, m); 6.33 (1H, d, J=15.5 Hz); 6.13–6.03 (1H, m) 5.90–5.78 (1H, m); 5.28 (1H, m); 5.18 (1H, m); 4.05 (1H, m); 3.06 (3H, s); 2.63–2.53 (1H, m); 2.44–2.25 (3H, m); 1.59–1.45 (2H, m); 1.14–1.03 (1H, m); 0.85 (3H, d, J=7 Hz); 0.82 (3H, d, J=6.5 Hz).

HPLC: Gradient elution using solvent A containing 5% solvent B increasing to 95% solvent B over 15 minutes; flow rate 1 ml/minute. Retention time: 11.36 minutes. Solvent A: H$_2$O/0.1% TFA; solvent B: CH$_3$CN/0.085% TFA. Column type: HYPERPEP 300A.

The (E)-2'-allyl-2(R)-[1(S)-[(tetrahydro-2(RS)-pyranyloxy)carbamoyl]-4-phenyl-3-butenyl]-2'-(methanesulphonyl)-4-methylvalerohydrazide used as the starting material was prepared as described in Example 15, part (iii), starting from (E)-(2R)-[1(S)-[(tetrahydro-2(RS)-pyranyloxy)carbamoyl]-4-phenyl-3-butenyl]-2'-(methanesulphonyl)-4-methylvalerohydrazide by reaction with allyl bromide.

EXAMPLE 20

(E)-2'-(4-Bromobenzyl-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.215 g of (E)-2'-(4-bromobenzyl)-2(R)-[1(S)-[(tetrahydro-2(RS)-pyranyloxy)carbamoyl]-4-phenyl-3-butenyl]-2'-(methanesuophonyl)-4-methylvalerohydrazide there was obtained 0.147 g of (E)-2'-(4bromobenzyl)-2-(R)-[1(S)-(hydroxycarbamoyl)-4-phenyl-3-butenyl]-2'-(methanesulphonyl)-4-methylvalerohydrazide in the form of a white solid.
MS: 566/568 (M+H)+.

HPLC: Gradient elution using solvent A containing 5% solvent B increasing to 95% solvent B over 15 minutes; flow rate 1 ml/minute. Retention time: 12.90 minutes. Solvent A: H₂O/0.1% TFA; solvent B: CH₃CN/0.085% TFA. Column type: HYPERPEP 300A.

The (E)-2'-(4-bromobenzyl)-2(R)-[1(S)-[(tetrahydro-2 (RS)-pyranyloxy)carbamoyl]-4-phenyl-3-butenyl]-2'-(methanesulphonyl)-4-methylvalerohydrazide used as the starting material was prepared in an analogous manner to that described in Example 15, part (iii), starting from (E)-(2R)-[1(S)-[(tetrahydro-2(RS)-pyranyloxy)carbanoyl]-4-phenyl-3-butenyl]-2'-(methanesulphonyl)-4-methylvalerohydrazide by reaction with 4-bromobenzyl bromide.

EXAMPLE 21

(E)-2(R)-[1(S)-(Hydroxycarbamoyl)-4-phenyl-3-butenyl]-2'-(methanesulphonyl)-4-methyl-2'-(4-nitrobenzyl)valerohydrazide In an analogous manner to that described in the first paragraph of Example 2, from 0.159 g of (E)-2(R)-[1(S)-[(tetrahydro-2(RS)-pyranyloxy)carbamoyl]-4-phenyl-3-butenyl]-2-(methanesulphonyl)-4-methyl-2'-(4-nitrobenzyl) valerohydrazide there was obtained 0.085 g of (E)-2(R)-[1 (S)-(hydroxycarbamoyl)-4-phenyl-3-butenyl]-2'-(methanesulphonyl)-4-methyl-2'-nitrobenzyl) valerohydrazide in the form of a white solid.
MS: 533 (M+H)⁺.

HPLC: Gradient elution using solvent A containing 5% solvent B increasing to 95% solvent B over 15 minutes; flow rate 1 ml/minute. Retention time 12.14 minutes. Solvent A: H₂O/0.1% TFA: solvent B: CH₃CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-(methanesulphonyl)-4-methyl-2'-(4-nitrobenzyl)valerohydrazide used as the starting material was prepared in an analogous manner to that described in Example 15, part (iii), starting from (E)-(2R)-[1(S)-[(tetrahydro-2(RS)-pyranyloxy)carbamoyl]-4-phenyl-3-butenyl]-2'-(methanesulphonyl)-4-methylvalerohydrazide by reaction with 4-nitrobenzyl bromide.

EXAMPLE 22

(E)-2(R)-[1(Hydroxcarbamoyl)-4-phenyl-3-butenyl]-2'-(methanesulphonyl)-4-methyl-2'-propargylvalerohydrazide In an analogous manner to that described in the first paragraph of Example 2, starting from 0.13 g of (E)-2(R)-[1(S)-[(tetrahydro-2(RS)-pyranyloxy)carbamoyl]-4-phenyl-3-butenyl]-2'-(methanesulphonyl)-4-methyl-2'-propargylvalerohydrazide there was obtained 0.04 g of (E)-2(R)-[1(S)-(hydroxycarbamoyl)-4-phenyl-3-butenyl]-2'-(methanesulphonyl)-4-methyl-2'-propargylvalerohydrazide in the form of a white solid.
MS: 436 (M+H)⁺.

nmr (d₆ DMSO): 10.57 1H, s); 10.54 (1H, s); 8.84 (1H, br s); 7.35–7.25 (4H, m); 7.22–7.16 (1H, m); 6.30 (1H, d, J=15.5 Hz); 6.09–5.99 (1H, m); 4.32–4.17 (2H, m); 3.44 (1H, s); 3.11 (3H, s); 2.63–2.54 (1H, m); 2.41–2.17 (3H, m); 1.56–1.41 (2H, m); 1.03–0.93 (1H, m); 0.85 (3H, d, J=7.0 Hz); 0.81 (3H, d, J=6.5 Hz).

HPLC: Gradient elution using solvent A containing 40% solvent B increasing to 60% solvent B over 15 minutes; flow rate 1 ml/minute. Retention time: 11.04 minutes. Solvent A: H₂O/0.1% TFA: solvent B: CH₃CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-(methanesulphonyl)-4-methyl-2'-propargylvalerohydrazide used as the starting material was prepared in an analogous manner to that described in Example 15, part (iii), starting from (E)-(2R)-[1(S)-[(tetrahydro-2(RS)-pyranyloxy)carbamoyl]-4-phenyl-3-butenyl]-2'-(methanesulphonyl)-4-methylvalerohydrazide by reaction with propargyl bromide.

EXAMPLE 23

(E)-2'-(Cyanomethyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.18 g of (E)-2'-(cyanomethyl)-2(R)-[1(S)-[(tetrahydro-2(RS)-pyranyloxy) carbamoyl]-4-phenyl-3-butenyl]-2'-(methanesulphonyl)-4-methylvalerohydrazide there was obtained 0.124 g of (E)-2'-(cyanomethyl)-2(R)-[(S)-(hydroxycarbamoyl)-4-phenyl-3-butenyl]-2'-(methanesulphonyl)-4-methylvalerohydrazide in the form of a white solid.
MS: 437 (M+H)⁺.

nmr (d₆ DMSO): 10.94 (1H, s); 10.56 (1H, s); 8.56 (1H, br s); 7.37–7.25 (4H, m); 7.23–7.15 (1H, m); 6.33 (1H, d, J=15.5 Hz); 6.10–5.99 (1H, m); 4.65 (2H, m); 3.17 (3H, s); 2.61–2.52 (1H, m); 2.40–2.19 (3H, m); 1.55–1.41 (2H, m); 1.06–0.95 (1H, m); 0.85 (3H, d, J=7 Hz); 0.82 (3H, J=6.5 Hz).

HPLC: Gradient elution using solvent A containing 5% solvent B increasing to 95% solvent B over 15 minutes; flow rate 1 ml/minute. Retention time: 10.90 minutes. Solvent A: H₂O/0.1% TFA; solvent B: CH₃CN/0.085% TFA. Column type: HYPERPEP 300A.

The (E)-2'-(cyanomethyl)-2(R)-[1(S)-[(tetrahydro-2(RS)-pyranyloxy)carbamoyl]-4-phenyl-3-butenyl]-2'-(methanesulphonyl)-4-methylvalerohydrazide used as the starting material was prepared in an analogous manner to that described in Example 15, part (iii), starting from (E)-(2R)-[1(S)-[(tetrahydro-2(RS)-pyranyloxy)cambamoyl]-4-phenyl-3-butenyl]-2'-(methanesulphonyl)-4-methylvalerohydrazide by reaction with bromoacetonitrile.

EXAMPLE 24

(E)-2(R)-[1(S)-(Hydroxycarbamoyl)-4-phenyl-3-butenyl]-2'-(methanesulphonyl)-4-methyl-2'-(2-phenylethyl)valerohydrazide In an analogous manner to that described in the first paragraph of Example 2, starting from 0.158 g of (E)-2(R)-[1(S)-[(tetrahydro-2(RS)-pyranyloxy)carbamoyl]-4-phenyl-3-butenyl]-2'-(methanesulphonyl)-4-methyl-2'-(2-phenylethyl)valerohydrazide there was obtained 0.093 g of (E)-2(R)-[1(S)-(hydroxycarbaroyl)-4-phenyl-3-butenyl]-2'-methanesulphonyl)-4-methyl-2'-(2-phenylethyl) valerohydrazide in the form of a white solid.
MS: 502 (M+H)⁺.

HPLC: Gradient elution using solvent A containing 5% solvent B increasing to 95% solvent B over 15 minutes; flow rate 1 ml/minute. Retention time: 12.90 minutes. Solvent A: H₂O/0.1% TFA: solvent B: CH₃CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-(methanesulphonyl)-4-methyl-2'-(2-phenylethyl)valerohydrazide used as the starting material was prepared in an analogous manner to that described in Example 15, part (iii), starting from (E)-(2R)-[1(S)-[(tetrahydro-2(RS)-pyranyloxy)carbamoyl]-4-phenyl-3-butenyl]-2'-(methanesulphonyl)-4-methylvalerohydrazide by reaction with 2-bromoethyl-benzene.

EXAMPLE 25

(E)-2(R)-[1(S)-(Hydroxycarbamoyl)-4-phenyl-3-butenyl]-2'-(methanesulphonyl)-4-methyl-2'-(phthalimidomethyl)valerohydrazide In an analogous manner to that described in the first paragraph of Example 2, starting from 0.187 g of (E)-2(R)-[1(S)-[(tetrahydro-2(RS)-pyranyloxy)carbamoyl]-4-phenyl-3-butenyl]-2'-(methanesulphonyl)-4-methyl-2'-(2-phthalimidomethyl)valerohydrazide there was obtained 0.127 g of (E)-2(R)-[1(S)-(hydroxycarbamoyl)-4-phenyl-3-butenyl]-2'-(methanesulphonyl)-4-methyl-2'-(phthalimidomethyl)valerohydrazide in the form of a white solid.

MS: 557 (M+H)+ nmr ($d_6$ DMSO at 353K): 10.18 (1H, br s); 10.13 (1H, s); 8.40 (1H, br s); 7.92–7.82 (4H, m); 7.32–7.25 (4H, m); 7.22–7.15 (1H, m); 6.30 (1H, d, J=15.5 Hz); 6.06–5.96 (1H, m); 5.30 (2H, s); 3.16 (3H, s); 2.56–2.43 (1H, m); 2.40–2.21 (3H, m); 1.60–1.40 (2H, m); 1.10–0.99 (1H, m); 0.80 (3H, d, J=6.5 Hz); 0.77 (3H, d, J=7.0 Hz).

HPLC: Gradient elution using solvent A containing 5% solvent B increasing to 95% solvent B over 15 minutes; flow rate 1 ml/minute. Retention time: 12.03 minutes. Solvent A: $H_2O$/0.1% TFA: solvent B: $CH_3CN$/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-(methanesulphonyl)-4-methyl-2'-(phthalimidomethyl)valerohydrazide used as the starting material was prepared in an analogous manner to that described in Example 15, part (iii), starting from (E)-(2R)-[1(S)-{(tetrahydro-2(RS)-pyranyloxy)carbamoyl]-4-phenyl-3-butenyl]-2-(methanesulphonyl)-4-methylvalerohydrazide by reaction with N-bromomethylphthalimide.

EXAMPLE 26

(E)-2(R)-[1(S)-(Hydroxycarbamoyl)-4-phenyl-3-butenyl]-2'-(methanesulphonyl)-4-methyl-2'-(2-(phthalimidoethyl)valerohydrazide In an analogous manner to that described in the first paragraph of Example 2, starting from 0.134 g of (E)-2(R)-[1(S)-[(tetrahydro-2(RS)-pyranyloxycarbamoyl]-4-phenyl-3-butenyl]-2'-(methanesulphonyl)-4-methyl-2'-(2-(phthalimidomethyl)valerohydrazide there was obtained 0.108 g of (E)-2(R)-[1(S)-(hydroxycarbamoyl)-4-phenyl-3-butenyl]-2'-(methanesulphonyl)-4-methyl-2'-(2-phthalimidoethyl)valerohydrazide in the form of a white solid.

MS: 571 (M+H)+.

HPLC: Gradient elution using solvent A containing 5% solvent B increasing to 95% solvent B over 15 minutes; flow rate 1 ml/minute. Retention time: 12.56 minutes. Solvent A: $H_2O$/0.1% TFA; solvent B: $CH_3CN$/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-(methanesulphonyl)-4-methyl-2'-(2-phthalimidoethyl)valerohydrazide used as the starting material was prepared in an analogous manner to that described in Example 15, part (iii), starting from (E)-(2R)-[1(S)-[(tetrahydro-2(RS)-pyranyloxy)carbamoyl]-4-phenyl-3-butenyl]-2'-(methanesulphonyl)-4methylvalerohydrazide by reaction with 2-bromoethylphthalimide.

EXAMPLE 27

(E)-3-Cyclobutyl-2(R)-[1(S)-(hydroxycarbamoyl)-4-phenyl-3-butenyl]-2'-(methanesulphonyl)-2'-phenylpropionohydrazide In an analogous manner to that described in the first paragraph of Example 2, starting from 0.159 g of (E)-3-cyclobutyl-2(R)-[1(S)-[(tetrahydro-2(RS)-pyranyloxy)carbamoyl]-4-phenyl-3-butenyl]-2'-(methanesulphonyl)-2'-phenylpropionohydrazide there was obtained 0.103 g of (E)-3-cyclobutyl-2(R)-[1(S)-(hydroxycarbamoyl)-4-phenyl-3-butenyl]-2'-(methanesulphonyl)-2'-phenylpropionohydrazide in the form of an off-white solid.

MS: 486 (M+H)+.

HPLC: Gradient elution using solvent A containing 5% solvent B increasing to 95% solvent B over 15 minutes; flow rate 1 ml/minute. Retention time: 12.12 minutes. Solvent A: $H_2O$/0.1% TFA: solvent B: $CH_3CN$/0.085% TFA. Column type: HYPERPEP 300A.

The (E)-3-cyclobutyl-2(R)-[1(S)-[(tetrahydro-2(RS)-pyranyloxy)carbamoyl]-4-phenyl-3-butenyl]-2'-(methanesulphonyl)-2'-phenylpropionohydrazide used as the starting material was prepared as follows:

In an analogous manner to that described in Example 2, parts (i)–(v), starting from 4-tert-butyl hydrogen 2(R)-(cyclobutylmethyl)succinate there was obtained (E)-3-cyclobutyl-2(R)-[1(S)-[(tetrahydro-2(RS)-pyranylox)carbamoyl]-4-phenyl-3-butenyl]-2'-(methanesulphonyl)-2'-phenylpropionohydrazide in the form of a white solid.

MS: 570 (M+H)+.

EXAMPLE 28

(E)-3-Cyclopentyl-2(R)-[1(S)-(hydroxycarbamoyl)-4-phenyl-3-butenyl]-2'-(methanesulphonyl)-2'-phenylpropionohydrazide In an analogous manner to that described in the first paragraph of Example 2, starting from 0.2 g of (E)-3-cyclopentyl-2(R)-[1(S)-[(tetrahydro-2(RS)-pyranyloxy)carbamoyl]-4-phenyl-3-butenyl]-2'-(methanesulphonyl)-2'-phenylpropionohydrazide there was obtained 0.132 g of (E)-3-cyclopentyl-2(R)-[1(S)-(hydroxyarbamoyl)-4-phenyl-3-butenyl]-2'-(methanesulphonyl)-2phenylpropionohydrazide in the form of a white solid

MS: 500 (M+H)+.

HPLC: Gradient elution using solvent A containing 5% solvent B increasing to 95% solvent B over 15 minutes; flow rate 1 ml/minute. Retention time: 12.39 minutes. Solvent A: $H_2O$/0.1% TFA; solvent B: $CH_3CN$/0.085% TFA. Column type: HYPERPEP 300A.

The (E)-3-cyclopentyl-2(R)-[1(S)-[(tetrahydro-2(RS)-pyranyloxy)carbamoyl]-4-phenyl-3butenyl]-2'-(methanesulphonyl)-2-phenylpropionohydrazide used as the starting material was prepared as follows:

In an analogous manner to that described in Example 2, parts (i)–(v), starting from 4-tert-butyl hydrogen 2(R)-(cyclopentylmethyl)succinate there was obtained (E)-3-cyclopentyl-2-(R)-[1(S)-[(tetrahydro-2(RS)-pyranyloxy)carbamoyl]-4-phenyl-3-butenyl]-2'-(methanesulphonyl)-2'-phenylpropionohydrazide in the form of a white solid.

MS: 584 (M+H)+.

EXAMPLE 29

(E)-2'-(4-Bromophenyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.35 g of (E)-2'-(4-bromophenyl)-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.272 g of (E)-2'-(4-bromophenyl)-2(R)-[1(S)-(hydroxycarbamoyl)-4-phenyl-3-butenyl]-2'-(methanesulphonyl)-4-methylvalerohydrazide in the form of an off-white solid.

MS: 552 (M+H)+.

nmr (d₆ DMSO): 10.85 (1H, s); 10.31 (1H, br s); 8.48 (1H, hr s); 7.58 (2H, m); 7.32 (2H, m); 7.29 (4H, m); 7.23–7.16 (1H, m); 6.23 (1H, d, J=15.5 Hz); 6.07–5.97 (1H, m); 3.23 (3H, s); 2.60–2.50 (1H, m); 2.41–2.12 (3H, m); 1.57–1.48 (1H, m); 1.47–1.35 (1H, m); 1.16–1.06 (1H, m); 0.85 (3H, d, J=6.5 Hz); 0.78 (3H, d, J=7.0 Hz).

HPLC: Gradient elution using solvent A containing 5% solvent B increasing to 95% solvent B over 15 minutes; flow rate 1 ml/minute. Retention time: 13.41 minutes. Solvent A: H₂O/0.1% TFA; solvent B: CH₃CN/0.085% TFA.

The (E)-2'-(4-bromophenyl)-2(R)-[1(S)-[(tetrahydro-2 (RS)-pyranyloxy)carbamoyl]-4-phenyl-3-butenyl]-2'-(methanesulphonyl)-4-methylvalerohydrazide used as the starting material was prepared as follows:

In an analogous manner to that described in Example 2, parts (iii)–(v), starting from (E)-2(R)-[1(S)-(tert-butoxycarbonyl)-4-phenyl-3-butenyl]-4-methylvaleric acid and 4-bromophenylhydrazine there was obtained (E)-2'-(4-bromophenyl)-2(R)-[1(S)-[(tetrahydro-2(RS)-pyranyloxy) carbamoyl]-4-phenyl-3-butenyl]-2'-(methanesulphonyl)-4-methylvalerohydrazide in the form of a white solid.
MS: 636/638 (M +H)+.

EXAMPLE 30

(E)-2'-(tert-Butyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, from 0.35 g of (E)-2'-(tert-butyl)-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.272 g of (E)-2'(tert-butyl)-2(R)-[1(S)-(hydroxycarbamoyl)-4-phenyl-3-butenyl]-2'-(methanesulphonyl)-4-methylvalerohydrazide in the form of an off-white solid.
MS: 454 (M+H)+.

HPLC: Gradient elution using solvent A containing 10% solvent B for 5 minutes increasing to 90% solvent B from 5 minutes to 20 minutes; flow rate 1 ml/minute. Retention time: 16.56 minutes. Solvent A: H₂O/0.1% TFA: solvent B: CH₃CN/0.085% TFA. Column type: HYPERSIL 300A.

The (E)-2'-(tert-butyl)-2(R)-[1(S)-[(tetrahydro-2(RS)-pyranyloxy)carbamoyl]-4-phenyl-3-butenyl]-2'-(methanesulphonyl)-4-methylvalerohydrazide used as the starting material was prepared as follows:

In an analogous manner to that described in Example 2, parts (iii)–(v), starting from (E)-2(R)-[1(S)-(tert-butoxycarbonyl)-4phenyl-3butenyl]-4-methylvaleric acid and tert-butylhydrazine there was obtained (E)-2'-(tert-butyl)-2(R)-[1(S)-[(tetrahydro-2(RS)-pyranyloxy) carbamoyl]-4-phenyl-3-butenyl]-2'-(methanesulphonyl)-4-methylvalerohydrazide in the form of a white solid.
MS: 537 (M +H)+.

EXAMPLE 31

(E)-2'-(Cylcohexylmethyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.149 g of (E)-2'-(cyclohexylmethyl)-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.116 g of (E)-2'-(cyclohexylmethyl)-2(R)-[1(S)-(hydroxycarbamoyl)-4-phenyl-3-butenyl]-2'-(methanesulphonyl)-4-methylvalerohydrazide in the form of a white solid.
MS: 494 (M+H)+.

HPLC: Gradient elution using solvent A containing 5% solvent B increasing to 95% solvent B over 15 minutes; flow rate 1 ml/minute. Retention time: 13.67 minutes. Solvent A: H₂O/0.1% TFA; solvent B: CH₃CN/0.085% TFA. Column type: HYPERPEP 300A.

The (E)-2'-(cyclohexylmethyl)-2(R)-[1(S)-[(tetrahydro-2 (RS)-pyranyloxy)carbamoyl]-4-phenyl-3-butenyl]-2'-(methanesulphonyl)-4-methylvalerohydrazide used as the starting material was prepared in an analogous manner to that described in Example 15, part (iii), starting from (E)-(2R)-[1(S)-[(tetrahydro-2(RS)-pyranyoxy)carbamoyl]-4-phenyl-3-butenyl]-2'-(methanesulphonyl)-4-methylvalerohydrazide by reaction with cyclohexylmethyl bromide.

EXAMPLE 32

2(R)-[1(R)-(Hydroxycarbamoyl)-2-phthalimidoethyl]-2'-(methanesulphonyl)-4-methyl)-4-methyl-2'-phenylvalerohydrazide In an analogous manner to that described in the first paragraph of Example 2, starting from 0.14 g of 2(R)-[1(R)-[(tetrahyro-2(RS)-pyranyloxy)carbamoyl]-2-phthalimidoethyl]-2'-(methanesulphonyl)-4-methyl-2'-phenylvalerohydrazide there was obtained 0.092 g 2(R)-[1 (R)-(hydroxycarbamoyl)-2-phthalimidoethyl]-2'-(methanesulphonyl)-4-methyl-2'-phenylvalerohydrazide in the form of a white solid.
MS: 517 (M+H)+.

HPLC: Gradient elution using solvent A containing 10% solvent B for 5 minutes increasing to 90% solvent from 5 minutes to 20 minutes; flow rate 1 ml/minute. Retention time: 15.52 minutes. Solvent A: H₂O; solvent B: CH₃CN. Column type: HYPERPEP 300A.

The 2(R)-[1(R)-[(tetrahyro-2(RS)-pyranyloxy) carbamoyl]-2-phthalimidoethyl]-2'-(methanesulphonyl)-4-methyl-2'-phenylvalerohydrazide used as the starting material was prepared as follows:

In an analogous manner to that described in Example 2, parts (iii)–(v), starting from 2(R)-[1(R)-(tert-butoxycarbonyl)-2-phthalimidoethyl]-4-methyvaleric acid and phenylhydrazine there was obtained 2(R)-[1(R)-[(tetrahydro-2(RS)-pyranyloxy)carbamoyl]-2-phthalimidoethyl]-2'-(methanesulphonyl)-4-methyl-2'-phenylvalerohydrazide in the form of a white solid.
MS: 601 (M +H)+.

EXAMPLE 33

2(R)-[2-Benzamido-1(R)-(hydroxycarbamoyl)ethyl]-2'-(methanesulphonyl)-4-methyl-2'-phenylvalerohydrazide In an analogous manner to that described in the first paragraph of Example 2, starting from 0.084 g of 2(R)-[2-benzamido-1(R)-[(tetrahydro-2(RS)-pyranyloxy) carbamoyl]ethyl]-2'-(methanesulphonyl)-4-methyl-2'-phenylvalerohydrazide there was obtained 0.055 g of 2(R)-[2-benzamido-1(R)-(hydroxycarbamoyl)ethyl]-2'-(methanesulphonyl)-4-methyl-2'-phenylvalerohydrazide in the form of a white solid.
MS: 491 (M+H)+.

HPLC: Gradient elution using solvent A containing 5% solvent B for 5 minutes increasing to 95% solvent B from 5 minutes to 20 minutes; flow rate 1 ml/minute. Retention time: 15.54 minutes. Solvent A: H$_2$O/0.1% TFA; solvent B: CH$_3$CN/0.085% TFA. Column type: HYPERPEP 300A.

The 2(R)-[2-benzamido-1(R)-[(tetrahydro-2(RS)-pyranyloxy)carbamoyl]ethyl]-2'-(methanesulphonyl)-4-methyl-2'-phenylvalerohydrazide used as the starting material was prepared as follows:

(i) A solution of 0.705 g of 2(R)-[1(R)-(tert-butoxycarbonyl)-2-phthalimidoethyl]-2'-(methanesulphonyl)-4-methyl-2'-phenylvalerohydrazide in 15 ml of methanol was treated with 0.51 ml of hydrazine hydrate. The mixture was stirred under nitrogen overnight and then evaporated. The residue was stirred with 25 ml of dichloromethane/methanol/acetic acid/water (120:15:3:2). After 2 hours the precipitated solid was removed by filtration and the filtrate was evaporated. The residue was purified by chromatography on Kieselgel 60 using dichlormethane/methanol/acetic acid/water (240:24:3:2) for the elution. Fractions containing the amine product were combined and evaporated, and the residue was dissolved in 30 ml of dichloromethane and washed with three 10 ml portions of saturated sodium hydrogen carbonate solution. After drying over anhydrous magnesium sulphate the solution was evaporated to give 0.42 g of 2(R)-[2-amino-1(R)-(tert-butoxycarbonyl)ethyl]-2'-(methanesulphonyl)-4methyl-4-methyl-2'-phenylvalerohydrazide in the form of a pale yellow foam.

MS: 428 (M+H)$^+$.

(ii) A mixture of 0.42 g of the amine prepared in part (i) and 0.138 g of benzoic acid in 7 ml of dimethylformamide was cooled to 0° C. while stirring and 0.335 g of 1-ethyl-3-(3-dimethylaminopropyl)carbodiimide was added. The mixture was left to come to room temperature and was stirred overnight. The solvent was evaporated and the residue was partitioned between ethyl acetate and saturated sodium hydrogen carbonate solution. The ethyl acetate layer was washed in succession with saturated sodium hydrogen carbonate solution, 5% citric acid solution, water and saturated sodium chloride solution and then dried over anhydrous magnesium sulphate. The ethyl acetate was evaporated and the residue was triturated with a mixture of ether and hexane to give 0.331 g of 2(R)-[2-benzamido-1(R)-(tert-butoxycarbonyl)ethyl]-2'-(methanesulphonyl)-4-methyl-2'-phenylvalerohydrazide in the form of an off-white solid.

MS: 532 (M+H)$^+$.

(iii) In an analogous manner to that described in Example 2, parts (iii)–(v), starting from 2(R)-[2-benzamido-1(R)-(tert-butoxycarbonyl)ethyl]-2'-(methanesulphonyl)-4-methyl-2'-phenylvalerohydrazide there was obtained 2(R)-[2-benzamido-2(R)-[(tetrahydro-2(RS)-pyranyloxy)carbamoyl]ethyl]-2'-(methanesulphonyl)-4-methyl-2'-phenylvalerohydrazide in the form of a white solid

MS: 575 (M+H)$^+$.

EXAMPLE 34

2(R)-[2-[(5-Bromo-2-furyl)carboxamido]-1(R)-(hydroxycarbamoyl)ethyl]-2'-(methanesulphonyl)-4-methyl-2'-phenylvalerohydrazide In an analogous manner to that described in the first paragraph of Example 2, starting from 0.195 g of 2(R)-[2-[(5-bromo-2-furyl)carboxamido]-1(R)-[(tetrahydro-2(RS)-pyranyloxy)carbamoyl]ethyl]-2'-(methanesulphonyl)-4-methyl-2'-phenylvalerohydrazide there was obtained 0.127 g of 2(R)-[2-[(5-bromo-2-furyl)carboxamido]-1(R)-(hydroxycarbamoyl)ethyl]-2'-(methanesulphonyl)-4-methyl-2'-phenylvalerohydrazide in the form of a cream coloured solid.

MS: 560 (M+H)$^+$.

HPLC: Gradient elution using solvent A containing 5% solvent B increasing to 95% solvent B over 15 minutes; flow rate 1 ml/minute. Retention time: 10.69 minutes. Solvent AA H$_2$O/0.1% TFA; solvent B: CH$_3$CN/0.085% TFA. Column type: HYPERPEP 300A.

The 2(R)-[2-[(5-bromo-2-furyl)carboxamido]-1(R)-[(tetrahydro-2(RS)-pyranyloxy)carbamoyl]ethyl]-2'-(methanesulphonyl)-4-methyl-2'-phenylvalerohydrazide used as the starting material was prepared as follows:

In an analogous manner to that described in Example 33, parts (ii) and (iii), starting from 2(R)-[2-amino-(R)-(tert-butoxycarbonyl)ethyl]-2'-(methanesulphonyl)-4-methyl-2'-phenylvalerohydrazide and 5-bromo-2-furoic acid there was obtained 2(R)-[2-[(5-bromo-2-furyl)carboxamido]-1(R)-[(tetrahydro-2(RS)-pyranyloxy)carbonyl]ethyl]-2'-(methanesulphonyl)-4-methyl-2'-phenylvalerohydrazide in the form of an off-white solid.

MS: 644 (M+H)$^+$.

EXAMPLE 35

2(R)-1(R)-(Hydroxycarbamoyl)-2-[(2-thiazoly)carboxamido]ethyl-2'-(methanesulphony)-4-methyl-2'-phenylvalerohydrazide In an analogous manner to that described in the first paragraph of Example 2, starting from 0.1 g of 2(R)-[1(R)-[(tetrahydro-2(RS)-pyranyloxy)carbamoyl]-2-[(2-thiazolyl)carboxamdo]ethyl]-2'-(methanesulphonyl)-4-methyl-2'-phenylvalerohydrazide there was obtained 0.041 g of 2(R)-[1(R)-(hydroxycarbamoyl)-2-[(2-thiazolyl)carboxamido]ethyl]-2'-(methanesulphonyl)-4-methyl-2'-phenylvalerohydrazide in the form of a off-white solid.

MS: 498 (M+H)$^+$.

HPLC: Gradient elution using solvent A containing 5% solvent B increasing to 95% solvent B over 15 minutes; flow rate 1 ml/minute. Retention time: 10.14 minutes. Solvent A: H$_2$O/0.1% TFA; solvent B: CH$_3$CN/0.085% TFA. Column type: HYPERPEP 300A.

The 2(R)-[1(R)-[(tetrahydro-2(RS)-pyranyloxy)carbamoyl]-2-[(2-thiazolyl)carboxamido]ethyl]-2'-(methanesulphonyl)-4-methyl-2'-phenylvalerohydrazide used as the starting material was prepared as follows:

In an analogous manner to that described in Example 33, parts (ii) and (iii), starting from 2(R)-[2-amino-1(R)-(tert-butoxycarbonyl)ethyl]-2'-(methanesulphonyl)-4-methyl-2'-phenylvalerohydrazide and 2-thiazolecarboxylic acid there was obtained 2(R)-[1(R)-[(tetrahydro-2(RS)-pyranyloxy)carbamoyl]-2-[(2-thiazoyl)carboxamido]ethyl]-4-methyl-2'-phenylvalerohydrazide in the form of a white solid.

MS: 582 (M+H)$^+$.

EXAMPLE 36

2(R)-[1(R)-(Hydroxycarbamoyl)-2-[(2-thienyl)carboxamido]ethyl]-2'-(methanesulphonyl)-4-methyl-2'-phenylvalerohydrazide In an analogous manner to that described in the first paragraph of Example 2, starting from 0.2 g of 2(R)-[1(R)-[(tetrahydro-2(RS)-pyranyloxy)carbamoyl]-2-[(2-thienyl)

carboxamido]ethyl]-2'-(methanesulphonyl)-4-methyl-2'-phenylvalerohydrazide there was obtained 0.115 g of 2(R)-[1(R)-(hydroxycarbamoyl)-2'-[(2-thienyl)carboxamido]ethyl]-2'-(methanesulphonyl)-4-methyl-2'-phenylvalerohydrazide in the form of a white solid.
MS: 497 (M+H)$^+$.

HPLC: Gradient elution using solvent A containing 5% solvent B increasing to 95% solvent B over 15 minutes; flow rate 1 ml/minute. Retention time: 10.39 minutes. Solvent A: H$_2$O/0.1% TFA; solvent B: CH$_3$CN/0.085% TFA. Column type: HYPERPEP 300A.

The 2(R)-[1(R)-[(tetrahydro-2(RS)-pyranyloxy)carbamoyl]-2-[(2-thienyl)carboxamidoethyl]-2'-(methanesulphonyl)-4-2-phenylvalerohydrazide used as the starting material was prepared as follows:

In an analogous manner to that described in Example 33, parts (ii) and (iii), starting from 2(R)-[2-amino-1(R)-(tert-butoxycarbonyl)ethyl]-2'-(methanesulphonyl)-4-methyl-2'-phenylvalerohydrazide and thiophene-2-carboxylic acid there was obtained 2(R)-[1(R)-[(tetrahydro-2(RS)-pyranyloxy)-carbamoyl]-2-[(2'-(methanesulphonyl)-4-methyl-2'-phenylvalerohydrazide in the form of a white solid.
MS: 581 (M+H)$^+$.

EXAMPLE 37

2(R)-[1(R)-(Hydroxycarbamoyl)-2-(3-phenylureido)ethyl]-2'-(methanesulphonyl)-4-methyl-2'-phenylvalerohydrazide In an analogous manner to that described in the first paragraph of Example 2, starting from 0.157 g of 2(R)-[1(R)-[(tetrahydro-2(RS)-pyranyloxy)carbamoyl]-2-(3-phenylureido)ethyl]-2'-(methanesulphonyl)-4-methyl-2'-phenylvalerohydrazide there was obtained 0.072 g of 2(R)-[1(R)-(hydroxycarbamoyl)-2-(3-phenylureido)ethyl]-2-(3-phenylureido)ethyl]-2-'(methanesulphonyl)-4-methyl-2 -phenylvalerohydrazide in the form of a white solid.
MS: 507 (M+H)$^+$.

HPLC: Gradient elution using solvent A containing 5% solvent B increasing to 95% solvent B over 15 minutes; flow rate 1 ml/minute. Retention time 10.91 minutes. Solvent A: H$_2$O/0.1% TFA; solvent B: CH$_3$CN/0.085% TFA. Column type: HYPERPEP 300A.

The 2(R)-[1(R)-[(tetrahydro-2(RS)-pyranyloxy)carbamoyl]-2-(3-phenylureido)ethyl]-2'-(methanesulphonyl)-4-methyl-2'-phenylvalerohydrazide used as the starting material was prepared as follows:

(i) A mixture of 0.8 g of 2(R)-[2-amino-1(R)-(tert-butoxycarbonyl)ethyl]-2'-(methanesulphonyl)-4-methyl-2'-phenylvalerohydrazide prepared as described in Example 33, part (i), 0.325 ml of N,N-diisopropylethylamine and 0.21 ml of phenyl isocyanate in 10 ml of dimethylformamide was stirred at 60° C. under nitrogen for 2.5 hours. The solvent was evaporated and the residue was partitioned between ethyl acetate and 1M hydrochloric acid. The ethyl acetate solution was separated and washed with sodium hydrogen carbonate solution and with saturated sodium chloride solution, dried over anhydrous magnesium sulphate and evaporated. The residue was triturated with diethyl ether and there was obtained 0.705 g of 2(R)-[1(R)-(tert-butoxycarbonyl)-2-(3-phenylureido)ethyl]-2'-(methanesulphonyl)-4-methyl-2'-phenylvalerohydrazide in the form of a white solid.
MS: 547 (M+H)$^+$.

(ii) In an analogous manner to that described in Example 2, parts (iii)–(v), starting from the hydrazide prepared in the preceding paragraph there was obtained 2(R)-[1(R)-[(tetrahydro-2-(RS)-pyranyloxy)-carbamoyl]-2-(3-phenylureido)ethyl]-2'-(methanesulphonyl)-4-methyl-2'-phenylvalerohydrazide in the form of a white solid.
MS: 590 (M+H)$^+$.

EXAMPLE 38

2(R)-[1(R)-(Hydroxycarbamoyl)-2-[(2-thienyl)sulphonamido]ethyl]-2'-(methanesulphonyl)-4-methyl-2'-phenylvalerohydrazide In an analogous manner to that described in the first paragraph of Example 2, starting from 0.28 g of 2(R)-[1(R)-[(tetrahydro-2(RS)-pyranyloxy)carbamoyl]-2-[(2-thienyl)sulphonamido]ethyl]-2'-(methanesulphonyl)-4-methyl-2'-phenylvalerohydrazide there was obtained 0.066 g of 2(R)-[1(R)-(hydroxycarbamoyl)-2-[(2-thienyl)sulphonamido]ethyl]-2'-(methanesulphonyl)-4-methyl-2'-phenylvalerohydrazide in the form of a white solid.
MS: 533 (M+H)$^+$.

HPLC: Gradient elution using solvent A containing 5% solvent B increasing to 95% solvent B over 15 minutes; flow rate 1 ml/minute. Retention time: 10.65 minutes. Solvent A: H$_2$O/0.1% TFA; solvent B: CH$_3$CN/0.085% TFA. Column type: HYPERPEP 300A.

The 2(R)-[1(R)-[(tetrahydro-2(RS)-pyranyloxy)carbamoyl]-2-[(2-thienyl)sulphonamido]ethyl]-2'-(methanesulphonyl)-4-methyl-2'-phenylvalerohydrazide used as the starting material was prepared as follows:

(i) A solution of 0.504 g of 2(R)-[2-amino-1(R)-(tert-butoxycarbonyl)ethyl]-2'-(methanesulphonyl)-4-methyl-2'-phenylvalerohydrazide in 20 ml of dichloromethane was cooled to 0° C. while stirring and 0.242 g of 2-thiophenesulphonyl chloride was added. The mixture was left to come to room temperature and was stirred overnight. The solvent was evaporated and the residue was partitioned between ethyl acetate and 5% aqueous citric acid solution. The ethyl acetate layer was washed with saturated sodium hydrogen carbonate solution and then with saturated sodium chloride solution, dried over anhydrous magnesium sulphate and evaporated. The residue was triturated with ether and there was obtained 0.487 g of 2(R)-[1(R)-(tert-butoxycarbonyl)-2-[(2-thienyl)sulphonamido]ethyl]-2'-(methanesulphonyl)-4-methyl-2'-phenylvalerohydrazide in the form of a white solid.
MS: 574 (M+H)$^+$.

(ii) In an analogous manner to that described in Example 2, parts (iii)–(v), starting from the hydrazide prepared in the preceding paragraph there was obtained 2(R)-[1(R)-[(tetrahydro-2(RS)-pyranyloxy)-carbamoyl]-2-[(2-thienyl)suophonamido]ethyl]-2'-(methanesulphonyl)-4-methyl-2'-phenylvalerohydrazide in the form of a white solid.
MS: 581 (M+H)$^+$.

EXAMPLE 39

(E)-2'-(Benzylsulphonyl)-2(R)-[1(S)-(hydroxycarbamoyl)-4-phenyl-3-butenyl]-4-methyl-2'-phenylvalerhydrazide In an analogous manner to that described in the first paragraph of Example 2, starting from 0.1 g of (E)-2'-(benzylsulphonyl)-2(R)-[1(S)-[(tetrahydro-2(RS)-pyranyloxy)carbamoyl]-4-phenyl-3-butenyl]-4-methyl-2'-phenylvalerohydrazide there was obtained 0.051 g of (E)-

2'-(benzylsulphonyl)-2(R)-[1(S)-(hydroxycarbamoyl)-4-phenyl-3-butenyl-]4-methyl-2'-phenylvalerohydrazide in the form of a white solid.
MS: 550 (M+H)+.

HPLC: Gradient elution using solvent A containing 5% solvent B increasing to 95% solvent B over 15 minutes; flow rate 1 ml/minute. Retention time: 13.62 minutes. Solvent A: H₂O/0.1% TFA; solvent B: CH₃CN/0.085% TFA. Column type: HYPERPEP 300A.

The (E)-2'-(benzylsulphonyl)-2(R)-[1(S)-[(tetrahydro-2(RS)-pyranyloxy)carbamoyl]-4-phenyl-3-butenyl]-4-methyl-2'-phenylvalerohydrazide used as the starting material was prepared as follows:

(i) In an analogous manner to that described in Example 1, part (ii), starting from 0.3 g of (E)-2(R)-[1(S)-(tert-butoxycarbonyl)-4-phenyl-3-butenyl]-4-methyl-2'-phenylvalerohydrazide and 0.543 g of benzylsulphonyl chloride there was obtained 0.316 g of (E)-2'-(benzylsulphonyl)-2(R)-[1(S)-(tert-butoxycarbonyl)-4-phenyl-3-butenyl]-4-methyl-2'-phenylvalerohydrazide in the form of a white solid.
MS: 591 (M+H)+.

(i) In an analogous manner to that described in Example 1, part (iii), and Example 2, part (v), from the hydrazide prepared in the preceding paragraph there was obtained (E)-2-(benzylsulphonyl)-2(R)-[1(S)-[(tetrahydro-2(RS)-pyranyloxy)carbonyl]-4-phenyl-3-butenyl]-4-methyl-2'-phenylvalerohydrazide in the form of a white solid.
MS: 634 (M+H)+.

EXAMPLE 40

(E)-2(R)-[1(S)-(Hydroxycarbamoyl)-4-phenyl-3-butenyl]-2'-(methanesulphonyl)-3-methyl-2'-phenylbutylhydrazide In an analogous manner to that described in the first paragraph of Example 2, starting from 0.098 g of (E)-2(R)-[1(S)-[(tetrahydro-2(RS)-pyranyloxy)carbamoyl]-4-phenyl-3-butenyl]-2'-(methanesulphonyl)-3methyl-2'-phenylbuthydrazide there was obtained 0.054 g of (E)-2(R)-[1(S)-(hydroxycarbamoyl)-4-phenyl-3-butenyl]-2'-(methanesulphonyl)-3-methyl-2'-phenylbuthydrazide in the form of an off-white solid.
MS: 460 (M+H)+.

HPLC: Gradient elution using solvent A containing 5% solvent B increasing to 95% solvent B over 15 minutes; flow rate 1 ml/minute. Retention time: 11.72 minutes. Solvent A: H₂O/0.1% TFA; solvent B: CH₃CN/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-(methanesulphonyl)-3-methyl-2'-phenylbutylhydrazide used as the starting material was prepared as follows:

In an analogous manner to that described in Example 2, parts (i)–(v), starting from 4-tert-butyl hydrogen 2(R)-isopropylsuccinate there was obtained (E)-2(R)-[1(S)-[(tetrahydro-2(RS)-pyranyloxy)-carbaroyl]-4-phenyl-3-butenyl]-2'-(methanesulphonyl)-3methyl-2'-phenylbuthydrazide in the form of a white solid.
MS: 544 (M+H)+.

EXAMPLE 41

(E)-2'-Acetyl-2(R)-[1(S)-(hydroxycarbamoyl)-4-phenyl-3-butenyl]-4-methyl-2'-phenylvalerohydrazide In a manner analogous to that described in the first paragraph of Example 2, starting from 0.23 g of (E)-2'-acetyl-2(R)-[1(S)-[(tetrahydro-2(RS)-pyranyloxy)carbamoyl]-4-phenyl-3-butenyl]-4-4-methyl-2'-phenylvalerohydrazide there was obtained 0.09 g of (E)-2'-acetyl-2(R)-[1(S)-(hydroxycarbamoyl)-4-phenyl-3-butenyl]-4-methyl-2'-phenylvalerohydrazide in the form of a white solid.
MS: 438 (M+H)+.

HPLC: Gradient elution using solvent A containing 5% solvent B increasing to 95% solvent B over 15 minutes; flow rate 1 ml/minute. Retention time: 11.29 minutes. Solvent A: H₂O/0.1% TFA; solvent B: CH₃CN/0.085% TFA. Column type: HYPERPEP 300A.

The (E)-2'-acetyl-2(R)-[1(S)-[(tetrahydro-2(RS)-pyranyloxy)carbamoyl]-4-phenyl-3-butenyl]-4-methyl-2'-phenylvalerohydrazide used as the starting material was prepared in a manner analogous to that described in Example 4, parts i)–ii), starting from (E)-2(R)-[1(R)-(tert-butoxycarbonyl)-4-phenyl-3-butenyl]-4-methylvaleric acid prepared as described in Example 2, part (i).

EXAMPLE 42

(E)-2'-(Ethylcarbamoyl)-2(R)-[1(S)-(hydroxycarbamoyl)-4-phenyl-3-butenyl]-4-methyl-2'-phenylvalerohydrazide A solution of 0.190 g of (E)-2'-(ethylcarbamoyl)-2(R)-[1(S)-[(tetrahydro-2(RS)-pyranyloxy)carbamoyl]-4-pyranyloxy)-carbamoyl]-4-phenyl-3-butenyl]-4-methyl-2'-phenylvalerohydrazide in a mixture of 2 ml of dichloromethane and 0.5 ml of methanol was treated with 9 ml of methanesulphonic acid. The mixture was stirred for 2 hours at room temperature and the solvent was evaporated. The residue was triturated with 5% sodium hydrogen carbonate solution and dissolved in diethyl ether. The solution was dried over magnesium sulphate and evaporated to a gum. Chromatography on silica gel using dichloromethane/methanol (19:1) for the elution yielded 0.02 g of (E)-2'-(ethylcarbamoyl)-2(R)-[1(S)-(hydroxycarbamoyl)-4-phenyl-3-butenyl]-4-methyl-2'-phenylvalerohydrazide as a white solid.
MS: 467 (M+H)+.

HPLC: Gradient elution using solvent A containing 40% solvent B increasing to 60% solvent B over 15 minutes; flow rate 1 ml per minute. Retention time: 11.80 minutes. Solvent A: H₂O/0.1% TFA; solvent B: CH₃CN/0.085% TFA. Column type: HYPERPEP 300A.

The (E)-2'-(ethylcarbamoyl)-2(R)-[1(S)-[(tetrahydro-2(RS)-pyranyloxy)carbamoyl]-4-phenyl-3-butenyl]-4-methyl-2'-phenylvalerohydrazide used as the starting material was prepared as follows:

(i) 0.8 g of (E)-2(R)-[1(S)-tert-butoxycarbonyl-4-phenyl-3-butenyl]-4-methyl-2'-phenylvalerohydrazide, prepared as described in Example 2, part (iii), in 8 ml of dry dichloromethane was heated at 0° C. under nitrogen with 0.88 ml of ethyl isocyanate and the mixture was stirred overnight at room temperature and then evaporated to a gum. Chromatography on silica gel using hexane/ethyl acetate (2:1) for the elution yielded 0.65 g of (E)-2'-(ethylcarbamoyl)-2(R)-[1(S)-(tert-butoxycarbamoyl)-4-phenyl-3-butenyl]4-methyl-2'-phenylvalerohydrazide as a white foam.

(ii) 0.64 g of the tert-butyl ester prepared according to part (i) was treated with a solution of 50% trifluoroacetic acid in dichloromethane for 3 hours at room temperature and evaporated. Toluene was added twice and evaporated each time. The residue was purified by chromatography on silica gel using dichloromethane/ methanol (19:1) for the elution to yield 0.36 g of (E)-2'-(ethylcarbamoyl)-2(R)-[1(S)-carboxy-4-phenyl-3-butenyl]-4-methyl-2'-phenylvalerohydrazide as a glass.

(iii) 0.35 g of the carboxylic acid prepared according to part (ii) was dissolved in 3 ml of dimethylformamide, cooled to 0° C. and treated with 0.26 g of O-(tetrahydro-2H-pyran-2(RS)-yl)hydroxylamine and 0.215 g of 1-ethyl-3-(3-dimethylaminopropyl) carbodiimide hydrochloride. The mixture was stirred overnight at room temperature and then poured into water. The solid was removed by filtration and washed in sequence with 2M hydrochloric acid solution, water, 5% sodium hydrogen carbonate solution and water and then dried in vacuo. Chromatography on silica gel using hexane/ethyl acetate (1:1) for the elution yielded 0.2 g of (E)-2'-(ethylcarbamoyl)-2(R)-[1(S)-[(tetrahydro-2(RS)-pyranyloxy)-carbamoyl]-4-phenyl-3-butenyl]-4-methyl-2'-phenylvalerohydrazide as a white foam.
MS: 551 (M+H)+.

EXAMPLE 43

(E)-2'-(Benzylcarbamoyl)-2(R)-[1(S)-(hydroxycarbamoyl]-4-phenyl-3-butenyl]-4-methyl-2'-phenylvalerohydrazide 0.17 g of (E)-2'-(benzylcarbamoyl)-2(R)-[1(S)-{(O-tert-butyldimethylsilyl)hydroxycarbamoyl}-4-phenyl-3-butenyl]-4-methyl-2'-phenylvalerohydrazide was stirred in 5 ml of acetic acid/water/tetrahydrofuran (3:1:1) for 1.5 hours at room temperature. The solvent was evaporated and the residue was triturated with diethyl ether to give 0.03 g of (E)-2'-(benzylcarbamoyl)-2(R)-[1(S)-(hydroxycarbamoyl)-4-phenyl-3-butenyl]-4-methyl-2'-phenylvalerohydrazide as a white solid. tlc: dichloromethane/methanol (3:1) Rf=0.43. MS: 529 (M+H)+.

HPLC: Gradient elution using solvent A containing 5% solvent B increasing to 95% solvent B over 15 minutes; flow rate 1 ml/minute. Retention time: 13.14 minutes. Solvent A: H$_2$O/0.1% TFA; solvent B: CH$_3$CN/0.085% TFA. Column type: HYPERPEP 300A.

The (E)-2'-(benzylcarbamoyl)-2(R)-[1(S)-{(O-tert-butyldimethylsilyl)hydroxycarbamoyl}-4-phenyl-3-butenyl]-4-methyl-2'-phenylvalerohydrazide used as the starting material was prepared as follows:

(E)-2'-(Benzylcarbamoyl)-2(R)-[1(S)-carboxy-4-phenyl-3-butenyl]-4-methyl-2'-phenylvalerohydrazide was prepared in a manner analogous to that described in Example 42 (i)–(ii).

0.72 g of the carboxylic acid prepared in the preceding paragraph was dissolved in 2 ml of dimethylformamide cooled to 0° C. and treated with 1.0 g of O-(tert-butyldimethylsilyl)hydroxylamine, 0.2 ml of N-ethylmorpholine and 0.3 g of 1-ethyl-3-(3-dimethylaminopropyl)carbodiimide hydrochloride. The mixture was stirred at room temperature overnight and evaporated. The residue was taken up in dichloromethane, washed in sequence with 5% sodium hydrogen carbonate solution, water, 2M hydrochloric acid, water, 5% sodium hydrogen carbonate solution and saturated sodium chloride solution, dried over magnesium sulphate and evaporated to give a brown semi-solid mass. Chromatography on silica gel using dichloromethane/methanol (33:1) for the elution followed by trituration with ethylhexane yielded 0.19 g of (E)-2'-(benzylcarbamoyl)-2(R)-[1(S)-{(O-tert-butyldimethylsilyl)hydroxycarbarnoyl}-4-phenyl-3-butenyl]-4-methyl-2'-phenylvalerohydrazide as a solid. tlc: dichloromethane/methanol (9:10): Rf=0.65.

EXAMPLE 44

(E)-2'-Cyclohexyl-2(R)-[1(S)-(hydroxycarbamoyl)-4-phenyl-3-butenyl]-2'-(methanesulphonyl)-4-methylvalerohydrazide 0.09 g of (E)-2'-cyclohexyl-2(R)-[1(S)-({O-4-methoxybenzyl}hydroxycarbamoyl)-4-phenyl-3-butenyl]-2'-(methanesulphonyl)-4-methylvalerohydrazide was dissolved in a mixture of 2.5 ml of dichloromethane, 0.35 ml trifluoroacetic acid and 0.1 ml of anisole at 0° C. The mixture was stirred for 6 hours at room temperature, held at 4° C. overnight and then evaporated. 10 ml of toluene were added twice and the mixture was evaporated each time. Trituration of the residue with diethyl ether yielded 0.06 g of (E)-2'-cyclohexyl-2(R)-[1(S)-(hydroxycarbamoyl)-4-phenyl-3-butenyl]-2'-(methanesulphonyl)-4-methylvalerohydrazide as a white solid.
MS: 480 (M+H)+.

HPLC: Gradient elution using solvent A containing 5% solvent B increasing to 95% solvent B over 15 minutes; flow rate 1 ml per minute. Retention time: 12.39 minutes. Solvent A: H$_2$O/0.1% TFA; solvent B: CH$_3$CN/0.085% TFA. Column type: HYPERPEP 300A.

The (E)-2'-cyclohexyl-2(R)-[1(S)-({O-4-methoxybenzyl}hydroxycarbamoyl)-4-phenyl-3-butenyl]-2'-(methanesulphonyl)-4-methylvalerohydrazide used as the starting material was prepared as follows:

(i) A solution of 10 g of (E)-2(R)-[1(S)-(tert-butoxycarbonyl)-4-phenyl-3-butenyl]-4-methylvaleric acid in 100 ml of dichloromethane was treated at 0° C. with 0.61 g of 4-dimethylaminopyridine, 6.1 g of 1-ethyl-3-(3-dimethylaminopropyl)carbodiimide and 2.4 ml of methanol. The mixture was stirred at 0° C. for 1 hour, left to warm to room temperature, stirred for a further 3 hours and then evaporated. The residue in diethyl ether was washed in sequence with 2M hydrochloric acid, water and 5% sodium hydrogen carbonate solution, dried over magnesium sulphate and evaporated to a brown oil. Chromatography on silica gel using hexane/diethyl ether (9:1) for the elution followed by evaporation yielded 6.9 g of the diester. This was dissolved in a mixture of 45 ml of dichloromethane and 45 ml of trifluoroacetic acid and the solution was stirred for 2 hours and then evaporated. Traces of trifluoroacetic acid were removed by the addition and evaporation of toluene (2×30 ml) and the product was dried in vacuo to give the succinimate monomethyl ester as a fawn coloured solid.

(ii) 2.0 g of the foregoing succinate monomethyl ester were dissolved in 20 ml of dimethylformamide and the solution was cooled to 0° C. 1.06 g of hydroxybenzotriazole hydrate, 1.5 g of 1-ethyl-3-(3-dimethylaminopropyl)-cabodiimide hydrochloride, 1.7 ml of N-ethylmorpholine and 1.5 g of O-(4-methoxybenzyl)hydroxylamine were added. The mixture was stirred for 0.5 hour at 5° C. and for 2.5 hours at room temperature and then evaporated under a high vacuum. The residue in ethyl acetate was washed in sequence with 5% sodium hydrogen carbonate solution, 2M hydrochloric acid, water, 5% sodium hydrogen carbonate and saturated sodium chloride solution, dried over magnesium sulphate and evaporated to a solid. Chromatography on silica gel using ethyl acetate/hexane (1:4) for the elution yielded 1.83 g of methyl (E)-2(R)-[1(S)-({O-(4-methoxybenzyl}hydroxyarbamoyl)-4-phenyl-3butenyl]-4-methylvalerate as an oil, which solidified on standing to give a white solid.

MS: 440 (M+H)+.

(iii) 3.45 ml of a solution of trimethylaluminium (2M in hexane) were added dropwise to a suspension of 1.03 g of cyclohexylhydrazine in 5 ml of dichloromethane under nitrogen. A vigorous evolution of gas was observed and the solid dissolved gradually over 1 hour to give solution A.

(iv) 0.44 g of the methyl ester prepared according to (ii) was dissolved in 4 ml of dichloromethane, solution A was added and the mixture was warmed in a water bath for 6 hours (bath temperature 45° C.). The solution was cooled, treated very carefully with an excess of 2M hydrochloric acid (vigorous gas evolution) and then extracted twice with 20 ml of ethyl acetate each time. The organic phase was washed in sequence with 5% sodium hydrogen carbonate solution, water and saturated sodium chloride solution, dried over magnesium sulphate and evaporated to give a yellow gum. Chromatography on silica gel using dichloromethane/methanol (24:1) for the elution yielded 0.19 g of the hydrazide.

(MS: 522 (M+H)+.

(v) 0.11 g of the hydrazide prepared according to (iv) was suspended in a mixture of 5 ml of dichloromethane and 0.026 ml of pyridine under nitrogen. 0.046 g of methanesulphonic anhydride was added and the mixture was stirred for 3 hours at room temperature and then diluted with 15 ml of dichloromethane. The solution was washed in sequence with 2M hydrochloric acid, water and 5% sodium hydrogen carbonate solution, dried over magnesium sulphate and evaporated to give a white foam. Trituration with diethyl ether yielded 0.095 g of (E)-2'-cyclohexyl-2(R)-[1(S)-({O-4-methoxybenzyl}hydroxycarbamoyl)-4-phenyl-3-butenyl]-2'-(methanesulphonyl)-4-methylvalerohydrazide as a white solid. MS: 600 (M+H)+.

EXAMPLE 45

(E)-2(R)-[1(S)-(Hydroxycarbamoyl)-4-phenyl-3-butenyl]-2'-isobutyl-2'-(methanesulphonyl)-4-methylvalerohydrazide A solution of 0.246 g of (E)-2(R)-[1(S)-[(tetrahydro-2 (RS)-pyranyloxy)carbamoyl]-4-phenyl-3-butenyl]-2'-(methanesulphonyl)-4-methylvalerohydrazide in a mixture of 10 ml of methanol and 2 ml of dichloromethane was treated with 0.006 ml of methanesulphonic acid. The mixture was stirred for 3 hours at room temperature and then the solvent was evaporated. The residue was partitioned between ethyl acetate and water. The ethyl acetate layer was dried over anhydrous magnesium sulphate and the solvent evaporated. The residue was triturated with hexane to give 0.119 g of (E)-2(R)-[1(S)-(hydroxycarbamoyl)-4-phenyl-3-butenyl]-2'-isobutyl-2'-(methanesulphonyl)-4-methylvalerohydrazide in the form of a white solid.

MS: 454 (M+H)+.

HPLC: Gradient elution using solvent A containing 5% solvent B increasing to 95% solvent B over 15 minutes; flow rate 1 ml/minute. Retention time: 12.17 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-2'-(methanesulphonyl)-4-methylvalerohydrazide used as the starting material was prepared as follows:

(i) A solution of 0.60 g of (E)-2(R)-[1(S)-(tert-butoxycarbonyl)-4-phenyl-3-butenyl]-4-methylvalerohydrazide, 0.166 ml isobutyraldehyde and a crystal of 4-toluenesulphonic acid in 10 ml of dichloromethane was stirred for 1 hour over 4 Å molecular sieves. The mixture was filtered and the solvent was evaporated and replaced with 10 ml of methanol. A few crystals of bromocresol green were added to give a yellow solution. To this was added 0.116 g of sodium cyanoborohydride in small batches. The yellow colour of the solution was maintained by the periodic addition of a 4M solution of hydrogen chloride in dioxane. The methanol was evaporated and the residue was partitioned between dichloromethane and 5% aqueous sodium hydrogen carbonate solution. The aqueous layer was washed twice with dichloromethane and then the combined organic layers were washed twice with 5% aqueous sodium hydrogen carbonate solution. The dichloromethane layer was dried over anhydrous magnesium sulphate and the solvent was evaporated. The residue was purified by flash chromatography on silica gel using hexane/ethyl acetate (7:3) for the elution. There was obtained 0.312 g of (E)-2(R)-[1(S)-(tert-butoxycarbonyl)-4-phenyl-3-butenyl]-2'-isobutyl-2'-(methanesulphonyl)-4-methylvalerohydrazide in the form of a white solid.

MS: 417 (M+H)+.

(ii) In an analogous manner to that described in Example 2, parts (iv) and (v), starting from 0.435 g of (E)-2(R)-[1(S)-(tert-butoxycarbonyl)-4-phenyl-3-butenyl]-2'-isobutyl-4-methylvalerohydrazide there was obtained 0.249 g of (E)-2(R)-[1(S)-[(tetrahydro-2(RS)-pyranyloxy)carbamoyl]-4-phenyl-3-butenyl]-2'-isobutyl-2'-(methanesulphonyl)-4-methylvalerohydrazide in the form of a white solid.

MS: 538 (M+H)+.

EXAMPLE 46

(E)-2(R)-[1(S)-(Hydroxycarbamoyl)-4-phenyl-3-butenyl]-2'-isopropy-2'-(methanesulphonyl)-4-methylvalerohydrazide In an analogous manner to that described in Example 45, but using acetone in place of isobutyraldehyde in step (i), there was obtained (E)-2(R)-[1(S)-(hydroxycarbamoyl)-4-phenyl-3-butenyl]-2'-isobutyl-2'-(methanesulphonyl)-4-methylvalerohydrazide in the form of a white solid.

MS: 440 (M+H)+.

HPLC: Gradient elution using solvent A containing 5% solvent B increasing to 95% solvent B over 15 minutes; flow rate 1 ml/minute. Retention time: 11.16 minutes. Solvent A: H$_2$O/0.1% TFA; solvent B: CH$_3$CN/0.085% TFA. Column type: HYPERPEP 300A.

EXAMPLE 47

(E)-2(R)-[1(S)-(Hydroxycarbamoyl)-4-phenyl-3-butenyl]-2'-cyclopentyl-2'-(mothanesulphonyl)-4-methylvalerohydrazide In an analogous manner to that described in Example 45, but using cyclopentanone in place of isobutyraldehyde in step (i), there was obtained (E)-2(R)-[1(S)-

(hydroxycarbamoyl)-4-phenyl-3-butenyl]-2'-cyclopentyl-2'-(methanesulphonyl)-4-methylvalerohydrazide in the form of a white solid.

MS: 466 (M+H)$^+$.

HPLC: Accelerating gradient elution using solvent A containing 20% solvent B for 2 minutes then increasing to 80% solvent B over 18 minutes; flow rate 1 ml/minute. Retention time: 17.57 minutes. Solvent A: H$_2$O/0.1% TFA; solvent B: CH$_3$CN/0.085% TFA. Column type: HYPERPEP 300A.

EXAMPLE 48

(E)-2(R)-[1(Hydroxycarbamoyl)-4-phenyl-3-butenyl]-2'-(4-tetrahydropyranyl)-2'-(methanesulphonyl)-4-methylvalerohydrazide In an analogous manner to that described in Example 45, but using tetrahydro-4H-pyran-4-one in place of isobutyraldehyde in step (i), there was obtained (E)-2(R)-[1(S)-(hydroxycarbamoyl)-4-phenyl-3-butenyl]-2'-(methanesulphonyl)-4-methylvalerohydrazide in the form of a white solid.

MS: 482 (M+H)$^+$.

HPLC: Accelerating gradient elution using solvent A containing 20% solvent B for 2 minutes increasing to 80% solvent B over 18 minutes; flow rate 1 ml/minute. Retention time: 13.72 minutes. Solvent A H$_2$O/0.1% TFA; solvent B: CH$_3$CN/0.085% TFA. Column type: HYPERPEP 300A.

EXAMPLE 49

(E)-2(R)-[1S-(Hydroxycarbamoyl)-4-phenyl-3-butenyl]-2'-(4-tetrahydrothiopyranyl)-2'-(methanesulphonyl)-4-methylvalerohydrazide In an analogous manner to that described in Example 45, but using tetrahydrothiopyran-4-one in place of isobutyraldehyde in step (i), there was obtained (E)-2(R)-[1(S)-(hydroxycarbamoyl)-4-phenyl-3-butenyl]-2'-(4-tetrahydrothiopyranyl)-2'-(methanesulphonyl)-4-methylvalerohydrazide in the form of a white solid.

MS: 498 (M+H)$^+$.

HPLC: Accelerating gradient elution using solvent A containing 20% solvent B for 2 minutes increasing to 80% solvent B over 18 minutes; flow rate 1 ml/minute. Retention time: 17.35 minutes. Solvent A H$_2$O/0.1% TFA; solvent B: CH$_3$CN/0.085% TFA. Column type: HYPERPEP 300A.

EXAMPLE 50

(E)-2(R)-[1(S)-(Hydroxycarbamoyl)-4-phenyl-3-butenyl]-2'-(4-piperidinyl)-2'-(methanesulphonyl)-4-methylvalerohydrazide In an analogous manner to that described in Example 45, but using 1-tert-butoxycarbonyl-4-piperidone in place of isobutyraldehyde in step (i), there was obtained (E)-2(R)-[1(S)-(hydroxycarbamoyl)-4-phenyl-3-butenyl]-2'(4-piperidinyl)-2'-(methanesulphonyl)-4-methylvalerohydrazide in the form of a white solid.

MS: 481 (M+H)$^+$.

HPLC: Accelerating gradient elution using solvent A containing 20% solvent B for 2 minutes increasing to 80% solvent B over 18 minutes; flow rate 1 ml per minute. Retention time: 11.39 minutes. Solvent A: H$_2$O/0.1% TFA; solvent B: CH$_3$CN/0.085% TFA. Column type: HYPERPEP 300A.

EXAMPLE 51

(E)-2(R)-[1(S)-Hydroxycarbamoyl)-4-phenyl-3-butenyl]-2'-(isobutyl)-2'-(isopentanoyl)-4-methylvalerohydrazide In a analogous manner to that described in the first paragraph of Example 2, starting from 0.097 g of (E)-2(R)-[1(S)-[(tetrahydro-2(RS)-pyranyloxy)carbanoyl]-4-phenyl-3-butenyl]-2'-(isobutyl)-2'-(isopentanoyl)-4-methylvalerohydrazide there was obtained 0.047 g of (E)-2(R)-[1(S)-(hydroxycarbamoyl)-4-phenyl-3-butenyl]-2'-(isobutyl)-2'-(isopentanoyl)-4-methylvalerohydrazide in the form of a white solid.

MS: 460 (M+H)$^+$, 482 (M+Na)$^+$.

HPLC: Gradient elution using solvent A containing 5% solvent B increasing to 95% solvent B over 15 minutes; flow rate 1 ml/minute. Retention time: 12.79 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-(isobutyl)-2'-(isopentanoyl)-4-methylvalerohydrazide used as the starting material was prepared as follows:

(i) A solution of 0.25 g of (E)-2(R)-[1(S)-(tert-butoxycarbonyl)-4-phenyl-3-butenyl]-2'-isobutyl-4-methylvalerohydrazide 0.061 ml of pyridine and a crystal of 4-dimethylaminopyridine in 6 ml dichlomethane was cooled to 0° C. under a nitrogen atmosphere. 0.091 ml of isopentanoyl chloride was added and the reaction mixture was warmed to room temperature. After stirring for 2 hours at room temperature the reaction mixture was diluted with dichloromethane and washed with 2M aqueous hydrochloric acid and then with brine. The dichloromethane phase was dried over anhydrous magnesium sulphate and the solvent was evaporated. The residue was then dissolved in 10 ml of a 20% solution of trifluoroacetic acid in dichloromethane and stirred at room temperature for 2 hours. The solvents were evaporated and the residue was purified by flash column chromatography on silica gel using 1% methanol in dichloromethane for the elution. There was obtained 0.16 g of (E)-2(R)-[1(S)-(carboxy)-4-phenyl-3-butenyl]-2'-(isobutyl)-2'-(isopentanoyl)-4-methylvalerohydrazide in the form of a white foam.

MS: 445 (M+H)$^+$.

(ii) In an analogous manner to that described in Example 2, part (v), starting from 0.16 g of (E)-2(R)-[1(S)-(carboxy)-4-phenyl-3-butenyl]-2'-(isobutyl)-2'-(isopentanoyl)-4-methylvalerohydrazide there was obtained 0.097 g of (E)-2(R)-[1(S)-[(tetrahydro-2(RS)-pyranyloxy)carbamoyl]-4-phenyl-3-butenyl]-2'-(isobutyl)-2'-(isopentanoyl)-4-methylvalerohydrazide in the form of a white solid.

MS: 544 (M+H)$^+$.

EXAMPLE 52

(E)-2(R)-[1(S)-(Hydroxycarbamoyl)-4-phenyl-3-butenyl]-2'-(isobutyl)-2'-(cyclohexanecarbonyl)-4-methylvalerohydrazide In an analogous manner to that described in Example 51, but using cyclohexanecarbonyl chloride in place of isopentanoyl chloride in step (i), there was obtained (E)-2(R)-[1(S)-(hydroxycarbamoyl)-4-phenyl-3-butenyl]-2'-(isobutyl)-2'-(cyclohexanecarbonyl)-4-methylvalerohydrazide in the form of a white solid.

MS: 486 (M+H)$^+$.

HPLC: Accelerating gradient elution using solvent A containing 35% solvent B for 5 minutes increasing to 70% solvent B over 15 minutes; flow rate 1 ml/minute. Retention time: 15.44 minutes. Solvent A: H$_2$O/0.1% TFA; solvent B: CH$_3$CN/0.085% TFA. Column type: HYPERPEP 300A.

EXAMPLE 53

(E)-2(R)-[1(S)-(Hydroxycarbamoyl)-4-phenyl-3-butenyl]-4-methyl-N-(2,6-dioxopiperidino)valeramide In an analogous manner to that described in the first paragraph of Example 45, starting from 0.095 g of (E)-2

(R)-[1(S)-[(tetrahydro-2(RS)-pyranyloxy)carbamoyl]-4-phenyl-3-butenyl]-4-methyl-N-(2,6-dioxopiperidino) valeramide there was obtained 0.027 g of (E)-2(R)-[1(S)-(hydroxycarbamoyl)-4-phenyl-3-butenyl]-4-methyl-N-(2,6-dioxopiperidino)valeramide in the form of a white solid. MS: 416 (M+H)$^+$.

HPLC: Accelerating gradient elution using solvent A containing 20% solvent B for 5 minutes increasing to 70% solvent B over 15 minutes; flow rate 1 ml/minute. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy)carbamoyl]-4-phenyl-3-butenyl]-4-methyl-N-(2,6-dioxopiperidino)valeramide used as the starting material was prepared as follows:

(i) A solution of 1.0 g of (E)-2(R)-[1(S)-(tert-butoxycarbonyl)-4-phenyl-3-butenyl]-4-methylvalerohydrazide, 0.35 g of glutaric anhydride and 0.85 ml of triethylamine in 30 ml of dry toluene was heated at reflux under a nitrogen atmosphere for 7 hours. The mixture was cooled to room temperature and washed with 2M aqueous hydrochloric acid, 5% aqueous sodium hydrogen carbonate and brine. The organic phase was dried over anhydrous magnesium sulphate and the solvent was then evaporated. The residue was triturated with diethyl ether to give 0.623 g of (E)-2(R)-[1(S)-(tert-butoxycarbonyl)-4-phenyl-3-butenyl]-4-methyl-N-(2,6-dioxopiperidino)valeramide in the form of a white solid.
MS: 457 (M+H)$^+$.

(ii) In an analogous manner to that described in Example 2, parts (iv) and (v), starting from 0.62 g of (E)-2(R)-[1(S)-(tert-butoxycarbonyl)-4-phenyl-3-butenyl]-4-methyl-N-(2,6-dioxopiperidino)valeramide there was obtained 0.095 g of (E)-2(R)-[1(S)-tetrahydro-2(RS)-pyranyloxy)carbamoyl]-4-phenyl-3-butenyl]-4-methyl-N-(2,6-dioxopiperidino)valeramide in the form of a white solid.
MS: 500 (M+H)$^+$.

EXAMPLE 54

(E)-N-(Tetrahydro-1,2-thiazin-2-yl)-2(R)-[1(S)-(hydroxycarbamoyl)-4-phenyl-3-butenyl]-4-methylvaleramide In an analogous manner to that described in the first paragraph of Example 45, from 0.048 g of (E)-N-(tetrahydro-1,2-thiazin-2-yl)-2(R)-[1(S)-[(tetrahydro-2(RS)-pyranyloxy)carbamoyl]-4-phenyl-3-butenyl]-4-methylvaleramide there was obtained 0.01 g of (E)-N-(tetrahydro-1,2-thiazin-2-yl)-2(R)-[1(S)-(hydroxycarbamoyl)-4-phenyl-3-butenyl]-4-methylvaleramide in the form of a white solid.
MS: 438 (M+H)$^+$.

The (E)-N-(tetrahydro-1,2-thiazin-2-yl)-2(R)-[1(S)-[(tetrahydro-2(RS)-pyranyloxy)carbamoyl]-4-phenyl-3-butenyl]-4-methylvaleramide used as the starting material was prepared as follows:

(i) A solution of 5.64 g of the tert-butyl ester of leucic acid and 3.6 ml of pyridine in 40 ml of dichloromethane was added dropwise to a solution of 6.0 ml of trifluoromethanesulphonic anhydride in 60 ml of dichloromethane under a nitrogen atmosphere at 0° C. After 10 minutes the mixture was washed twice with water and then dried over anhydrous magnesium sulphate. The mixture was concentrated to approximately one third of the original volume and then added dropwise to a cooled (0° C.) solution of the anion prepared by treating 5.22 g of tert-butylmethyl malonate in 50 ml of dimethylformamide with 1.32 g of a 60% suspension of sodium hydride in mineral oil under a nitrogen atmosphere for 2 hours. The mixture was left to warm to room temperature overnight and then the solvent was evaporated. The residue was dissolved in ethyl acetate and the solution was washed with water. The organic phase was dried over anhydrous magnesium sulphate and evaporated to give 10.0 g of 1,2-tert-butyl-1,4-dimethyl-1,1,2(R)-pentane-tricarboxylate in the form of a red oil.

(ii) 1.53 g of a 60% suspension of sodium hydride in mineral oil were added to a stirred solution of 12.55 g of 1,2-tert-butyl-1,4-dimethyl-1,1,2(R)-pentanetricarboxylate in 120 ml of dimethylformamide under a nitrogen atmosphere. The mixture was stirred until gas evolution had stopped (approximately 1 hour), a solution of 7.54 g of cinnamyl bromide in 70 ml of dimethylformamide was added dropwise and the mixture was stirred overnight at room temperature. The solvent was evaporated and the residue was dissolved in ethyl acetate and washed twice with water. The organic phase was dried over anhydrous magnesium sulphate and the solvent was evaporated. The residue was purified by flash column chromatography on silica gel using hexane/ethyl acetate (9.1) for the elution. There were obtained 15.06 g of (E)-1,2-tertbutyl-1,4-dimethyl-1-(3-phenyl-prop-2-en-1-yl)-1,1,2(R)-pentanetricarboxylate in the form of a yellow oil.

(iii) A solution of 2.7 g of (E)-1,2-tertbutyl-1,4-dimethyl-1-(3-phenyl-prop-2-en-1-yl)-1,1,2(R)-pentanetricarboxylate in 30 ml of a 20% solution of trifluoroacetic acid in dichloromethane was stirred at room temperature for 1 hour. The solvents were evaporated and the residue was dissolved in 20 ml of toluene. 1.6 ml of triethylamine were added and the mixture was then stirred at reflux temperature for 2 hours. After cooling the mixture was washed with 2M aqueous hydrochloric acid and water. The organic phase was dried over anhydrous magnesium sulphate and evaporated to give a pale yellow oil. The oil was dissolved in 10 ml of hexane and 0.6 g of cyclohexylamine was added. The resulting salt was collected by filtration and then suspended in 20 ml of ether and washed with 1M sulphuric acid. The ether phase was dried over anhydrous magnesium sulphate and evaporated to give 1.5 g of (E)-2(R)-isobutyl-4-methyl-3-[(RS)-3-phenylprop-2-en-1yl)]-succinate in the form of a white solid.

(iv) A solution of 40 g of 4-chloro-1-butanesulphonyl chloride in 400 ml of diethyl ether was added dropwise to a solution of 30.4 g of tert-butyl carbazate and 17 ml of pyridine in 400 ml of diethyl ether at room temperature. The mixture was stirred at room temperature for 72 hours and then washed with water. The separated organic phase was dried over anhydrous magnesium sulphate. The oily residue obtained after evaporation of the solvent was purified by flash column chromatography on silica gel using hexane/ethyl acetate (8:2, increasing to 6:4) for the elution. 10.25 g of tert-butyl 2-[(4-chlorobutyl)sulphonyl]carbazate were obtained in the form of a white solid.

(v) 1.7 g of a 60% suspension of sodium hydride in mineral oil were added to a solution of 10.25 g of tert-butyl 2-[(4-chlorobutyl)sulphonyl]carbazate in 300 ml of dry tetrahydrofuran at room temperature under a nitrogen atmosphere. After stirring at room temperature for 48 hours the solvent was evaporated and the residue was dissolved in ethyl acetate and washed with water. The organic phase was dried over anhydrous magnesium sulphate and evaporated. The residue was recrystallized from ethyl acetate/hexane to give 1.86 g of tert-butyl (tetrahydro-1,2-thiazin-2-yl)carbamate S,S-dioxide in the form of a pale yellow solid.

(vi) A solution of 1.86 g of tert-butyl (tetrahydro-1,2-thiazin-2-yl)carbamate S,S-dioxide in 20 ml of 4M hydrogen chloride in ethyl acetate was stirred at room temperature for 1 hour. The solvent was evaporated and the residue was stirred in ether for 5 minutes and then filtered to give 1.24 g of tetrahydro-1,2-thiazine-2-amine S,S-dioxide in the form of a white solid.

(vii) A solution of 1.39 g of (E)-2(R)-isobutyl-4-methyl-3[(RS)-3-phenyl-prop-2-en-1-yl)]-succinate in 15 ml of dichloromethane was cooled to −10° C. under a nitrogen atmosphere. 4 drops of dimethylformamide and 0.418 ml of oxalyl chloride were added and the mixture was left to warm to 0° C. over 1 hour. The solvent was evaporated and replaced by 2 ml of dichloromethane. The resulting solution was then added dropwise to a solution of 1.24 g of tetrahydro-1,2-thiazine-2-amine S,S-dioxide and 1.4 ml of triethylamine in 20 ml of dichloromethane under a nitrogen atmosphere at 0° C. The mixture was held at 0° C. overnight and was then washed with water. The organic phase was dried over anhydrous magnesium sulphate and evaporated. The residue was purified by flash column chromatography on silica gel using ethyl acetatelhexane (2:8, increasing to 10:0) for the elution. There was obtained 0.44 g of (E)-N-(tetrahydro-1,2-thiazin-2-yl)-2(R)-[1(S)-(methoxycarbonyl)-4-phenyl-3-butenyl]-4-methylvaleramide in the form of a white solid.

(viii) 0.573 ml of a 2M solution of trimethylaluminium in toluene was added to a solution of 0.134 g of O-(tetrahydro-2H-pyran-2(RS)-yl)hydroxylamine in 5 ml of dry toluene at 0° C. under a nitrogen atmosphere. The mixture was stirred at room temperature for 1 hour and then 0.10 g of (E)-N-tetrahydro-1,2-thiazin-2-yl)-2(R)-[1(S)-(methoxycarbonyl)-4-phenyl-3-butenyl]-4-methylvaleramide was added in one portion. The mixture was heated at 55° C. for 3 hours and then left to cool to room temperature overnight. The mixture was diluted with ethyl acetate and washed in succession with 2M aqueous hydrochloric acid and 5% aqueous sodium hydrogen carbonate solution and then dried over anhydrous magnesium sulphate. The solvent was evaporated and the residue was triturated with diethyl ether to give 0.048 g of (E)-N-(tetrahydro-1,2-thiazin-2-yl)-2(R)-[1(S)-[(tetrahydro-2(RS)-pyranyloxy)-carbamoyl]-4-phenyl-3-butenyl]-4-methylvaleramide in the form of a white solid.
MS: 522 (M+H)$^+$.

EXAMPLE 55

(E)-2(R)-[1(S)-(Hydroxycarbamoyl)-4-phenyl-3-butenyl]-2-(methane-sulphonil)-2-phenylhexanohydrazide.

In an analogous manner to that described in the first paragraph of Example 1, starting from 0.37 g of (E)-2(R)-[1(S)-(carboxy)-4-phenyl-3-butenyl]-2'-(methanesulphonyl)-2'-phenylhexanohydrazide there was obtained 0.10 g of (E)-2(R)-[1(S)-(hydroxycarbamoyl)-4-pheny-3-butenyl]-2-(methanesulphonyl)-2-phenylhexanohydrazide in the form of a white solid.
MS: 474 (M+H)$^+$.

HPLC: Gradient elution using solvent A containing 5% solvent B increasing to 95% solvent B over 15 minutes; flow rate 1 ml/minute. Retention time: 11.97 minutes. Solvent A: H$_2$O/0.1% TFA; solvent B: CH$_3$CN/0.085% TFA. Column type: HYPERSIL 300A.

The (E)-2(R)-[1(S)-(carboxy)-4-phenyl-3-butenyl]-2'-(methanesulphonyl)-2'-phenylhexanohydrazide used as the starting material was prepared as follows:

(i) In an analogous manner to that described in Example 54, parts (i) and (ii), but using benzyl 2-hydroxyhexanoate and benzyl tert-butylmalonate, there was obtained (E)-1,2-dibenzyl-1-tert-butyl-1-(3-phenylprop-2-en-1-(3-phenylprop-2-en-1-yl)-1,1,2(R)-hexanetricarboxylate in the form of a yellow oil.

(ii) A solution of 2.27 g of sodium hydroxide in 20 ml of water was added to a solution of 6.47 g of (E)-1,2-dibenzyl-1-tert-butyl-1-(3-phenylprop-2-en-1-yl)-1,1,2(R)-hexanetricarboxylate in 40 ml of ethanol. The mixture was heated at reflux overnight and then cooled and evaporated. The residue was diluted with water and acidified to pH 1 with concentrated hydrochloric acid. The aqueous phase was extracted twice with ethyl acetate and then the combined organic phases were washed with water and dried over anhydrous magnesium sulphate. The solvents were evaporated and the residue was dissolved in 50 ml of toluene. 1.53 ml of triethylamine were added to the mixture which was then heated at reflux for 3.5 hours and left to cool overnight. The mixture was washed with 2M aqueous hydrochloric acid and then dried over anhydrous magnesium sulphate. The solvent was evaporated and the yellow oil obtained was dissolved in hexane and treated with 1.09 g of cyclohexylamine to form a salt which was collected by filtration. The salt was then partitioned between ethyl acetate and 1N sulphuric acid and the organic phase was subsequently washed with water, dried over anhydrous magnesium sulphate and evaporated to give 1.3 g of (E)-2(R)-butyl-4-tert-butyl-3-[(RS)-(3-phenylprop-2-en-1-yl)]-succinate in the form of a pale yellow solid.

(iii) In an analogous manner to that described in Example 1, parts (i)–(iii), starting from (E)-2-(R)-butyl-4-tert-butyl-3-[(RS)-(3-phenylprop-2-en-1-yl)]-succinate there was obtained (E)-2(R)-[1(S)-(carboxy)-4-phenyl-3-butenyl]-2'-(methanesulphonyl)-2'-phenylhexanohydrazide in the form of a white solid.
MS: 459 (M+H)$^+$.

EXAMPLE 56

(E)-2-(R)-[1(S)-(Hydroxycarbamoyl)-4-phenyl-3-butenyl]-2'-(methanesulphonyl)-2',3-diphenylpropionohydrazide In an analogous manner to that described in the first paragraph of Example 44, starting from 0.162 g of (E)-2(R)-[1(S)-({O-4-methoxybenzyl}hydroxycarbamoyl)-4-phenyl-3-butenyl]-2'-(methanesulphonyl)-2',3-diphenylpropionohydrazide there was obtained 0.040 g of (E)-2(R)-[1(S)-(hydroxycarbamoyl)-4-phenyl-3-butenyl]-2'-(methanesulphonyl)-2',3-diphenylpropionohydrazide in the form of a white solid.
MS: 508 (M+H)$^+$.

HPLC: Gradient elution using solvent A containing 5% solvent B increasing to 95% solvent B over 15 minutes; flow rate 1 ml/minute. Retention time: 12.25 minutes. Solvent A: H₂O/0.1% TFA; solvent B: CH₃CN/0.085% TFA. Column type: HYPERPEP 300A.

The (E)-2(R)-[1(S)-({O-4-methoxybenzyl}hydroxycarbamoyl)-4-phenyl-3-butenyl]-2'-(methanesulphonyl)-2',3-diphenylpropionohydrazide used as the starting material was prepared as follows:

(i) In an analogous manner to that described in Example 55, parts (i)–(iii), but starting from benzyl a-hydroxybenzenepropanoate, there was obtained (E)-2(R)-[1(S)-(carboxy)-4-phenyl-3-butenyl]-2'-(methanesulphonyl)-2',3-diphenylpropionohydrazide in the form of a white solid.

(ii) A solution of 0.29 g of (E)-2(R)-[1(S)-(carboxy)-4-phenyl-3-butenyl]-2'-(methanesulphonyl)-2',3-diphenylpropionohydrazide in 5 ml DMF was cooled to 0° C. under a nitrogen atmosphere and 0.18 g of (O-4-methoxybenzyl)hydroxylamine and 0.124 g of 1-ethyl-3-(3-dimethylaminopropyl)carbodiimide hydrochloride were added. The mixture was left to warm to room temperature and was stirred overnight. The solvent was evaporated and the residue was dissolved in dichloromethane and washed with water. The organic phase was dried over anhydrous magnesium sulphate and evaporated. The residue was triturated with diethyl ether to give 0.17 g of (E)-2(R)-[1(S)-({O-4-(methoxybenzyl}hydroxycarbamoyl)-4-phenyl-3-butenyl]-2'-(methanesulphonyl)-2',3-diphenylpropionohydrazide in the form of a white solid.

EXAMPLE 57

(E)-2(RS)-[1(RS)-(Hydroxycarbamoyl)-4-phenyl-3-butenyl]-2'-(methane-sulphonyl)-2,2'-diphenylacetohydrazide In an analogous manner to that described in the first paragraph of Example 45, starting from 1.05 g of (E)-2(RS)-[1(RS)-(tetrahydro-2(RS)-pyranyl-oxy)carbamoyl]-4-phenyl-3-butenyl]-2'-(methanesulphonyl)-2,2'-diphenylacetohydrazide there was obtained 0.598 g of (E)-2(RS)-[1(RS)-(hydroxycarbamoyl)-4-phenyl-3-butenyl]-2'-(methanesulphonyl)-2,2'-diphenylacetohydrazide in the form of a white solid.
MS: 494 (M+H)⁺.
HPLC: Accelerating gradient elution using solvent A containing 35% solvent B for 5 minutes increasing to 80% over 15 minutes; flow rate 1 ml/minute. Retention time: 8.54 minutes. Solvent A: H₂O/0.1% TFA; solvent B: CH₃CN/0.085% TFA. Column type: HYPERPEP 300A.

The (E)-2(RS)-[1(RS)-(tetrahydro-2(RS)-pyranyloxy) carbamoyl]-4-phenyl-3-butenyl]-2'-(methanesulphonyl)-2,2'-diphenylacetohydrazide used as the starting material was prepared as follows:

(i) In an analogous manner to that described in Example 55, parts (i)–(iii), but starting from benzyl mandelate, there was obtained (E)-2(RS)-[1(RS)-(carboxy)-4-phenyl-3-butenyl]-2'-(methanesulphonyl)-2,2'-diphenylacetohydrazide in the form of a white solid.
MS: 479 (M+H)⁺.

(ii) In an analogous manner to that described in Example 2, part (v), from 1.1 g of (E)-2(RS)-[1(RS)-(carboxy)-4-phenyl-3-butenyl]-2'-(methanesulphonyl)-2,2'-diphenylacetohydrazide there was obtained 1.1 g of (E)-2(RS)-[1(RS)-[(tetrahydro-2(RS)-pyranyloxy) carbamoyl]-4-phenyl-3-butenyl]-2'-(methanesulphonyl)-2,2'-diphenylacetohydrazide in the form of a white solid.
MS: 578 (M+H)⁺.

EXAMPLE 58

(E)-2(R)-[1(S)-(Hydroxycarbamoyl)-4-(2-thiazolyl)-3-butenyl]-2'-(methanesulphonyl)-4-methyl-2'-phenylvalerohydrazide In an analogous manner to that described in the first paragraph of Example 45, from 0.29 g of (E)-2(R)-[1(S)-[(tetrahydro-2(RS)-pyranyloxy)carbamoyl]-4-(2-thiazolyl)-3-butenyl]-2-(methanesulphonyl)-4-methyl-2'-phenylvalerohydrazide there was obtained 0.17 g of (E)-2(R)-[1 (S)-(hydroxycarbamoyl)-4-(2-thiazolyl)-3-butenyl]-2'-(methanesulphonyl)-4-methyl-2'-phenylvalerohydrazide in the form of a white solid.
MS: 481 (M+H)⁺.
HPLC: Gradient elution using solvent A containing 5% solvent B increasing to 95% solvent B over 15 minutes; flow rate 1 ml/minute. Retention time: 9.97 minutes. Solvent A: H₂O/0.1% TFA; solvent B: CH₃CN/0.085% TFA. Column type: HYPERPEP 300A.

The (E)-2(R)-[1(S)-[(tetrahydro-2(RS)-pyranyloxy) carbamoyl]-4-(2-thiazolyl)-3-butenyl]-2'-(methanesulphonyl)-4-methyl-2'-phenylvalerohydrazide used as the starting material was prepared as follows:

(i) A solution of 4.0 g of (E)-2(R)-[1(S)-(tert-butoxycarbonyl)-4-phenyl-3-butenyl]-4-methylvaleric acid in 200 ml of dichloromethane was cooled to –78° C. and ozone was bubbled through the solution until it turned blue. The mixture was left to warm to room temperature and 20 ml of dimethyl sulphide were added. The mixture was stirred at room temperature for 3 hours and then the solvent was evaporated. The residue was purified by flash column chromatography on silica gel using hexane/ethyl acetate (1:1) for the elution. There were obtained 1.8 g of 2(R)-[1(S)-(tert-butoxycarbonyl)-propan-3-al]-4-methylvaleric acid in the form of a pale yellow solid.

(ii) 0.25 g of potassium tert-butoxide were added to a solution of 0.79 g of triphenyl-(2-thiazolylmethyl) phosphonium chloride in 10 ml of dry toluene. After stirring at room temperature for 3 hours a solution of 0.83 g of 2(R)-[1(S)-(tert-butoxycarbonyl)-propan-3-al]-4-methylvaleric in 5 ml of toluene was added and the mixture was stirred for a further 48 hours at room temperature. The solvent was evaporated and the residue was purified by flash column chromatography on silica gel using dichloromethane/methanol (95:5) for the elution. There was obtained 0.43 g of (E)-2(R)-[1 (S)-(tert-butoxycarbonyl)-4-(2-thiazolyl)-3-butenyl]-methylvaleric acid as a pale yellow oil.
MS: 354 (M+H)⁺.

(iii) In an analogous manner to that described in Example 1, parts (i)–(iii), and in Example 2, part (v), starting from (E)-2(R)-[1(S)-(tert-butoxycarbonyl)-4-(2-thiazolyl)-3-butenyl]-methylvaleric acid there was obtained (E)-2(R)-[1(S)-[(tetrahydro-2(RS)-pyranyloxy)carbamoyl]-4-(2-thiazolyl)-3-butenyl]-2'-(methanesulphonyl)-4-methyl-2'-phenylvalerohydrazide in the form of a white solid.
MS: 565 (M+H)⁺.

The following Examples illustrate typical pharmaceutical compositions containing the hydrazine derivatives provided by the present invention:

EXAMPLE 59

(E)-2(R)-[1(S)-(Hydroxycarbamoyl)-4-phenyl-3-butenyl]-2'-isobutyryl-2'-isobutyl-4-methylvalerohydrazide A solution of 0.32 g of (E)-2(R)-[1(S)-[(tetrahydro-2(RS)-pyranyloxy)carbamoyl]-4-phenyl-3-butenyl]-2'-isobutyryl-2'-isobutyl-4-methylvalerohydrazide in 10 ml of methanol was treated with 0.03 g of 4-toluenesulphonic acid. The mixture was stirred for 2 hours at room temperature and then the solvent was evaporated to leave a glass. This residue was triturated with diethyl ether to give 0.15 g of (E)-2(R)-[1(S)-(hydroxycarbamoyl)-4-phenyl-3-butenyl]-2'-isobutyryl-2'-isobutyl-4-methylvalerohydrazide in the form of a white solid.

MS: 446 (M+H)$^+$.

HPLC: Gradient elution using solvent A containing 20% solvent B for 5 minutes increasing to 65% solvent B from 5 minutes to 20 minutes; flow rate 1 ml/minute. Retention time: 17.48 minutes. Solvent A: $H_2O$/0.1% TFA; solvent B: $CH_3CN$/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-isobutyryl-2'-isobutyl-4-methylvalerohydrazide used as the starting material was prepared as follows:

(i) A solution of 0.70 g of (E)-2(R)-[1(S)-(tert-butoxycarbonyl)-4-phenyl-3-butenyl]-2'-isobutyl-4-methylvalerohydrazide, 0.38 ml of pyridine and a crystal of 4-dimethylaminopyridine in 8 ml of dichlomethane was cooled to 0° C. under a nitrogen atmosphere. 0.67 ml of isobutyric anhydride was added and the reaction mixture was warmed to room temperature. After stirring for 16 hours at room temperature the reaction mixture was diluted with dichloromethane and washed with 2M aqueous hydrochloric acid and then with brine. The dichloromethane phase was dried over anhydrous magnesium sulphate and the solvent was evaporated.

Chromatography on silica gel using ethyl acetate/hexane (1:5) for the elution followed by evaporation yielded 0.56 g of (E)-2(R)-[1(S)-(tert-butoxycarbonyl)-4-phenyl-3-butenyl]-2'-isobutyryl-2'-isobutyl-4-methylvalerohydrazide as a white foam.

MS: 487(M+H)$^+$.

(ii) 0.56 g of the tert.butyl ester was dissolved in 20 ml of a 50% solution of trifluoroacetic acid in dichloromethane and stirred at room temperature for 1.5 hours. The solvents were evaporated and traces of trifluoroacetic acid were removed by the addition and evaporation of toluene (2×10 ml). The residue was triturated with diethyl ether/hexane (1:1) to give 0.39 g of (E)-2(R)-[1(S)-(carboxy)-4-phenyl-3-butenyl]-2'-methylvalerohydrazide in the form of a white solid.

MS: 431 (M+H)$^+$.

(iii) In an analogous manner to that described in Example 2, part (v), starting from 0.39 g of (E)-2(R)-[1(S)-(carboxy)-4-phenyl-3-butenyl]-2'-methylvalerohydrazide there was obtained 0.32 g of (E)-2(R)-[1(S)-[(tetrahydro-2(RS)-pyranyloxy)carbamoyl]-4-phenyl-3-butenyl]-2'-isobutyryl-2'-isobutyl-4-methylvalerohydrazide in the form of a white solid.

MS: 530 (M+H)$^+$.

EXAMPLE 60

(E)-2'-Acetyl-2(R)-[1(S)-(hydroxycarbamoyl)-4-phenyl-3-butenyl]-2'-isobutyl-4-methylvalerohydrazide In an analogous manner to that described in Example 59, but using acetic anhydride in place of isobutyric anhydride in step (i), there was obtained (E)-2'-acetyl-2(R)-[1(S)-(hydroxycarbamoyl)-4-phenyl-3-butenyl]-2'-isobutyl-4-methylvalerohydrazide in the form of a white solid.

MS: 418 (M+H)$^+$.

HPLC: Elution using solvent A; flow rate 1 ml/minute. Retention time: 4.86 minutes. Solvent A: $H_2O$/0.1% TFA; Column type: HYPERPEP 300A.

EXAMPLE 61

(E)-2'-Benzoyl-2'-isobutyl-2(R)-[1(S)-(hydroxycarbamoyl)-4-phenyl-3-butenyl]-4-methylvalerohydrazide In an analogous manner to that described in Example 59, but using benzoyl chloride in place of isobutyric anhydride in step (i), there was obtained (E)-2'-benzoyl-2'-isobutyl-2(R)-[1(S)-(hydroxycarbamoyl)-4-phenyl-3-butenyl]-2'-isobutyl-4-methylvalerohydrazide in the form of a white solid.

MS: 480 (M+H)$^+$.

HPLC: Gradient elution using solvent A containing 5% solvent B increasing to 95% solvent B over 15 minutes; flow rate 1 ml/minute. Retention time: 12.37 minutes. Solvent A: $H_2O$/0.1% TFA; solvent B: $CH_3CN$/0.085% TFA. Column type: HYPERPEP 300A.

EXAMPLE 62

Methyl (E)-[2(R)-[1(S)-(hydroxycarbamoyl)-4-phenyl-3-butenyl]-4-methylvaleryl]-1-isobutylhydrazino]glyoxylate A solution of 0.34 g of methyl (E)-[2(R)-[1(S)-[(tetrahydro-2(RS)-pyranyloxy)carbamoyl]-4-phenyl-3-butenyl]-4-methylvaleryl]-1-isobutylhydrazino]glyoxylate in 5 ml of methanol was treated with 0.04 g of 4-toluenesulphonic acid. The mixture was stirred for 2.5 hours at room temperature and then the solvent was evaporated to give a white semi-solid mass. This residue in ethyl acetate was washed with 5% sodium hydrogen carbonate solution, dried over magnesium sulphate and evaporated to give a solid. This was triturated with diethyl ether to give 0.19 g of methyl (E)-[2(R)-[1(S)-(hydroxycarbamoyl)-4-phenyl-3-butenyl]-4-methylvaleryl]-1-isobutylhydrazino]glyoxylate in the form of a white solid.

MS: 462 (M+H)$^+$.

HPLC: Gradient elution using solvent A containing 5% solvent B increasing to 95% solvent B over 15 minutes; flow rate 1 ml/minute. Retention time: 12.26 minutes. Solvent A: $H_2O$/0.1% TFA; solvent B: $CH_3CN$/0.085% TFA. Column type: HYPERPEP 300A.

The methyl (E)-[2(R)-[1(S)-[(tetrahydro-2(RS)-pyranyloxy)carbamoyl-4-phenyl-3-butenyl]-4-methylvaleryl]-1-isobutylhydrazino]glyoxylate used as the starting material was prepared as follows:

(i) A solution of 1.0 g of (E)-2(R)-[1(S)-(tert-butoxycarbonyl)-4-phenyl-3-butenyl]-2'-isobutyl-4-methylvalerohydrazide, 0.40 ml of pyridine and a crystal of 4-dimethylaminopyridine in 10 ml dichlomethane was cooled to 0° C. under a nitrogen atmosphere. 0.27 ml of methyl oxalyl chloride was added and the reaction mixture was warmed to room temperature. After stirring for 16 hours at room temperature the reaction mixture was evaporated to dryness. The residue in ethyl acatate was washed with 2M aqueous hydrochloric acid, 5% sodium hydrogen carbonate solution and water. The organic phase was dried over anhydrous magnesium sulphate and the solvent was evaporated. Trituration of the residue with hexane yielded 0.91 g of methyl (E)-[2(R)-[1(S)-(tert-butoxycarbonyl)-4-phenyl-3-butenyl]-4-methylvaleryl]-1-isobutylhydrazino]glyoxylate as a white solid.

MS: 503(M+H)$^+$.

(ii) 0.90 g of the tert.butyl ester prepared in paragraph (i) was dissolved in 20 ml of a 50% solution of trifluoroacetic acid in dichloromethane and stirred at room temperature for 3 hours. The solvents were evaporated and traces of trifluoroacetic acid were removed by the addition and evaporation of toluene (2×20 ml). The residue was dried in a vacuum to give 0.95 g of methyl (E)-[2(R)-[1(S)-(carboxy)-4-phenyl-3-butenyl]-4-methylvaleryl]-1-isobutylhydrazino]glyoxylate in the form of a gum.

MS: 446 (M+H)$^+$.

(iii) The carboxylic acid prepared in paragraph (ii) was dissolved in 5 ml of dimethylformamide, cooled to 0° C. and treated in succession with 0.75 g of O-(tetrahydro-2H-pyran-2(RS)-yl)hydroxylamine and 0.48 g of 1-ethyl-3-(3-dimethylaminopropyl) carbodiimide hydrochloride. The mixture was left to come to room temperature and was stirred overnight. The solvent was evaporated and the residue was dissolved in ethyl acetate. The ethyl acetate layer was washed with water, 2M hydrochloric acid, 5% sodium hydrogen carbonate solution and saturated sodium chloride solution, dried over anhydrous magnesium sulphate and evaporated to give a foam. Chromatography on silica gel using ethyl acatate/hexane (2:3) for the elution followed by evaporation gave 0.350 g of methyl (E)-[2(R)[1-(S)-[(tetrahydro-2(RS)-pyranyloxy)carbamoyl-4-phenyl-3-butenyl]-4-methylvaleryl]-1-isobutylhydrazino]glyoxylate in the form of a white solid.

MS: 546 (M+H)$^+$.

EXAMPLE 63

(E)-2(R)-[1(S)-(Hydrocarbamoyl)-4-phenyl-3-butenyl]-2'-isobutyl-4-methyl-2'-(methylglyoxyloyl)-valerohydrazide In an analogous manner to that described in Example 62, starting from (E)-2(R)-[1(S)-[(tetrahydro-2(RS)-pyranyloxy)carbamoyl]-4-phenyl-3-butenyl]-2'-isobutyl-4-methyl-2'-glyoxyloyl)-valerohydrazide there was obtained (E)-2(R)-[1(S)-(hydroxycarbamoyl)-4-phenyl-3-butenyl]-2'-isobutyl-4-methyl-2'-(methylglyoxyloyl)-valerohydrazide in the form of a white solid.

MS: 462 (M+H)$^+$.

HPLC: Gradient elution using solvent A containing 5% solvent B increasing to 95% solvent B over 15 minutes; flow rate 1 ml/minute. Retention time: 12.19 minutes. Solvent A: H$_2$O/0.01% TFA: solvent B: CH$_3$CN/0.085% TFA. Column type: HYPERPEP 300A.

The (E)-2(R)-[1(S)-[(tetrahydro-2(RS)-pyranyloxy) carbamoyl]4-phenyl-3-butenyl]-2'-isobutyl-4-methyl-2'-(methylglyoxyloyl)-valerohydrazide used as the starting material was prepared in a manner analogous to that described in Example 62 (i)–(iii) using pyruvoyl chloride in place of methyl oxalyl chloride.

MS: 530 (M+H)$^+$.

EXAMPLE 64

(E)-2(R)-[1(RS)-(Hydroxcarbamoyl)-4-(3-pyridyl)-3-butenyl]-2'-(methanesulphonyl)-4-methyl-2'-phenylvalerohydrazide A solution of 0.21 g of (E)-2(R)-[1(RS)-[(tetrahydro-2 (RS)-pyranyloxy)carbamoyl]-4-(3-pyridyl)-3-butenyl]-2'-(methanesulphonyl)-4-methyl-2'-phenylvalerohydrazide in 5 ml of methanol was treated with 0.097 g of 4-toluenesulphonic acid. The mixture was stirred for 2.5 hours at room temperature and then diluted with water. The solid was filtered off, washed with water and diethyl ether and dried in vacuum to yield 0.138 g of (E)-2(R)-[1(RS)-(hydroxycarbamoyl)-4-(3-pyridyl)-3-butenyl]-2'-(methanesulphonyl)-4-methyl-2'-phenylvalerohydrazide in the form of a white solid.

MS: 475 (M+H)$^+$.

HPLC: Gradient elution using solvent A containing 5% solvent B increasing to 95% solvent B over 15 minutes; flow rate 1 ml/minute. Retention times: 9.53 and 9.92 minutes (ratio of diastereoisomers (3:1). Solvent A: H$_2$O/0.1% TFA; solvent B: CH$_3$CN/0.085% TFA. Column type: HYPERPEP 300A.

The (E)-2(R)-[1(RS)-[(tetrahydro-2(RS)-pyranyloxy) carbamoyl]-4-(3-pyridyl)-3-butenyl]-2'-(methanesulphonyl)-4-methyl-2'-phenylvalero-hydrazide used as the starting material was prepared as follows:

(i) A solution of 6.81 g of 1,2-dibenzyl 1-tert-butyl-4-methyl-1(RS), 1,2(R)-pentanetricarboxylate in 50 ml of dry tetrahydrofuran was stirred under nitrogen at room temperature. 0.66 g of 60% sodium hydride was added and the mixture was stirred for 10 minutes. A solution of 2.66 g of 4-(3-pyridyl)allyl acetate and 0.87 g of tetrakis(triphenylphosphine)-palladium(0) in 40 ml of dry tetrahydrofuran was added and the mixture was stirred at room temperature for 4 hours. The tetrahydrofuran was evaporated and the residue was partitioned between dichloromethane and saturated sodium chloride solution. The organic solution was dried over anhydrous magnesium sulphate and evaporated to give an light-brown oil. Chromatography on silica gel, using ethyl acatate/hexane (2:3) for the elution and evaporation of the solvent gave 7.50 g of (E)-1,2-dibenzyl 1-tert-butyl-4-methyl-1-[3-(3-pyridyl)-prop-2-en-1-yl]-1(RS), 1,2(R)-pentanetricarboxylate.

MS: 572 (M+H)$^+$.

(ii) A solution of 2.80 g of sodium hydroxide in 40 ml of water was added to a solution of 4.00 g of (E)-1,2-dibenzyl 1-tert-butyl-4-methyl-1-[3-(3-pyridyl)-prop-2-en-1-yl]-1(RS),1,2(R)-pentanetricarboxylate in 40 ml of ethanol. The mixture was heated at reflux for 20 hours, cooled and evaporated. The residue was diluted with water and acidified to pH 6.5 with concentrated hydrochloric acid. The aqueous phase was extracted twice with diethyl ether and the combined organic phases were extracted with 50 ml of 0.25M sodium hydroxide solution. The solution was acidified to pH 6.5 with concentrated hydrochloric acid and reextracted with diethyl ether (2×50 ml). The combined organic phases were washed with brine, dried over magnesium sulphate and evaporated to 1.73 g of (E)-2(R)-butyl-4-tert-butyl-3-[(RS)-(3-(3-pyridyl)-prop-2-en-1-yl]-succinate in the form of a red gum.

MS: 348 (M+H)$^+$.

(iii) In an analogous manner to that described in Example 1, part (i), starting from 0.52 g of the carboxylic acid prepared in part (ii) of this Example there was obtained 0.447 g of (E)-2(R)-[1(RS)-(tert-butoxycarbonyl)-4-(3-pyridyl)-3-butenyl]-4-methyl-2'-phenylvalerohydrazide in the form of a white solid.

MS: 438 (M+H)$^+$.

(iv) In an analogous manner to that described in Example 1, part (ii), starting from 0.44 g of (E)-2(R)-[1(RS)-(tert-butoxycarbonyl)-4-(3-pyridyl)-3-butenyl]-4- methyl-2'-phenylvalerohydrazide was obtained 0.51 g of (E)-2(R)-[1(RS)-(tert-butoxycarbonyl)-4-(3-pyridyl)-3-butenyl]-4-methyl-2'-(methanesulphonyl)-2'-phenylvalerohydrazide in the form of a white solid.

MS: 516 (M+H)+.

(v) In an analogous manner to that described in Example 1, part (iii), starting from 0.50 g of (E)-2(R)-[1(RS)-(tert-butoxycarbonyl)-4-(3-pyridyl)-3-butenyl]-4-methyl-2'-(methanesulphonyl)-2'-phenylvalerohydrazide there was obtained 0.36 g of (E)-2(R)-[1(RS)-(carboxy)-4-(3-pyridyl)-3-butenyl]-4-methyl-2'-(methanesulphonyl)-2'-phenylvalerohydrazide

MS: 460 (M+H)+.

(vi) The carboxylic acid prepared in paragraph (v) was dissolved in 2 ml of dimethylformamide, cooled to 0° C. and treated in succession with 0.27 g of O-(tetrahydro-2H-pyran-2(RS)-yl)hydroxylamine and 0.16 g of 1-ethyl-3-(3-dimethylaminopropyl) carbodiimide hydrochloride. The mixture was left to come to room temperature and was stirred overnight. The solvent was evaporated and the residue was partitioned between water and ethyl acetate. The ethyl acetate layer was washed with water and with 5% sodium hydrogen carbonate solution, dried over anhydrous magnesium sulphate and evaporated. The resulting pale yellow gum was triturated with diethyl ether to give 0.22 g of (E)-2(R)-[1(RS)-[(tetrahydro-2(RS)-pyranyloxy)carbamoyl]-4-(3-pyridyl)-3-butenyl]-2'-(methanesulphonyl)-4-methyl-2'-phenylvalerohydrazide in the form of a white solid.

MS: 559 (M+H)+.

EXAMPLE 65

2(R)-[1(S)-(Hydroxycarbamoyl)-4-(3-pyridyl)butyl]-2'-isobutyl-2'-(methanesulphonyl)-4-methylvalerohydrazide A solution of 0.33 g of 2(R)-[1(S)-[(benzyloxy) carbamoyl]-4-(3-pyridyl)butyl]-2'-isobutyl-2'-(methanesulphonyl)-4-methylvalerohydrazide in 10 ml of methanol was hydrogenated in the presence of 80 mg of 10% palladium-on-carbon for 1.5 hours. The catalyst was removed by filtration and the solvent was evaporated. The residue was triturated with diethyl ether to give 0.26 g of 2(R)-[1(S)-(hydroxycarbamoyl)-4-(3-pyridyl)butyl]-2'-isobutyl-2'-(methanesulphonyl)-4-methylvalerohydrazide in the form of a white solid.

MS: 457 (M+H)+.

HPLC: Gradient elution using solvent A containing 5% solvent B increasing to 95% solvent B over 15 minutes; flow rate 1 ml/minute. Retention time: 9.59 minutes. Solvent A: $H_2O$/0.1% TFA; solvent B: $CH_3CN$/0.085% TFA. Column type: HYPERPEP 300A.

The 2(R)-[1(S)-[(benzyloxy)carbamoyl]-4-(3-pyridyl)butyl-2'-isobutyl-2'-(methanesulphonyl)-4-methylvalerohydrazide used as the starting material was prepared as follows:

(i) A solution of 1.71 g of (E)-1,2-dibenzyl 1-tert-butyl-4-methyl-1-[3-(3-pyridyl)-prop-2-en-1-yl]-1(RS),1,2 (R)-pentanetricarboxylate in 35 ml of isopropanol was hydrogenated over 400 mg of 10% palladium-on-carbon for 5 hours. The catalyst was removed by filtration and the solvent was evaporated. Final traces of isopropanol were removed by the addition and evaporation of toluene (2×10 ml). The residue was refluxed for 2 hours in a mixture of 40 ml of toluene and 0.42 ml of triethylamine and the solvent was removed by evaporation to give a red oil. The oil in 10 ml of dichloromethane was cooled to 0° C. while stirring under nitrogen and then 0.95 ml of N-ethylmorpholine was added followed by 0.49 g of 1-hydroxybenzotriazole and 0.72 g of 1-ethyl-3-(3-dimethylaminopropyl)-carbodiimide hydrochloride. After stirring for 15 minutes at 0° C. the solution was treated with 0.98 g of isobutylhydrazine tosylate salt and the mixture was left to come to room temperature and then stirred overnight. The solvent was evaporated and the residue was partitioned between ethyl acetate and water. The ethyl acetate layer was washed with water, 5% sodium hydrogen carbonate solution and brine and then dried over anhydrous magnesium sulphate and evaporated. Chromatography on silica gel using dichloromethane/methanol (19:1), for the elution followed by evaporation yielded 0.63 g of 2(R)-[1(S)-(tert-butoxycarbonyl)-4-(3-pyridyl)butyl]-2'-isobutyl-4-methylvalerohydrazide as a white solid.

MS: 420 (M+H)+.

(ii) In an analogous manner to that described in Example 1, part (ii), starting from 0.62 g of 2(R)[1(S)-(tert-butoxycarbonyl)-4-(3-pyridyl)butyl]-2'-isobutyl-4-methylvalerohydrazide there was obtained 0.68 g of 2(R)-[1(S)-(tert-butoxycarbonyl)-4-(3-pyridyl)butyl]-2'-isobutyl-2'-(methanesulphonyl)-4-methylvalerohydrazide in the form of a solid.

MS: 498 (M+H)+.

(iii) In an analogous manner to that described in Example 1, part (iii), starting from 0.68 g of 2(R)[1(S)-(tert-butoxycarbonyl)-4-(3-pyridyl)butyl]-2'-isobutyl-2'-(methanesulphonyl)-4-methylvalerohydrazide there were obtained 0.55 g of 2(R)-[1(S)-(carboxy)-4-(3-pyridyl)butyl]-2'-isobutyl-2'-(methanesulphonyl)-4-methylvalerohydrazide

MS: 442 (M+H)+.

(iv) The carboxylic acid prepared in paragraph (iii) was dissolved in 3 ml of dimethylformamide, cooled to 0° C. and treated in succession with 0.45 g of O-benzyl-hydroxylamine and 0.26 g of 1-ethyl-3-(3-dimethylaminopropyl)-carbodiimide hydrochloride. The mixture was left to come to room temperature and was stirred overnight. The solvent was evaporated and the residue was partitioned between water and ethyl acetate. The ethyl acetate layer was washed with water and with 5% sodium hydrogen carbonate solution, dried over anhydrous magnesium sulphate and evaporated. The resulting gum was triturated with diethyl ether to give 0.34 g of 2(R)-[1(S)-[(benzyloxy) carbamoyl]-4-(3-pyridyl)butyl]-2'-isobutyl-isobutyl-2'-(methanesulphonyl)-4-methylvalerohydrazide in the form of a white solid.

MS: 547 (M+H)+.

EXAMPLE 66

(E)-2(R)-[1(S)-(Hydroxycarbamoyl)-4-(4-methoxyphenyl)-3-butenyl]-2'-(methanesulphonyl)-4-methyl-2'-phenylvalerohydrazide In an analogous manner to that described in the first paragraph of Example 2, starting from 0.079 g of (E)-2(R)-[(tetrahydro-2(RS)-pyranyloxy)carbamoyl]-4-(4-methoxyphenyl)-3-butenyl]-2'-(methanesulphonyl)-4-methyl-2'-phenylvalerohydrazide there was obtained 0.041g of (E)-2(R)-[1(S)-(hydroxycarbamoyl)-4-(4-methoxyphenyl)-3-butenyl]-2'-(methanesulphonyl)-4-methyl-2'-phenylvalerohydrazide in the form of a white solid.

MS: 504 (M+H)+.

HPLC: Gradient elution using solvent A containing 5% solvent B increasing to 95% solvent B over 15 minutes; flow rate 1 ml/minute. Retention time 11.22 minutes. Solvent A: H$_2$O; solvent B: CH$_3$ CN.

Column type: HYPERPEP 300A.

The (E)-2(R)-[(tetrahydro-2(RS)-pyranyloxy)carbamoyl]-4-(4-methoxyphenyl)-3-butenyl]-2'-(methanesulphonyl)4-methyl-2'-phenylvalerohydrazide used as the starting material was prepared as follows:

In an analogous manner to that described in Example 64, parts (i)–(vi), starting from 1,2-dibenzyl 1-tert-butyl-4-methyl-1(RS),1,2(R)-pentanetricarboxylate and 4-(4-methoxyphenyl)-allyl acetate there was obtained (E)-2(R)-[(tetrahydro-2(RS)-pyranyloxy)carbamoyl]-4-(4-methoxyphenyl)-3-butenyl]-2'-(methanesulphonyl)-4-methyl-2'-phenylvalerohydrazide in the form of an off-white solid.

MS: 588 (M+H)+.

EXAMPLE 67

2(R)-[4-Cyclohexyl-1(S-(hydroxycarbamoyl)-butyl]-2'-isobutyl-2'-(methanesulphonyl)-4-methylvalerohydrazide In a manner analogous to that described in the first paragraph of Example 2, starting from 0.17 g of 2(R)-[4-cyclohexyl-1(S)-[(tetrahydro-2(RS)-pyranyloxy)carbamoyl]-butyl]-2'-isobutyl-2'-(methanesulphonyl)-4-methylvalerohydrazide there was obtained 0.11 g of 2(R)-[4-cyclohexyl-1(S)-(hydroxycarbamoyl)-butyl]-2'-isobutyl-2'-(methanesulphonyl)-4-methylvalerohydrazide in the form of a white solid.

MS: 462 (M+H)+.

HPLC: Gradient elution using solvent A containing 5% solvent B increasing to 95% solvent B over 15 minutes; flow rate 1 ml/minute. Retention time 13.82 minutes. Solvent A: H$_2$O; solvent B: CH$_3$ CN.

Column type: HYPERPEP 300A

The 2(R)-[4-cyclohexyl-1(S)-[(tetrahydro-2(RS)-pyranyloxy)carbamoyl]-butyl]-2'-isobutyl-2'-(methanesulphonyl)-4-methylvalerohydrazide used as the starting material was prepared as follows.

(i) A solution of 1.0 g of 2(R)-[1(S)-(tert-butoxycarbonyl)-4-phenylbutyl]-4-methylvaleric acid in 30 ml of acetic acid was hydrogenated over 300 mg of platinum oxide for 1.5 hours. The catalyst was removed by filtration and the solvent was evaporated. Final traces of acetic acid were removed by the addition and evaporation of toluene (3×10 ml). Chromatography on silica gel using diethyl ether/hexane (1:7) for the elution followed by evaporation yielded 0.67 g of 2(R)-[1(S)-(tert-butoxycarbonyl)-4-cyclohexyl-butyl]-4-methylvaleric acid as a white solid.

TLC: methanol/dichloromethane (1:19): Rf 0.51.

(ii) In an analogous manner to that described in Example 1, part (i), starting from 0.66 g of 2(R)[1(S)-(tert-butoxycarbonyl-4-cyclohexyl-butyl]-4-methylvaleric acid there was obtained 0.27 g of 2(R)-[1(S)-(tert-butoxycarbonyl)-4-(4-cyclohexyl)butyl]-2'-isobutyl-4-methylvalerohydrazide in the form of a white solid (from hexane).

MS: 425 (M+H)+.

(iii) In an analogous manner to that described in Example 1, part (ii), starting from 0.26 g of 2(R)[1(S)-(tert-butoxycarbonyl)-4-(4-cyclohexyl)butyl]-2'-isobutyl-4-methylvalerohydrazide there was obtained 0.31 g of 2(R)-[1(S)-(tert-butoxycarbonyl)-4-(4-cyclohexyl)butyl]-2'-isobutyl-2'-(methanesulphonyl)-4-methylvalerohydrazide.

MS: 503 (M+H)+.

(iii) In an analogous manner to that described in Example 1, part (iii), starting from 0.30 g of 2(R)[1(S)-(tert-butoxycarbonyl)-4-(4-cyclohexyl)butyl]-2'-isobutyl-2'-(methanesulphonyl)-4-methylvalerohydrazide there was obtained 0.24 g of 2(R)-[1(S)-(carboxy)-4-(4-cyclohexyl)butyl]-2'-isobutyl-2'-(methanesulphonyl)-4-methylvalerohydrazide.

MS: 447 (M+H)+.

(vi) The carboxylic acid prepared in paragraph (v) was dissolved in 3 ml of dimethylformamide, cooled to 0° C. and treated in succession with 0.19 g of O-(tetrahydro-2H-pyran-2(RS)-yl)hydroxylamine and 0.113 g of 1-ethyl-3-(3-dimethylaminopropyl)carbodiimide hydrochloride. The mixture was left to come to room temperature and was stirred overnight. The solvent was evaporated and the residue was partitioned between water and ethyl acetate. The ethyl acetate layer was washed with water, 5% sodium hydrogen carbonate solution and brine, dried over anhydrous magnesium sulphate and evaporated. The resulting solid was triturated with diethyl ether to give 0.18 g of 2(R)-[4-cyclohexyl-1(S)-[(tetrahydro-2(RS)-pyranyloxy)carbamoyl]-butyl]-2'-isobutyl-2'-(methanesulphonyl)-4-methylvalerohydrazide in the form of a white solid.

MS: 546 (M+H)+.

EXAMPLE 68

(E)-2(R)-[1(S)-(Hydroxycarbamoyl)-4-(4-(methoxycarbonyl)phenyl)-3-butenyl]-2'-(methanesulphonyl)-4-methyl-2'-phenylvalerohydrazide In an analogous manner to that described in the first paragraph of Example 2, starting from 0.110 g of (E)-2(R)-[1(S)-[(tetrahydro-2(RS)-pyranyloxy)carbamoyl]-4-(4-(methoxycarbonyl)phenyl)-3-butenyl]-2'-(methanesulphonyl)-4-methyl-2'-phenylvalerohydrazide there was obtained 0.059 g of (E)-2(R)-[1(S)-(hydroxycarbamoyl)-4-(4-(methoxycarbonyl)phenyl)-3-butenyl]-2'-(methanesulphonyl)-4-methyl-2'-phenylvalerohydrazide in the form of a white solid.

MS: 532 (M+H)+.

HPLC: Gradient elution using solvent A containing 5% solvent B increasing to 95% solvent B over 15 minutes; flow rate 1 ml/minute. Retention time 12.09 minutes. Solvent A: H$_2$O; solvent B: CH$_3$CN.

Column type: HYPERPEP 300A.

The (E)-2(R)-[1(S)-[(tetrahydro-2(RS)-pyranyloxy)carbamoyl]-4-(4-(methoxycarbonyl)phenyl)-3-butenyl]-2'-(methanesulphonyl)-4-methyl-2'-phenylvalerohydrazide used as the starting material was prepared as a white solid in a manner analogous to Example 2 (i)–(v), but replacing the cinnamyl bromide in step (i) by 4-methoxycarbonyl-cinnamyl bromide.

MS: 616 (M+H)+.

EXAMPLE 69

(E)-2(R)-[1(S)-(Hydroxycarbamoyl)-4-(4-nitrophenyl)-3-butenyl]-2'-(methanesulphonyl)-4-methyl-2'-phenylvalerohydrazide.

A solution of 0.080 g of (E)-2(R)-[1(S)-[(tetrahydro-2(RS)-pyranyloxy)carbamoyl]-4-(4-nitrophenyl)-3-butenyl]-

2'-(methanesulphonyl)-4-methyl-2'-phenylvalerohydrazide in a mixture of 3 ml of methanol and 1.5 ml of dichloromethane was treated with 0.020 g of 4-toluenesulphonic acid. The mixture was stirred for 5 hours at room temperature and the solution was evaporated. The resulting gum was triturated with diethyl ether to give 0.063 g of (E)-2(R)-[1(S)-(hydroxycarbamoyl)-4-(4-nitrophenyl)-3-butenyl]-2'-(methanesulphonyl)-4-methyl-2'-phenylvalerohydrazide in the form of a light-brown solid.
MS: 519 (M+H)$^+$.

HPLC: Gradient elution using solvent A containing 5% solvent B increasing to 95% solvent B over 15 minutes; flow rate 1 ml/minute. Retention time 12.07 minutes. Solvent A: H$_2$O; solvent B: CH$_3$CN.
Column type: HYPERPEP 300A The (E)-2(R)-[1(S)-[(tetrahydro-2(RS)-pyranyloxy)carbamoyl]-4-(4-nitrophenyl)-3-butenyl]-2'-(methanesulphonyl)-4-methyl-2'-phenylvalerohydrazide used as the starting material was prepared as a white solid in a manner analogous to Example 64 (i)–(vi), but replacing 4-(3-pyridyl)allyl acetate and tetrakis(triphenylphosphine)palladium(0) in step (i) by 4-nitro-cinnamyl bromide.
MS: 603 (M+H)$^+$.

EXAMPLE 70

(E)-2(R)-[1(S)-(Hydroxycarbamoyl)-4-phenyl-3-butenyl]-2'-(methanesulphonyl)-4-methyl-2'-](morpholinocarbonyl)methyl]valerohydrazide In a manner analogous to that described in the first paragraph of Example 2, starting from 0.1 g of (E)-2(R)-[1(S)-[(tetrahydro-2(RS)-pyranyloxy)carbamoyl]-4-phenyl-3-butenyl]-2'-(methanesulphonyl)-4-methyl-2'-](morpholinocarbonyl)methyl]valerohydrazide there was obtained 0.08 g of (E)-2(R)-[1(S)(Hydroxycarbamoyl)-4-phenyl-3-butenyl]-2'-(methanesulphonyl)-4-methyl-2'-[(morpholinocarbonyl)methyl]valerohydrazide in the form of a white solid.
MS: 525 (M+H)$^+$.

nmr (d$_6$ DMSO): 10.52 (1H,s); 10.47 (1H, s); 8.82 (1H, s); 7.35–7.25 (4H, m); 7.23–7.17 (1H, m); 6.28 (1H,d,J=15.5 Hz); 6.09–5.98 (1H, m); 4.40–4.26 (2H, m); 3.64–3.30 (8H, m); 3.15 (3H, s); 2.63–2.54 (1H, m); 2.37–2.08 (3H, m); 1.50–1.28 (2H, m); 0.98–0.89 (1H, m); 0.78 (6H, m).

HPLC: Gradient elution using solvent A containing 5% solvent B increasing to 95% solvent B over 15 minutes, flow rate 1 ml/minute. Retention time: 10.19 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and N-bromoacetylmorpholine.
MS: 609 (M+H)$^+$.

EXAMPLE 71

(E)-2(R)-[1(S)-Hydroxycarbamoyl)-4-phenyl-3-butenyl]-2'-(methanesulphonyl)-4-methyl-2'-(2morpholinoethyl)valerohydrazide In a manner analogous to that described in the first paragraph of Example 2, after washing the ethyl acetate solution of the product with sodium hydrogen carbonate solution in order to obtain the free base, from 0.13 g of (E)-2(R)-[1(S)-[(tetrahydro-2(RS)-pyranyloxy)carbomoyl]-4-phenyl-3-butenyl]-2'-(methanesulphonyl)-4-methyl-2'-(2-morpholinoethel)valerohydrazide there was obtained 0.1 g of (E)-2(R)-[1(S)-(hydroxycarbamoyl)-4-phenyl-3-butenyl]-2'-(methanesulphonyl)-4-methyl-2'-(2-morpholinoethyl)valerohydrazide in the form of a white solid.
MS: 511 (M+H)$^+$.

HPLC: Gradient elution using solvent A containing 5% solvent B increasing to 95% solvent B over 15 minutes; flow rate 1 ml/minute. Retention time: 10.71 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-2'-(methanesulphonyl)-4-methylvalerohydrazide and 4-(2-chloroethyl)morpholine.
MS: 595 (M+H)$^+$.

EXAMPLE 72

Methyl (E)-2-[2-[2(R)-[1(S)-(hydroxycarbamoyl)-4-phenyl-3-butenyl]-4-methylvaleryl]-1-[(methylsulphonyl)hydrazino]acetate In a manner analogous to that described in the first paragraph of Example 2, starting from 0.12 g of methyl (E)-2-[2-[2(R)-[1(S)-[(tetrahydro-2-(RS)-pyranyloxy)carbamoyl]-4-phenyl-3-butenyl]-4-methylvaleryl]-1-(methylsulphonyl)hydrazino]acetate there was obtained 0.09 g of methyl (E)-2-[2-[2(R)-[1(S)-(hydroxycarbamoyl)-4-phenyl-3-butenyl]-4-methylvaleryl]-1-[(methanesulphonyl)hydrazino]acetate in the form of a white solid.
MS: 470 (M+H)$^+$.

nmr (d$_6$ DMSO): 10.77 (1H, s); 10.53 (1H, m); 8.83 (1H, m); 7.35–725 (4H, m); 7.22–7.16 (1H, m); 6.27 1H,d, J=15.5 Hz);6.08–5.99 (1H, m); 4.41–4.17 (2H, m); 3.66 (3H, s); 3.14 (3H, s); 2.62–2.53 (1H, m); 2.35–2.07 (3H, m); 1.50–1.40 (1H, m); 1.38–1.25 (1H, m); 1.00–0.92 (1H, m); 0.79 (6H, m).

HPLC: Gradient elution using solvent A containing 5% solvent B increasing to 95% solvent B over 15 minutes; flow rate 1 ml/minute. Retention time 10.93 minutes. Solvent A: H$_2$O/0.1% TFA; solvent B: CH$_3$CN/0.085% TFA. Column type: HYPERPEP 300A The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and methylbromoacetate.
MS: 554 (M+H)$^+$.

EXAMPLE 73

(E)-2-(R)-[1(S)-(Hydroxycarbamoyl)-4-phenyl-3-butenyl]-2'-(methanesulphonyl)-4-methyl-2'-(3-phenylpropyl)valerohydrazide In a manner analogous to that described in the first paragraph of Example 2, starting from 0.166 g of (E)-2(R)-[1(S)-[(tetrahydro-2(RS)-pyranyloxy)carbamoyl]-4-phenyl-3-butenyl]-2'-(methanesulphonyl)-4-methyl-2'-(3-phenylpropyl)valerohydrazide there was obtained 0.091g of (E)-2(R)-[1(S)-(hydroxycarbamoyl)-4-phenyl-3-butenyl]-2'-(methanesulphonyl)-4-methyl-2'-(3-phenylpropyl)valerohydrazide in the form of an off-white solid.
MS: 516 (M+H)$^+$.

HPLC: Gradient elution using solvent A containing 5% solvent B increasing to 95% solvent B over 15 minutes; flow rate 1 ml/minute. Retention time: 13.01 and 13.19 minutes (double peak). Solvent A: H$_2$O/0.1% TFA; solvent B: CH$_3$CN/0.085% TFA. Column type: HYPERPEP 300A The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 1-bromo-3-phenylpropane.
MS: 600 (M+H)$^+$.

EXAMPLE 74

(E)-2(R)-[1(S)-(Hydroxycarbamoyl)-4-phenyl-3-butenyl]-2'-(methanesulphonyl)-4-methyl-2'-[(2-naphthyl)methyl]valerohydrazide In a manner analogous to that described in the first paragraph of Example 2, starting from 0.156 g of (E)-2(R)-[1(S)-[(tetrahydro-2(RS)-pyranyloxy)carbamoyl]-4-phenyl-3-butenyl]-2'-(methanesulphonyl)-4-methyl-2'-[(2-naphthyl)methyl]valerohydrazide there was obtained 0.109 g of (E)-2(R)-[1(S)-(hydroxycarbamoyl)-4-phenyl-3-butenyl]-2'-(methanesulphonyl)-4-methyl-2-[(2'-[(2-naphthyl)methyl]valerohydrazide in the form of an off-white solid.
MS: 538 (M+H)$^+$.

HPLC: Gradient elution using solvent A containing 5% solvent B increasing to 95% solvent B over 15 minutes; flow rate 1 ml/minute. Retention time: 13.09 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methyl-2'-[(2-naphthyl)methyl]valerohydrazide and 2-bromomethylnaphthalene
MS: 622 (M+H)$^+$.

EXAMPLE 75

(E)-2(R)-[1(S)-(Hydroxycarbamoyl)-4-phenyl-3-butenyl]-2'-(methanesulphonyl)-2'-(methoxyethyl)-4-methylvalerohydrazide In a manner analogous to that described in the first paragraph of Example 2, starting from 0.133 g of (E)-2(R)-[1(S)-[(tetrahydro-2(RS)-pyranyloxy)carbamoyl]-4-phenyl-3-butenyl]-2-(methanesulphonyl)-2'-(2-methoxyethyl)-4-methylvalerohydrazide there was obtained 0.073 g of (E)-2(R)-[(S)-(hydroxycarbamoyl)-4-phenyl-3-butenyl]-2'-(methanesulphonyl)-2'-2-methoxyethyl)-4-methylvalerohydrazide in the form of an off-white solid.
MS: 456 (M+H)$^+$.

HPLC: Gradient elution using solvent A containing 5% solvent B increasing to 95% solvent B over 15 minutes; flow rate 1 ml/minute. Retention time: 10.67 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 2-bromoethyl methyl ether.
MS: 540 (M+H)$^+$.

EXAMPLE 76

(E)-2(R)-[1(S)-(Hydroxycarbamoyl)-4-phenyl-3-butenyl]-2'-(2-hydroxyethyl)-2'-(methanesulphonyl)-4-methylvalerohydrazide In a manner analogous to that described in the first paragraph of Example 2, starting from 0.148 g of (E)-2(R)-[1(S)-[(tetrahydro-2(RS)-pyranyloxy)carbamoyl]-4-phenyl-3-butenyl]-2'-(2-hydroxyethyl)-2'-(methanesulphonyl)-4-methylvalerohydrazide there was obtained 0.041 g of (E)-2(R)-[1(S)-(hydroxycarbamoyl)-4-phenyl-3-butenyl]-2'-(2-hydroxyethyl)-2'-(methanesulphonyl)-4-methylvalerohydrazide in the form of a cream solid.
MS: 442 (M+H)$^+$.

HPLC: Gradient elution using solvent A containing 5% solvent B increasing to 95% solvent B over 15 minutes; flow rate 1 ml/minute. Retention time: 10.06 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 2-bromoethanol.
MS: 526 (M+H)$^+$.

EXAMPLE 77

(E)-2(R)-[1(S)-(droxycarbamoyl)-4-phenyl-3-butenyl]-2'-(methanesulphonyl)-4-methyl-2'-[(4-pyridyl)methyl]valerohydrazide p-toluenesulphonate In a manner analogous to that described in the first paragraph of Example 2, starting from 0.097 g of (E)-2(R)-[1(S)-[(tetrahydro-2(RS)-pyranyloxy)carbamoyl]-4-phenyl-3-butenyl]-2'-(methanesulphonyl)-4-methyl-2'-[(4-pyridyl)methyl]valerohydrazide there was obtained 0.077 g of (E)-2(R)[1(S)-(hydroxycarbamoyl)-4-phenyl-3-butenyl]-2'-(methanesulphonyl)-4-methyl-2'-[(4-pyridyl)methyl]valerohydrazide p-toluenesulphonate in the form of an off-white solid.
MS: 489 (M+H)$^+$.

HPLC: Gradient elution using solvent A containing 5% solvent B increasing to 95% solvent B over 15 minutes; flow rate 1 ml/minute. Retention time: 9.59 minutes. Solvent A: H$_2$O/0.1% TFA; solvent B: CH$_3$CN/0.085% TFA. Column type HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-methanesulphonyl)-4-methylvalerohydrazide and 4-bromomethylpyridine hydrobromide.
MS: 573 (M+H)$^+$.

EXAMPLE 78

(E)-2'-(Cyclopropylmethyl)-2(R)-[1(S)-(hydroxycarbamoyl)-4-phenyl-3-butenyl]-2'-(methanesulphonyl)-4-methylvalerohydrazide In an analogous manner to that described in the first paragraph of Example 2, starting from 0.13 g of (E)-2'-cyclopropylmethyl-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.092 g of (E)-2'-(cyclopropylmethyl)-2(R)-[1(S)-(hydroxycarbamoyl)-4-phenyl-3-butenyl]-2'-(methanesulphonyl)-4-methylvalerohydrazide in the form of a white solid.
MS: 452 (M+H)$^+$.

HPLC: Gradient elution using solvent A containing 5% solvent B increasing to 95% solvent B over 15 minutes; flow rate 1 ml/minute. Retention time 11.47 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and cyclopropylmethyl bromide.

EXAMPLE 79

(E)-2(R)-[1(S)-(Hydroxycarbamoyl)-4-phenyl-3-butenyl]-2'-(methanesulphonyl)-4-methyl-2'-[2(S)-methylbutyl]valerohydrazide.

In a manner analogous to that described in the first paragraph of Example 2, starting from 0.135 g of (E)-2(R)-[1(S)-[(tetrahydro-2-(RS)-pyranyloxy)carbamoyl]-4-phenyl-3-butenyl]-2'-(methanesulphonyl)-4-methyl-2'-[2(S)-methylbutyl]valerohydrazide there was obtained 0.101 g of (E)-2(R)-[1(S)-(hydroxycarbamoyl)-4-phenyl-3-butenyl]-2'-(methanesulphonyl)-4-methyl-2'-[2(S)-methylbutyl]valerohydrazide in the form of a white solid.
MS: 468 $(M+H)^+$.

HPLC: Gradient elution using solvent A containing 5% solvent B increasing to 95% solvent B over 15 minutes; flow rate 1 ml/minute. Retention time: 12.70 minutes. Solvent A: $H_2O/0.1\%$ TFA; solvent B: $CH_3CN/0.085\%$ TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and (S)-(+)-1-bromo-2-methylbutane.

EXAMPLE 80

(E)-2(R)-[1(S)-(Hydroxycarbanoyl)-4-phenyl-3-butenyl]-2'-[3-hydroxy-2(R)-methylpropyl]-2'-(methanesulphonyl)-4-methylvalerohydrazide In a manner analogous to that described in the first paragraph of Example 2, starting from 0.13 g of (E)-2(R)-[1(S)-[(tetrahydro-2-(RS)-pyranyloxy)carbamoyl]-4-phenyl-3-butenyl]-2'-[3-hydroxy-2(R)-methylpropyl]-2'-(methanesulphonyl)-4-methylvalerohydrozide there was obtained 0.095 g of (E)-2(R)-[1(S)-(hydroxycarbamoyl)-4-phenyl-3-butenyl-2'-[3-hydroxy-2(R)-methylpropyl]-2'-(methanesulphonyl)-4-methylvalerohydrazide in the form of a white solid.
MS: 470 $(M+H)^+$.

HPLC: Gradient elution using solvent A containing 5% solvent B increasing to 95% solvent B over 15 minutes; flow rate 1 ml/minute. Retention time: 10.20 minutes. Solvent A: $H_2O/0.01\%$ TFA; solvent B: $CH_3CN/0.085\%$ TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrozide and (S)-(+)-3-bromo-2-methyl-1-propanol.

EXAMPLE 81

(E)-2(R)-[1(S)-(Hydroxycarbamoyl)-4-phenyl-3-butenyl]-2'-[3-hydroxy-2(S)-methylpropyl]-2'-(methanesulphonyl)-4-methylvalerohydrozide In a manner analogous to that described in the first paragraph of Example 2, starting from 0.13 g of (E)-2(R)-[1(S)-[(tetrahydro-2(RS)-pyranyloxy)carbamoyl-4-phenyl-3-butenyl-2'-[3-hydroxy-2(S)-methylpropyl]-2'-(methanesulphonyl)-4-methylvalerohydrazide there was obtained 0.09 g of (E)-2(R)-[1(S)-(hydroxycarbamoyl)-4-phenyl-3-butenyl]-2'-[3-hydroxy-2(S)-methylpropyl-2'-(methanesulphonyl)-4-methylvalerohydrazide in the form of a white solid.
MS: 470 $(M-H)^+$.

HPLC: Gradient elution using solvent A containing 5% solvent B increasing to 95% solvent B over 15 minutes; flow rate 1 ml/minute. Retention time: 10.11 minutes. Solvent A: $H_2O/0.1\%$ TFA; solvent B: $CH_3CN/0.085\%$ TFA. Column type: HYPERPEP 300A The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and (R)-(−)-3-bromo-2-methyl-1-propanol.

EXAMPLE 82

(E)-2(R)-[1(S)-(Hydroxycarbamoyl)-4-phenyl-3-butenyl]-2'-isopentyl-2'-(methanesulphonyl)-4-methylvalerohydrazide In a manner analogous to that described in the first paragraph of Example 2, starting from 0.12 g of (E)-2(R)-[1(S)-[(tetrahydro-2(RS)-pyranyloxy)carbamoyl]-4-phenyl-3-butenyl]-2'-isopentyl-2'-(methanesulphonyl)-4-methylvalerohydrazide there was obtained 0.08 g of (E)-2(R)-[1(S)-(hydroxycarbamoyl)-4-phenyl-3-butenyl]-2'-isopentyl-2'-(methanesulphonyl)-4-methylvalerohydrazide in the form of a white solid.
MS: 468 $(M+H)^+$.

HPLC: Gradient elution using solvent A containing 5% solvent B increasing to 95% solvent B over 15 minutes; flow rate 1 ml/minute. Retention time: 12.63 minutes. Solvent A: $H_2O/0.1\%$ TFA; Solvent B: $CH_3CN/0.085\%$ TFA. Column type: HYPERPEP 300A The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 1-bromo-3-methylbutane.

EXAMPLE 83

(E)-2'-(Cyclobutylmethyl)-2(R)-[(S)-(hydroxycarbamoyl)-4-phenyl-3-butenyl]-2'-(methanesulphonyl)-4-methylvalerohydrazide In a manner analogous to that described in the first paragraph of Example 2, starting from 0.13 g of (E)-2'-(cyclobutylmethyl)-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.075 g of (E)-2'-(cyclobutylmethyl)-2(R)-[1(S)-(hydroxycarbamoyl)-4-phenyl-3-butenyl]-2'-(methanesulphonyl)-4-methylvalerohydrazide in the form of a white solid.
MS: 466 $(M+H)^+$.

HPLC: Gradient elution using solvent A containing 5% solvent B increasing to 95% solvent B over 15 minutes; flow rate 1 ml/minute. Retention time: 12.34 minutes. Solvent A: $H_2O/0.1\%$ TFA; solvent B: $CH_3CN/0.085\%$ TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and cyclobutylmethyl bromide.

EXAMPLE 84

(E)-2(R)-[1(S)-(Hydroxycarbamoyl)4-phenyl-3-butenyl]-2'-(methanesulphonyl)-4-methyl-2'-(3-methyl-2-butenyl)valerohydrazide In a manner analogous to that described in the first paragraph of Example 2, starting from 0.222 g of (E)-2(R)-[1(S)-[(tetrahydro-2(RS)-pyranyloxy)carbamoyl]-4-phenyl-3-butenyl-2'-(methanesulphonyl)-4-methyl-2'-(3-methyl-2-butenyl)valerohydrazide there was obtained 0.137 g of (E)-2(R)-[1(S)-(hydroxycarbamoyl)-4-phenyl-3-butenyl]-2'-(methanesulphonyl)-4-methyl-2'-(3-methyl-2-butenyl)valerohydrazide in the form of a white solid.
MS: 466 (M+H)$^+$.

HPLC: Gradient elution using solvent A containing 5% solvent B increasing to 95% solvent B over 15 minutes; flow rate 1 ml/minute. Retention time: 11.95 minutes. Solvent A: H$_2$O/0.1% TFA; Solvent B: CH$_3$CN/0.085% TFA. Column type: HYPERPEP 300A.

The starting material was prepared in an analogous manner to that described in Example 15, part (iii), starting from (E)-2-(R)-[1(S)-[(tetrahydro-2(RS)-pyranyloxy)carbamoyl]-4-phenyl-3-butenyl-2'-(methanesulphonyl)-4-methylvalerohydrazide and 3,3-dimethylallyl bromide.

EXAMPLE 85

(E)-2'-Benzyl-2'-(butanesulphonyl)-2(R)-[1(S)-(hydroxycarbamoyl)-4-phenyl-3-butenyl]-4-methylvalerohydrazide In a manner analogous to that described in the first paragraph of Example 2, starting from 0.17 g of (E)-2'-benzyl-2'-(butanesulphonyl)-2(R)-[1(S)-[(tetrahydro-2(RS)-pyranyloxy)carbamoyl]-4-phenyl-3-butenyl]-4-methylvalerohydrazide there was obtained 0.115 g of (E)-2'-benzyl-2'-(butanesulphonyl)-2(R)-[1(S)-hydroxycarbamoyl)-4-phenyl-3-butenyl]-4-methylvalerohydrazide in the form of a white solid.
MS: 530 (M+H)$^+$.

HPLC: Gradient elution using solvent A containing 5% solvent B increasing to 95% solvent B over 15 minutes; flow rate 1 ml/minute. Retention time: 13.83 minutes. Solvent A: H$_2$O/0.1% TFA; solvent B: CH$_3$CN/0.085% TFA. Column type: HYPERPEP 300A.

The starting material was prepared as follows:

(i) In a manner analogous to that described in Example 1, part (ii), starting from 0.54 g of (E)-2(R)-[1(S)-(tert-butoxycarbonyl)-4-phenyl-3-butenyl]-4-methylvalerohydrazide and 1-butanesulphonyl chloride there was obtained 0.425 g of (E)-2'-(butanesulphonyl)-2(R)-[1(S)-(tert-butoxycarbonyl)-4-phenyl-3-butenyl]-4-methylvalerohydrazide in the form of a white foam.
MS: 481(M+H)$^+$.

(ii) In a manner analogous to that described in Example 15, part (iii), starting from 0.416 g of (E)-2'-(butanesulphonyl)-2(R)-[1(S)-(tert-butoxycarbonyl)-4-phenyl-3-butenyl]-4-methylvalerohydrazide and benzyl bromide there was obtained 0.463 g of (E)-2'-benzyl-2'-(butanesulphonyl)-2(R)-[1(S)-(tertbutoxycarbonyl)-4-phenyl-3-butenyl]-4-methylvalerohydrazide in the form of a pale yellow gum.
MS: 571 (M+H)$^+$.

(iii) In a manner analogous to that described in Example 1, part (iii), followed by that described in Example 2, part (v), starting from 0.46 g of (E)-2'-benzyl-2'-(butanesulphonyl)-2(R)-[1(S)-(tertbutoxycarbonyl)-4-phenyl-3-butenyl]-4-methylvalerohydrazide there was obtained 0.174 g of (E)-2'-benzyl-2'-(butanesulphonyl)-2(R)-[1(S)-[(tetrahydro-2(RS)-pyranyloxycarbonyl]-4-phenyl-3-butenyl]-4-methylvalerohydrazide in the form of a white solid.
MS: 614 (M+H)$^+$.

EXAMPLE 86

(E)-2(R)-[1(S)-(Hydroxycarbamoyl)-4-phenyl-3-butenyl]-2'-(methanesulphonyl)-4-methyl-2'-(2-methylallyl)valerohydrazide In a manner analogous to that described in the first paragraph of Example 2, starting from 0.14 g of (E)-2(R)-[1(S)-[(tetrahydro-2(RS)-pyranyloxy)carbamoyl]-4-phenyl-3-butenyl]-2'-(methanesulphonyl)-4-methyl-2'-(2-methylallyl)valerohydrazide there was obtained 0.063 g of (E)-2(R)-[1(S)-(hydroxycarbamoyl)-4-phenyl-3-butenyl]-2'-(methanesulphonyl)-4-methyl-2'-(2-methylallyl)valerohydrozide in the form of an off-white solid.
MS: 452 (M+H)$^+$.

HPLC: Gradient elution using solvent A containing 5% solvent B increasing to 95% solvent B over 15 minutes; flow rate 1 ml/minute. Retention time 11.75 minutes. Solvent A: H$_2$O/0.1% TFA; solvent B: CH$_3$CN/0.085% TFA. Column type: HYPERPEP 300A.

The starting material was prepared in an analogous manner to that described in Example 15. part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and methylallyl chloride.

EXAMPLE 87

(E)-2'-(2-Cyclohexylethyl)-2(R)-[1(S)-(hydroxycarbamoyl)-4-phenyl-3-butenyl]-2'-(methanesulphonyl)-4-methylvalerohydrazide In a manner analogous to that described in the first paragraph of Example 2, starting from 0.183 g of (E)-2'-(2-cyclohexylethyl)-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.12 g of (E)-2'-(2-cyclohexylethyl)-2(R)-[1(S)-(hydroxycarbamoyl)-4-phenyl-3-butenyl]-2'-(methanesulphonyl)-4-methylvalerohydrazide in the form of a white solid.
MS: 508 (M+H)$^+$.

HPLC: Gradient elution using solvent A containing 5% solvent B increasing to 95% solvent B over 15 minutes; flow rate 1 ml/minute. Retention time: 13.93 and 14.02 minutes (double peak). Solvent A: H$_2$O/0.1% TFA; solvent B: CH$_3$CN/0.085% TFA; Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 2-cyclohexylethyl bromide.

EXAMPLE 88

(E)-2(R)-[1(S)-(Hydroxycarbamoyl)-4-phenyl-3-butenyl]-2'-[2-(3-indolyl)ethyl]-2'-(methanesulphonyl)-4-methylvalerohydrazide In a manner analogous to that described in the first paragraph of Example 2, starting from 0.128 g of (E)-2(R)-

[1(S)-[(tetrahydro-2(RS)-pyranyloxy)carbamoyl]-4-phenyl-3-butenyl]-2'-[2-(3-indolyl)ethyl]-2'-(methanesulphonyl)-4-methylvalerohydrazide there was obtained 0.063 g of (E)-2(R)[1(S)-(hydroxycarbamoyl)-4-phenyl-3-butenyl]-2'-[2-(3-indolyl)ethyl-2'-methanesulphonyl-4-methylvalerohydrazide in the form of a pale orange foam.
MS: 541 (M+H)+.

HPLC: Gradient elution using solvent A containing 5% solvent B increasing to 95% solvent B over 15 minutes; flow rate 1 ml/minute. Retention time: 12.52 minutes. Solvent A: H₂O/0.1% TFA; solvent B: CH₃CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 3-(2-bromoethyl)indole.

EXAMPLE 89

(E)-2(R)-[1(S)-(Hydroxycarbamoyl)-4-phenyl-3-butenyl]-2'-(methanesulphonyl)-4-methyl-2'-(3-phenylallyl)valerohydrazide In a manner analogous to that described in the first paragraph of Example 2, starting from 0.18 g of (E)-2(R)-[1(S)-[(tetrahydro-2(RS)-pyranyloxy)carbamoyl]-4-phenyl-3-butenyl]-2'-(methanesulphonyl)-4-methyl-2'-(3-phenylallyl)valerohydrazide there was obtained 0.123 g of (E)-2(R)-[1(S)-(hydroxycarbamoyl)-4-phenyl-3-butenyl]-2'-(methanesulphonyl)-4-methyl-2'-(3-phenylallyl)valerohydrazide in the form of a pale yellow solid.
MS: 514 (M+H)+.

HPLC: Gradient elution using solvent A containing 5% solvent B increasing to 95% solvent B over 15 minutes; flow rate 1 ml/minute. Retention time 12.69 minutes. Solvent A: H₂O/0.1% TFA; solvent B: CH₃CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methansulphonyl)-4-methylvalerohydrazide and cinnamyl bromide.

EXAMPLE 90

(E)-2'-Benzal-2'-(ethanesulphonyl)-2(R)-[1(S)-(hydroxycarbamoyl)-4-phenyl-3-butenyl]-4-methylvalerohydrazide In a manner analogous to that described in the first paragraph of Example 2, starting from 0.1 g of (E)-2'-benzyl-2'-(ethanesulphonyl)-2(R)-[1(S)-[(tetrahydro-2(RS)-pyranyloxy)carbamoyl]-4-phenyl-3-butenyl]-4-methylvalerohydrazide there was obtained 0.054 g of (E)-2'-benzyl-2'-(ethane sulphonyl)-2(R)-[1(S)-(hydroxycarbamoyl)-4-phenyl-3-butenyl]-4-methylvalerohydrazide in the form of an off-white solid.
MS: 502 (M+H)+.

HPLC: Gradient elution using solvent A containing 5% solvent B increasing to 95% solvent B over 15 minutes; flow rate 1 ml/minute. Retention time: 12.70 minutes. Solvent A: H₂O/0.1% TFA; solvent B: CH₃CN/0.085% TFA. Column type: HYPERPEP 300A.

The starting material was prepared in an analogous manner to that described in Example 85, parts (i)–(iii), starting from (E)-2(R)-[1(S)-tert-butoxycarbonyl)-4-phenyl-3-butenyl]-4-methylvalerohydrazide and ethanesulphonyl chloride.

EXAMPLE 91

(E)-2'-(2,2,2-Trifluoroethanesulphonyl)-2(R)-[1(S)-(hydroxycarbamoyl)-4-phenyl-3-butenyl]-4-methyl-2'-phenyl-valerohydrazide In a manner analogous to that described in the first pargraph of Example 2, starting from 0.125 g of (E)-2'-(2,2,2-trifluoroethanesulphonyl)-2(R)-[1(S)-[(tetrahydro-2(RS)-pyranyloxy)carbamoyl]-4-phenyl-3-butenyl]-4-methyl-2'-phenyl-valerohydrazide there was obtained 0.093 g of (E)-2'-(2,2,2-trifluoroethanesulphonyl)-2(R)-[1(S)-(hydroxycarbamoyl)-4-phenyl-3-butenyl]-4-methyl-2'-phenylvalerohydrazide in the form of an off-white solid.
MS: 542 (M+H)+.

HPLC: Gradient elution using solvent A containing 5% solvent B increasing to 95% solvent B over 15 minutes; flow rate 1 ml/minute. Retention time: 13.42 minutes. Solvent A: H₂O/0.1% TFA; solvent B CH₃CN/0.085% TFA. Column type: HYPERPEP 300A.

The starting material was prepared in an analogous manner to that described in Example 17, parts (i)–(iii), starting from (E)-2(R)-[1(S)-(tert-butoxycarbonyl)-4-phenyl-3-butenyl]-4-methylvalerohydrazide and 2,2,2-trifluoroethanesulphonyl chloride.

EXAMPLE 92

(E)-2(R)-[1(S)-(Hydroxycarbamoyl)-4-phenyl-3-butenyl]-2'-(3-hydroxypropyl)-2'-(methanesulphonyl)-4-methylvalrohydrazide In a manner analogous to that described in the first paragraph of Example 2, starting from 0.191 g of (E)-2(R)-[1(S)-[(tetrahydro-2(RS)-pyranyloxy)carbamoyl]-4-phenyl-3-butenyl]-2'-(3-hydroxypropyl)-2'-(methanesulphonyl)-4-methylvalrohydrazide there was obtained 0.119 g of (E)-2(R)-2(R)-[1(S)-(hydroxycarbamoyl)-4-phenyl-3-butenyl]-2'-(3-hydroxypropyl)-2'-(methanesulphonyl)-4-methylvalrohydrazide in the form of an off-white solid.
MS: 456 (M+H)+.

HPLC: Gradient elution using solvent A containing 5% solvent B increasing to 95% solvent B over 15 minutes; flow rate 1 ml/minute. Retention time: 9.61 minutes. Solvent A: H₂O/0.1% TFA; solvent B: CH₃CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalrohydrazide and 3-bromo-1-propanol.

EXAMPLE 93

(E)-2(R)-[1(S)-(Hydroxycarbamoyl)-4-phenyl-3-butenyl]-2'-(methanesulphonyl)-4-methyl-2'-[2-(3,4,4-trimethyl-2,5-dioxo-1-imidazolidinyl)ethyl]valerohydrazide In a manner analogous to that described in the first paragraph of Example 2, starting from 0.196 g of (E)-2(R)-[1(S)-[(tetrahydro-2(RS)-pyranyloxy)carbamoyl]-4-phenyl-3-butenyl]-2'-(methanesulphonyl)-4-methyl-2'-[2-(3,4,4-trimethyl-2,5-dioxo-1-imidazolidinyl)ethyl]valerohydrazide there was obtained 0.094 g of (E)-2(R)-[1(S)-(hydroxycarbamoyl)-4-phenyl-3-butenyl]-2'-

(methanesulphonyl)-4-methyl-2'-[2-(3,4,4-trimethyl-2,5-dioxo-1-imidazolidinyl)ethyl]valerohydrazide in the form of an off-white solid.

MS: 566 (M+H)$^+$.

HPLC: Gradient elution using solvent A containing 5% solvent B increasing to 95% solvent B over 15 minutes; flow rate 1 ml/minute. Retention time: 11.37 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylhydrazide and 3-(2-bromoethyl)-1,5,5-trimethylhydantoin.

EXAMPLE 94

(E)-2(R)-[1(S)-(Hydroxycarbamoyl)-4-phenyl-3-butenyl]-2'-(methanesulphonyl)-4-methyl-2'-(4-pentenyl)valerohydrazide In a manner analogous to that described in the first paragraph of Example 2, starting from 0.168 g of (E)-2(R)-[1(S)-[(tetrahydro-2(RS)-pyranyloxy)carbamoyl]-4-phenyl-3-butenyl]-2'-(methanesulphonyl)-4-methyl-2'-(4-pentenyl)valerohydrazide there was obtained 0.105 g of (E)-2(R)[1(S)-(hydroxyarbamoyl)-4-phenyl-3-butenyl]-2'-(methanesulphonyl)-4-methyl-2'-(4-pentenyl)valerohydrazide in the form of a white solid.

MS: 466 (M+H)$^+$.

HPLC: Gradient elution using solvent A containing 5% solvent B increasing to 95% solvent B over 15 minutes; flow rate 1 ml/minute. Retention time: 12.31 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 5-bromo-1-pentene.

EXAMPLE 95

(E)-2'-(3-Butenyl)-2(R)-[1(S)-(hydroxycarbamoyl)-4-phenyl-3-butenyl]-2'-(methanesulphonyl)-4-valerohydrazide In a manner analogous to that described in the first paragraph of Example 2, starting from 0.137 g of (E)-2'-(3-butenyl)-2(R)-[1(S)-[(tetrahydro-2(RS)-pyranyloxy)carbamoyl]-4-phenyl-3-butenyl]-2'-(methanesulphonyl)-4-valerohydrazide there was obtained 0.081 g of (E)-2'-(3-butenyl)-2(R)-[1(S)-(hydroxycarbamoyl)-4-phenyl-3-butenyl]-2'-(methanesulphonyl)-4-valerohydrazide in the form of a white solid.

MS: 452 (M+H)$^+$.

HPLC: Gradient elution using solvent A containing 5% solvent B increasing to 95% solvent B over 15 minutes; flow rate 1 ml/minute. Retention time: 11.80 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 4-bromo-1-butene.

EXAMPLE 96

(E)-2(R)-[1(S)-(Hydroxycarbamoyl)-4-phenyl-3-butenyl]-2'-(methanesulphonyl)-4-methyl-2'-propylvalerohydrazide In a manner analogous to that described in the first paragraph of Example 2, starting from 0.211 g of (E)-2((R)-[1(S)-[(tetrahydro-2(RS)-pyranyloxy)carbamoyl]-4-phenyl-3-butenyl]-2'-(methanesulphonyl)-4-methyl-2'-propylvalerohydrazide there was obtained 0.129 g of (E)-2(R)-[1(S)-(hydroxycarbamoyl)-4-phenyl-3-butenyl]-2'-(methanesulphonyl)-4-methyl-2'-propylvalerohydrazide in the form of a white solid.

MS: 440 (M+H)$^+$.

HPLC: Gradient elution using solvent A containing 5% solvent B increasing to 95% solvent B over 15 minutes; flow rate 1 ml/minute. Retention time: 9.77 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 1-bromopropane.

EXAMPLE 97

(E)-2'-Butyl-2(R)-[1(S)-hydroxycarbamoyl)-4-phenyl-3-butenyl]-2'-(methanesulphonyl)-4-methylvalerohydrazide In a manner analogous to that described in the first paragraph of Example 2, starting from 0.181 g of (E)-2'-butyl-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.129 g of (E)-2'-butyl-2(R)-1(S)-(hydroxycarbamoyl)-4-phenyl-3-butenyl]-2'-(methanesulphonyl)-4-methylvalerohydrazide in the form of a white solid.

MS: 454 (M+H)$^+$.

HPLC: Gradient elution using solvent A containing 5% solvent B increasing to 95% solvent B over 15 minutes; flow rate 1 ml/minute. Retention time: 12:12 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 1-bromobutane.

EXAMPLE 98

(E)-2'-(2-Aminoethyl)-2(R)-[1(S)-(hydroxycarbamoyl)-4-phenyl-3-butenyl]-2'-(methanesulphonyl)-4-methylvalerohydrazide p-toluenesulphonate.

In a analogous manner to that described in the first paragraph of Example 2, starting from 0.1 g of (E)-2'-(2-aminoethyl)-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.086 g of (E)-2'-(2aminoethyl)-2(R)-[1(S)-(hydroxycarbamoyl)-4-phenyl-3-butenyl]-2'-(methanesulphonyl)-4-methylvalerohydrazide p-toluenesulphonate in the form of an off-white solid.

MS: 441 (M+H)$^+$.

HPLC: Gradient elution using solvent A containing 5% solvent B increasing to 95% solvent B over 15 minutes; flow rate 1 ml/minute. Retention time: 9.58 minutes. Solvent A: H$_2$O/0.1% TFA; solvent B: CH$_3$CN/0.085% TFA. Column type: HYPERPEP 300A.

The starting material was prepared as follows:

A suspension of 0.926 g of (E)-2(R)-[1(S)-[(tetrahydro-2(RS)-pyranyloxy)carbamoyl]-4-phenyl-3-butenyl]-2'-(methanesulphonyl)-4-methyl-2'-(2-phthalimidoethyl)

valerohydrazide in 10 ml of methanol was treated with 0.25 ml of hydrazine hydrate. The mixture was stirred at room temperature overnight. The suspended white solid was filtered off, the filtrate was concentrated and the residue was purified by chromatography on silica gel using 5% methanol in dichloromethane for the elution. There was obtained 0.23 g of (E)-2'-(2-aminoethyl)-2(R)-[1(S)-[(tetrahydro-2(RS)-pyranyloxy)carbamoyl]-4-phenyl-3-butenyl]-2'-(methanesulphonyl)-4-methylvalerohydrazide in the form of a white solid after trituration of the product with ether.
MS: 525 (M+H)$^+$.

EXAMPLE 99

(E)-2(R)-[1(S)-(Hydroxycarbamoyl)-4-phenyl-3-butenyl]-2'-(methanesulphonyl)-4-methyl-2'-[2-(1-pyrroly)ethyl]valerohydrazide In a manner analogous to that described in the first paragraph of Example 2, starting from 0.163 g of (E)-2(R)-[1(S)-[(tetrahydro-2(RS)-pyranyloxy)carbamoyl]-4-phenyl-3-butenyl]-2'-(methanesulphonyl)-4-methyl-2'-[2-(1-pyrrolyl)ethyl]valerohydrazide there was obtained 0.041 g of (E)-2(R)-[1(S)-(hydroxyarbamoyl)-4-phenyl-3-butenyl]-2'-(methanesulphonyl)-4-methyl-2'-[2-(1-pyrroly)ethyl] valerohydrazide in the form of an off-white solid.
MS: 491 (M+H)$^+$.

HPLC: Gradient elution using solvent A containing 5% solvent B increasing to 95% solvent B over 15 minutes; flow rate 1 ml/minute. Retention time: 12.05 minutes. Solvent A: H$_2$O/0.1% TFA; Solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 1-(2-bromomethyl)-pyrrole.

EXAMPLE 100

(E)-2'-[2-(1,3-Dioxolan-2-yl)ethyl]-2(R)-[1(S)-(hydroxycarbamoyl)-4-phenyl-3-butenyl]-2'-(methanesulphonyl)-4-methylvalerohydrazide In a manner analogous to that described in the first paragraph of Example 2, starting from 0.145 g of (E)-2'-[2-(1,3-dioxolan-2-yl)ethyl]-2(R)-[1(S)-[(tetrahydro-2(RS)-pyranyloxy)carbamoyl]-4-phenyl-3-butenyl]-2'-(methanesulphonyl)-4-methylvalerohydrazide there was obtained 0.067 g of (E)- 2'-[2-(1,3-dioxolan-2-yl)ethyl]-2(R)-[1(S)-(hydroxycarbamoyl)-4-phenyl-3-butenyl]-2'-(methanesulphonyl)-4-methylvalerohydrazide in the form of a pale orange solid.
MS: 498 (M+H)$^+$.

HPLC: Gradient elution using solvent A containing 5% solvent B increasing to 95% solvent B over 15 minutes; flow rate ml/minute. Retention time: 10.63 minutes. Solvent A: H$_2$O/0.1% TFA; solvent B: CH$_3$CN/0.085% TFA. Column type: HYPERSIL ODS.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 2-(2-bromoethyl)-1,3-dioxolane.

EXAMPLE 101

(E)-2(R)-[1(S)-(Hydroxycarbamoyl)-4-phenyl-3-butenyl]-2'-(4-methoxybenzenesulphonyl)-4-methylvalerohydrazide In a manner analogous to that described in the first paragraph of Example 2, starting from 0.19 g of (E)-2(R)-[1(S)-[(tetrahydro-2(RS)-pyranyloxy)carbamoyl]-4-phenyl-3-butenyl]-2'-(4-methoxybenzenesulphonyl)-4-methylvalerohydrazide there was obtained 0.115 g of (E)-2(R)-[1(S)-(hydroxycarbamoyl)-4-phenyl-3-butenyl-2'-(4-methoxybenzenesulphonyl)-4-methylvalerohydrazide in the form of a white solid.
MS: 490 (M+H)$^+$.

HPLC: Gradient elution using solvent A containing 5% solvent B increasing to 95% solvent B over 15 minutes; flow rate 1 ml/minute. Retention time: 11.53 minutes. Solvent A: H$_2$O/0.1% TFA; solvent B: CH$_3$CN/0.085% TFA. Column type: HYPERPEP 300A.

The starting material was prepared as follows:

(i) In a manner analogous to that described in Example 1, part (ii), from 0.54 g of (E)-2(R)-1(S)-(tert-butoxycarbonyl)-4-phenyl-3-butenyl]-4-methylvalerohydrazide and 4-methoxybenzenesulphonyl chloride there was obtained 0.492 g of (E)-2(R)-[1(S)-(tert-butoxycarbonyl)-4-phenyl-3-butenyl]-2'-(4-methoxybenzenesulphonyl)-4-methylvalerohydrazide in the form of a white solid.
MS: 531 (M+H)$^+$.

(ii) In a manner analogous to that described in Example 1, part (iii), followed by that described in Example 2, part (v), from 0.482 g of (E)-2(R)-[1(S)-(tert-butoxycarbonyl)-4-phenyl-3-butenyl]-2'-(4-methoxybenzenesulphonyl)-4-methylvalerohydrazide there was obtained 0.194 g of (E)-2(R)-[1(S)-[(tetrahydro-2(RS)-pyranyloxy)carbamoyl]-4-phenyl-3-butenyl]-2'-(4-methoxybenzenesulphonyl)-4-methylvalerohydrazide in the form of a white solid.
MS: 574 (M+H)$^+$.

EXAMPLE 102

(E,E)-2(R)-[1(S)-(Hydroxycarbamoyl)-4-phenyl-3-butenyl]-4-methyl-2'-phenyl-2'-[(2-phenylvinylsulphonyl]valerohydrazide In a manner analogous to that described in the first paragraph of Example 2, starting from 0.245 g of (E,E)-2(R)-[1(S)-[(tetrahydro-2(RS)-pyranyloxy)carbamoyl]-4-phenyl-3-butenyl]-4-methyl-2'-phenyl-2'-[(2-phenylvinylsulphonyl]valerohydrazide there was obtained 0.086 g of (E,E)-2(R)-[1(S)-(hydroxycarbamoyl)-4-phenyl-3-butenyl]-4-methyl-2'-phenyl-2'-[(2-phenylvinylsulphonyl]valerohydrazide in the form of a white solid.
MS: 562 (M+H)$^+$.

HPLC: Gradient elution using solvent A containing 5% solvent B increasing to 95% solvent B over 15 minutes; flow rate 1 ml/minute. Retention time: 13.94 minutes. Solvent A: H$_2$O/0.1% TFA; solvent B: CH$_3$CN/0.085% TFA. Column type: HYPERPEP 300A.

The starting material was prepared in an analogous manner to that described in Example 1, parts (ii) and (iii), followed by that described in Example 2, part (v), from (E)-2(R)-[1(S)-(tertbutoxycarbonyl)-4-phenyl-3-butenyl]-4-methyl-2'-phenylhydrazide and trans-beta-styrenesulphonyl chloride.

EXAMPLE 103

(E)-2'-Furfural-2(R)-[1(S)-(hydroxycarbonyl)-4-phenyl-3-butenyl]-2'-(methanesulphonyl)-4-methylvalerohydrazide In a manner analogous to that described in the first paragraph of Example 2, starting from 0.071 g of (E)-2'- furfural-2(R)-[1(S)-[(tetrahydro-2(RS)-pyranyloxy) carbamoyl]-4-phenyl-3-butenyl]-2'-(methanesulphonyl)-4-methylvalerohydrazide there was obtained 0.042 g of (E)-2'-furfural-2(R)[1(S)-(hydroxycarbamoyl)-4-phenyl-3-butenyl]-2'-(methanesulphonyl)-4-methylvalerohydrazide in the form of a white solid.

MS: 478 (M+H)$^+$.

HPLC: Isocratic elution using 50% $CH_3CN$/water; flow rate 1 ml/minute. Retention time: 3.82 minutes. Column type: Waters symmetry 10 cm, $C_{18}$, 0.46 cm i.d.

The starting material was prepared in an analogous manner to that described in Example 45, parts (i) and (ii), starting from (E)-2(R)-[1(S)-(tert-butoxycarbonyl)-4-phenyl-3-butenyl]-4-methylvalerohydrazide and 2-furaldehyde.

EXAMPLE 104

(E)-2'-Ethyl-2(R)-[1(S)-(hydroxycarbamoyl)-4-phenyl-3-butenyl]-2'-(methanesulphonyl)-4-methylvalerohydrazide In a manner analogous to that described in the first paragraph of Example 2, starting from 0.136 g of (E)-2'-ethyl-2(R)-[1(S)-tetrahydro-2(RS)-pyranyloxy)carbamoyl]-4-phenyl-3-butenyl]-2'-(methanesulphonyl)-4-methylvalerohydrazide there was obtained 0.087 g of (E)-2'-ethyl-2(R)-[1(S)-(hydroxycarbamoyl)-4-phenyl-3-butenyl]-2'-(methanesulphonyl)-4-methylvalerohydrazide in the form of a white solid.

MS: 426 (M+H)$^+$.

HPLC: Gradient elution using solvent A containing 20% solvent B increasing to 80% solvent B over 15 minutes; flow rate 1 ml/minute. Retention time: 14.12 minutes. Solvent A: 100% 0.05M triethylammonium phosphate buffer, ph 2.5 (TEAP); solvent B: 80% $CH_3CN$/(TEAP). Column type: Waters symmetry 10 cm, 0.46 cm i.d.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl-2'-(methanesulphonyl)-4-methylvalerohydrazide and ethyl iodide.

EXAMPLE 105

(E)-2'-(2,6-Dichlorobenzyl)-2(R)-[1(S)-(hydroxycarbamoyl)-4-phenyl-3-butenyl]-2'-(methanesulphonyl)-4-methylvalerohydrazide In a manner analogous to that described in the first paragraph of Example 2, starting from 0.09 g of (E)-2'-(2,6-dichlorobenzyl)-2(R)-[1(S)-[1(tetrahydro-2(RS)-pyranyloxycarbamoyl]-4-phenyl-3-butenyl]-2'-(methanesulphonyl)-4-methylvalerohydrazide there was obtained 0.05 g of (E)-2'-(2,6-dichlorobenzyl)-2(R)-[(S)-(hydroxycarbamoyl)-4-phenyl-3-butenyl]-2'-(methanesulphonyl)-4-methylvalerohydrazide in the form of a white solid.

MS: 556/558 (M+H)$^+$.

HPLC: Gradient elution using solvent A containing 30% solvent B increasing to 95% solvent B over 7 minutes; flow rate: 1 ml/minute. Retention time: 7.30 minutes. Solvent A: $H_2O$/0.1% TFA; solvent B $CH_3CN$/0.1% TFA. Column type: HYPERSIL ODS.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 2,6-dichlorobenzyl bromide.

EXAMPLE 106

(E)-2'-(Cyclopentylmethyl)-2(R)-[1(S)-(hydroxycarbamoyl)-4-phenyl-3-butenyl]-2'-(methanesulphonyl)-4-methylvalerohydrazide In a manner analogous to that described in the first paragraph of Example 2, starting from 0.04 g of (E)-2'-(cyclopentylmethyl)-2(R)-[1(S)-[(tetrahydro-2(RS)-pyranyloxycarbamoyl]-4-phenyl-3-butenyl]-2'-(methanesulphonyl)-4-methylvalerohydrazide there was obtained 0.041 g of (E)-2'-cyclopentylmethyl)-2(R)-[1(S)-(hydroxycarbamoyl)-4-phenyl-3-butenyl]-2'-(methanesulphonyl)-4-methylvalerohydrazide in the form of a white solid.

MS: 480 (M+H)$^+$.

HPLC: Isocratic elution using 60% $CH_3CN$/TEAP; flow rate 1 ml/minute. Retention time: 3.25 minutes. Column type: Waters symmetry 10 cm, $C_{18}$, 0.46 cm i.d.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and cyclopentylmethyl methanesulphonate.

EXAMPLE 107

2(R)-[2-(2-Benzofuranyl)-1(S)-(hydroxycarbamoyl) ethyl-2'-isobutyl-2'-(methanesulphonyl)-4-methylhydrazide In a manner analogous to that described in the first paragraph of Example 2, starting from 0.066 g of 2(R)-[2-(2-benzofuranyl)-1(S)-[(tetrahydro-2(RS)-pyranyloxy) carbamoyl]ethyl]-2'-isobutyl-2'-(methanesulphonyl)-4-methylhydrazide there was obtained 0.015 g of 2(R)-[2-(2-benzofuranyl)-1(S)-(hydroxycarbamoyl)ethyl]-2'-isobutyl-2'-(methanesulphonyl)-4-methylhydrazide in the form of a white solid.

MS: 468 (M+H)$^+$.

HPLC: Gradient elution using solvent A containing 5% solvent B increasing to 98% solvent B over 15 minutes; flow rate 1 ml/minute. Retention time: 12.34 minutes. Solvent A: $H_2O$/0.1% TFA: solvent B: $CH_3 CN$/0.085% TFA. Column type: HYPERPEP 300A.

The starting material was prepared as follows:

(i) 1.14 g of 60% sodium hydride were added to a stirred solution of 12.35 g of 1,2-dibenzyl 1tert-butyl 4-methyl-1,1,2(R)-pentanetricarboxylate in 150 ml of dry, ice-cold dimethylformamide under a nitrogen atmosphere. The mixture was stirred at ice temperature for 30 minutes and at room temperature for a further 1.5 hours. The mixture was again cooled to ice temperature before the addition of 5.78 g of 2-bromomethylbenzoftran. The mixture was allowed to return to room temperature slowly and was stirred overnight. The solution was then evaporated and the residue was partitioned between ethyl acetate and 5% citric acid solution. The ethyl acetate solution was washed with water and saturated sodium chloride solution and dried over anhydrous magnesium sulphate. The solvent was evaporated and the residue was purified by flash chromatography on silica gel using hexane/ether (9:1) for the elution. There were obtained 14.64 g of 1,2-dibenzyl 1-tert-butyl-1-(2-benzofuranyl) methyl-4-methyl-4-methyl-1,1,2(R)-pentanetricarboxylate in the form of a colourless oil.

(ii) 14.64 g of 1,2-dibenzyl-1-tert-butyl-1-(2-benzofuranyl)methyl-4-methyl-1,1,2(R)-pentanetricarboxylate were distilled in 150 ml of ethanol and a solution of 9.8 g of sodium hydroxide in 55 ml of water was added. The mixture was heated under reflux for 24 hours, cooled and the solvents were evaporated. The residue was dissolved in 400 ml of water and the pH was adjusted to 3 by the addition of 4M sulphuric acid solution. The aqueous solution was extracted with 400 ml of ethyl acetate and the extract was washed in succession with water and saturated sodium chloride solution and dried over anhydrous magnesium sulphate. The solvent was evaporated and the residue was dissolved in 150 ml of toluene containing 3.8 ml of triethylamine. The mixture was heated under reflux for 2 hours, cooled and washed in succession with 5% citric solution, water and saturated sodium chloride solution. After drying over anhydrous magnesium sulphate the solvent was evaporated and the residue was dissolved in 50 ml of hexane and treated with 2.43 g of cyclohexane. The mixture was kept in a refrigerator for 2 hours and the white solid formed was filtered off and washed with hexane. The solid was suspended in 150 ml of ethyl acetate and shaken with two 50 ml portions of 2M sulphuric acid. The ethyl acetate solution was washed in succession with water and saturated sodium chloride solution, dried over anhydrous magnesium sulphate and evaporated. There were obtained 3.701 g of 4-tert-butyl hydrogen 3(S)-(2-benzofuranyl)methyl-2(R)-isobutylsuccinate in the form of a pale yellow gum.

(iii) In an analogous manner to that described in Example 15, parts (i)–(iii), starting from 4-tertbutyl hydrogen 3(S)-(2-benzofuranyl)methyl-2(R)-isobutylsuccinate and using 1-bromo-2-methanepropane in part (iii) there was obtained 2(R)-[2-(2-benzofuranyl)-1(S)-[(tetrahydro-2(RS)-pyranyloxy)carbamoyl]ethyl]-2'-isobutyl-2'-(methanesulphonyl)-4-methylhydrazide in the form of a white solid.

MS: 552 (M+H)$^+$.

EXAMPLE 108

(E)-2(R)-[1(S)-(Hydroxycarbamoyl)-4-phenyl-3-butenyl]-2'-(methanesulphonyl)-4-methyl-2'-[(3-pyridyl)methyl]valerohydrazide methanesulphate In a manner analogous to that described in the first paragraph of Example 2, but using methanesulphonic acid in place of p-toluenesulphonic acid, starting from 0.2 g of (E)-2(R)-[1(S)-[(tetrahydro-2(RS)-pyranyloxy)carbamoyl]-4-phenyl-3-butenyl]-2'-(methanesulphonyl)-4-methyl-2'-[(3-pyridyl)methyl]valerohydrazide there was obtained 0.177 g of (E)-2(R)-[1(S)-(hydroxycarbamoyl)-4-phenyl-3-butenyl]-2'-(methanesulphonyl)-4-methyl-2'-[(3-pyridyl)methyl]valerohydrazide methanesulphonate in the form of an orange solid.

MS: 489 (M+H)$^+$.

HPLC: Gradient elution using solvent A containing 5% solvent B increasing to 95% solvent B over 15 minutes; flow rate 1 ml/minute. Retention time: 8.05 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 3-bromomethylpyridine hydrobromide.

EXAMPLE 109

(E)-2(R)-[1(S)-(Hydroxycarbamoyl)-4-phenyl-3-butenyl]-2'-(methanesulphonyl)-4-methyl-2'-[2-(2-pyridyl)ethyl]valerohydrazide methanesulphonate In a manner analogous to that described in the first paragraph of Example 2, but using methanesulphonic acid in place of p-toluenesulphonic acid, starting from 0.176 g of (E)-2(R)-[1(S)-[tetrahydro-2(RS) pyridyl)ethyl] valerohydrazide there was obtained 0.13 g of (E)-2(R)-[1(S)-(hydroxycarbamoyl)-4-phenyl-3-butenyl]-2'-(methanesulphonyl)-4-methyl-2'-[2-(2-pyridyl)ethyl] valerohydrazide methanesulphonate in the form of a pale orange solid.

MS: 503 (M+H)$^+$.

HPLC: Gradient elution using solvent A containing 5% solvent B increasing to 95% solvent B over 15 minutes; flow rate 1 ml/minute. Retention time: 9.97 minutes. Solvent A: H$_2$O/0.1% TFA; solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(R)-pyranyloxy)carbamoyl]-4-phenyl-3-butenyl]-2'-(methanesulphonyl)-4-methylvalerohydrazide and 2-(2-bromoethyl)pyridine hydrobromide.

EXAMPLE 110

E-2(R)-[1(S)-(Hydroxycarbamoyl-4-phenyl-3-butenyl]-2'-(methanesulphonyl)-4-methyl-2'-[2-(2-pyridyl)ethyl]valerohydrazide methanesulphonate In a manner analogous to that described in the first paragraph of Example 2, but using methanesulphonic acid in place of p-toluenesulphonic acid, starting from 0.146 of (E)-2(R)-[1(S)-[(tetrahydro-2(RS)-pyranyloxy)carbamoyl]-4-phenyl-3-butenyl]-2'-(methanesulphonyl)-4-methyl-2'-[2-(2-(4-pyridyl)ethyl] valerohydrazide there was obtained 0.104 g of (E)-2(R)-[1(S)-(hydroxycarbamoyl)-4-phenyl-3-butenyl]-2'-(methanesulphonyl)-4-methyl-2'-[2-(2-pyridyl)ethyl]valerohydrazide methanesulphonate in the form of a pale orange solid.

MS: 503 (M+H)$^+$.

HPLC: Gradient elution using solvent A containing 5% solvent B increasing to 95% solvent B over 15 minutes; flow rate 1 ml/minute. Retention time: 9.74 minutes. Solvent A: H$_2$O/0.1% TFA; Solvent B: CH$_3$CN/0.085% TFA. Column type: HYPERPEP 300A.

The starting material was prepared in an analogous manner to that described in Example 15, part (iii), starting from (E)-2(R)-[1(S)-[(tetrahydro-2(RS)-pyranyloxy)carbamoyl]-4-phenyl-3-butenyl]-2'-(methanesulphonyl)-4-methylvalerohydrazide and 4-(2-bromoethyl)pyridine hydrobromide.

EXAMPLE 111

2(R)-[3-Cyclohexylidene-1(S)-(hydroxycarbamoyl)-propyl]-2'-isobutyl-2'-(methanesulphonyl)-4-methylvalerohydrazide In a manner analogous to that described in the first paragraph of Example 2 from 0.085 g of 2(R)-[3-cyclohexylidene-1(S)-[(tetrahydro-2(RS)-pyranyloxy)carbamoyl]propyl]-2'-isobutyl-2'-(methanesulphonyl)-4-methylvalerohydrazide there was obtained 0.042 g of 2(R)-[3-cyclohexylidene-1(S)-(hydroxycarbamoyl)propyl]-2'-isobutyl-2'-(methanesulphonyl)-4-methylvalerohydrazide in the form of a white solid.

MS: 446 (M+H)$^+$.

HPLC: Gradient elution using solvent A containing 5% solvent B increasing to 95% solvent B over 15 minutes; flow rate 1 ml/minute. Retention time: 12.20 minutes. Solvent A: H$_2$O/0.1% TFA; solvent B: CH$_3$CN/0.085% TFA. Column type: HYPERPEP 300A The starting material was prepared as follows:

(i) In a manner analogous to that described in Example 107 parts (i) and (ii), except that the product was purified by flash chromatography on silica gel using hexane/ether (4:1) for the elution instead of by crystallization of the cyclohexylamine salt, starting from 1,2-dibenzyl 1-tert-butyl 4-methyl-1,1,2(R)-pentanetricarboxylate and (2-bromoethylidene) cyclohexane there was obtained 4-tert-butyl hydrogen 3(S)-[(2-cyclohexylidene)ethyl]-2(R)-isobutylsuccinate in the form of a pale yellow gum.

MS: 339 (M+H)$^+$.

(ii) In a manner analogous to that described in Example 2, parts (iii)–(v), starting from 4-tert-butyl hydrogen 3(S)-[(2-cyclohexylidene)ethyl]-2(R)-isobutylsuccinate and isobutylhydrazine and using trimethylsilyl trifluoromethanesulphonate in 1,4-dioxane instead of trifluoroacetic acid to deprotect the tertiary butyl ester there was obtained 2(R)-[3-cyclohexylidene-1(S)-[(tetrahydro-2(RS)-pyranyloxy)carbamoyl]propyl]-2'-isobutyl-2'-(methanesulphonyl)-4-methylvalerohydrazide in the form of a yellow solid.

MS: 530 (M+H)$^+$.

EXAMPLE 112

2(R)-[3-(Tetrahydro-2H-pyran-4-ylidene)-1(S)-(hydroxycarbamoyl)propyl]-2'-isobutyl-2'-(methanesulphonyl)-4-methylvalerohydrazide In a manner analogous to that described in the first paragraph of Example 2, starting from 0.09 g of 2(R)-[3-(tetrahydro-2H-pyran-4-ylidene)-1(S)-[(tetrahydro-2(RS)-pyranyloxy)carbamoyl]-propyl]-2'-isobutyl-2'-(methanesulphonyl)-4-methylvalerohydrazide there was obtained 0.046 g of 2(R)-[3-(tetrahydro-2H-pyran-4-ylidene)-1(S)-(hydroxycarbamoyl)propyl]-2'-isobutyl-2'-(methanesulphonyl)-4-methylvalerohydrazide in the form of a white solid.

MS: 448 (M+H)$^+$.

HPLC: Gradient elution using solvent A containing 5% solvent B increasing to 95% solvent B over 15 minutes; flow rate 1 ml/minute. Retention time: 10.22 minutes. Solvent A: H$_2$O/0.1% TFA; solvent B: CH$_3$CN/0.085% TFA. Column type: HYPERPEP 300A.

The starting material was prepared as follows:

(i) In a manner analogous to that described in Example 107, parts (i) and (ii), except that the product was purified by flash chromatography on silica gel using hexane/ether (4:1) for the elution instead of by crystallization of the cyclohexylatnine salt, starting from 1,2-dibenzyl 1-tert-butyl 4-methyl-1,1,2-2(R)-pentanetricarboxylate and 4-(2-bromoethylidene) tetrahydro-2H-pyran there was obtained 4-tert-butyl hydrogen 3(S)-[(tetrahydro-2H-pyran-4-ylidene) ethyl]-2(R)-isobutylsuccinate in the form of a pale yellow gum.

MS: 341 (M+H)$^+$.

(ii) In a manner analogous to that described in Example 2, parts (iii)–(v), starting from 4-tert-butyl hydrogen 3(S)-[(tetrahydro-2H-pyran-4-ylidene)ethyl]-2(R)-isobutylsuccinate and isobutylhydrazine and using trimethylsilyl trifluoromethanesulphonate in 1,4-dioxane instead of trifluoroacetic acid to deprotect the tertiary butyl ester there was obtained 2(R)-[3-(tetrahydro-2H-pyran-4-ylidene)-1(S)-[(tetrahydro-2(RS)-pyranyloxy) carbamoyl]-propyl]-2'-isobutyl-2'-methanesulphonyl)-4-methylvalerohydrazide in the form of an off-white solid.

MS: 532 (M+H)$^+$.

EXAMPLE 113

2(R)-[3-(Tetrahydro-2H-pyran-4-yl)-1(S)-(hydroxycarbamoyl)propyl]-2'-isobutyl-2'-(methanesulphonyl)-4-methylvalerohydrazide In a manner analogous to that described in the first paragraph of Example 2, starting from 0.14 g of 2(R)-[3-(tetrahydro-2H-pyran-4-yl)-1(S)-[(tetrahydro-2(RS)-(pyranyloxy)carbamoyl]propyl]-2'-isobutyl-2'-(methanesulphonyl)-4-methylvalerohydrazide there was obtained 0.083 g of 2(R)-[3(tetrahydro-2H-pyran-4-yl)-1(S)-(hydroxycarbamoyl)propyl]-2'-isobutyl-2'-methanesulphonyl)-4-methylvalerohydrazide in the form of an off-white solid.

MS: 450 (M+H)$^+$.

HPLC: Gradient elution using solvent A containing 5% solvent B increasing to 95% solvent B over 15 minutes; flow rate 1 ml/minute. Retention time: 10.15 minutes. Solvent A: H$_2$O/0.1% TFA; solvent B: CH$_3$CN/0.085% TFA. Column type: HYPERPEP 300A.

The starting material was prepared as follows:

(i) A solution of 0.397 g of 4-tert-butyl hydrogen 3(S)-[(tetrahydro-2H-pyran-4-ylidene)ethyl]-2(R)-isobutylsuccinate in 10 ml of methanol was shaken in a hydrogen atmosphere in the presence of 0.196 g of 10% palladium on charcoal catalyst until no further uptake of hydrogen was observed. The catalyst was filtered off and the filtrate was evaporated. There was obtained 0.331 g of 4-tert-butyl hydrogen 3(S)-[(tetrahydro-2H-pyran-4-yl)ethyl]-2(R)-isobutylsuccinate in the form of a colourless gum.

MS: 343 (M+H)$^+$.

(ii) In a manner analogous to that described in Example 2, parts (iii)–(v), starting from 4-tert-butyl hydrogen 3(R)-(tetrahydro-2H-pyran-4-yl)ethyl-2(R)-isobutylsuccinate and isobutylhydrazine there was obtained 2(R)-[3-(tetrahydro-2H-pyran-4-yl)-1(S)-[(tetrahydro-2(RS)-pyranyloxy)carbamoyl]propyl]-2'-isobutyl-2'-methanesulphonyl)-4-methylvalerohydrazide in the form of a white solid.

MS: 534 (M+H)$^+$.

EXAMPLE 114

2(R)-[3-Cyclohexyl-1(S)-(hydroxycarbamoyl) propyl]-2'-isobutyl-2'-(methanesulphonyl)-4-methylvalerohydrazide In a manner analogous to that described in the first paragraph of Example 2, starting from 0.145 g of 2(R)-[3-cyclohexyl-1(S)-[(tetrahydro-2(RS)-pyranyloxy) carbamoyl]propyl]-2'-isobutyl-2'-(methanesulphonyl)-4-methylvalerohydrazide there was obtained 0.093 g of 2(R)-[3-cyclohexyl-1(S)-(hydroxycarbamoyl)propyl]-2'-isobutyl-2'-(methanesulphonyl)-4-methylvalerohydrazide in the form of a white solid.

MS: 448 (M+H)$^+$.

HPLC: Gradient elution using solvent A containing 5% solvent B increasing to 95% solvent B over 15 minutes; flow rate 1 ml/minute. Retention time: 12.82 minutes. Solvent A: H$_2$O/0.1% TFA; solvent B: CH$_3$CN/0.085% TFA. Column type: HYPERPEP 300A.

The starting material was prepared in an analogous manner to that described in Example 113, parts (i) and (ii), starting from 4-tert-butyl hydrogen 3(S)-(2-cyclohexylidene)ethyl-2(R)-isobutylsuccinate.

EXAMPLE 115

2(R)-[1(S)-(Hydroxycarbamoyl)-4-phenyl-3-butynyl]-2'-isobutyl-2'-(methanesulphonyl)-4-methylvalerohydrazide In a manner analogous to that described in the first paragraph of Example 2, starting from 0.189 g of 2(R)-[1(S)-[(tetrahydro-2(RS)-pyranyloxy)carbamoyl]-4-phenyl-3-butynyl]-2'-isobutyl-3-butynyl]-2'-isobutyl-2'-(methanesulphonyl)-4-methylvalerohyrazide there was obtained 0.098 g of 2(R)-[1(S)-(hydroxycarbamoyl)-4-phenyl-3-butynyl]-2'-isobutyl-2'-(methanesulphonyl)-4-methylvalerohyrazide in the form of a white solid.

MS: 452 (M+H)$^+$.

HPLC: Gradient elution using solvent A containing 95% solvent B increasing to 95% solvent B over 15 minutes; flow rate 1 ml/minute. Retention time: 12.42 minutes. Solvent A: H$_2$O/0.1% TFA; solvent B: CH$_3$CN/0.085% TFA. Column type: HYPERPEP 300A.

The starting material was prepared as follows:

(i) In a manner analogous to that described in Example 107, parts (i) and (ii), starting from 1,2-dibenzyl 1-tert-butyl-4-methyl-1,1,2(R)-pentanetricarboxylate and 1-bromo-3-phenyl-2-propyne there was obtained 2(R)-[1(S)-tert-butoxycarbonyl)-4-phenyl-3-butynyl-4-methylvaleric acid in the form of a pale yellow solid.

(ii) In a manner to that described in Example 2, parts (iii)–(v), starting from 2(R)-[1(S)-(tertbutoxycarbonyl)-4-phenyl-3-butynyl)-4-methylvaleric acid and isobutylhydrazine there was obtained 2(R)-[1(S)-[(tetrahydro-2(RS)-pyranyloxy)carbamoyl-4-phenyl-3-butynyl-2'-isobutyl-2'-(methanesulphonyl)-4-methylvalerohyrazide in the form of a white solid.

MS: 536 (M+H)$^+$.

EXAMPLE 116

2(R)-[1(S)-(Hydroxycarbamoyl)-3-phenoxypropyl]-2'-isobutyl-2'-(methanesulphonyl)-4-methylvalerohydrazide In a manner analogous to that described in the first paragraph of Example 2, starting from 0.23 g of 2(R)-[1(S)-[(tetrahydro-2(RS)-pyranyloxy)carbamoyl]-3-phenoxypropyl]-2'-isobutyl-2'-(methanesulphonyl)-4-methylvalerohydrazide there was obtained 0.143 g of 2(R)-[1(S)-(hydroxycarbamoyl)-3-phenoxypropyl]-2'-isobutyl-2'-(methanesulphonyl)-4-methylvalerohydrazide in the form of a creamy-white solid.

MS: 458 (M+H)$^+$.

HPLC: Gradient elution using solvent A containing 5% Solvent B increasing to 95% solvent B over 15 minutes; flow rate 1 ml/minute. Retention time: 11.89 minutes. Solvent A: H$_2$O/0.1% TFA; solvent B: CH$_3$CN/0.085% TFA. Column type: HYPERPEP 300A.

The starting material was prepared as follows:

(i) In a manner analogous to that described in Example 107, parts (i) and (ii), except that the product was purified by flash chromatography on silica gel using hexane/ether (4:1) for the elution instead of by crystallization of the cyclohexylamine salt, starting from 1,2-dibenzyl 1-tert-butyl 4-methyl-1,1,2(R)-pentanetricarboxylate and (2-iodoethoxy)benzene there was obtained 4-tert-butyl hydrogen 3(S)-(2-phenoxy)ethyl-2(R)-isobutylsuccinate in the form of a pale yellow oil.

MS: 351(M+H)$^+$.

(ii) In a manner analogous to that described in Example 2, parts (iii)–(v), starting from 4-tert-butyl hydrogen 3(S)-(2-phenoxy)ethyl-2(R)-isobutyl succinate and isobutylhydrazine there was obtained 2(R)-[1(S)-[(tetrahydro-2(RS)-pyranyloxy)carbamoyl]-3-phenoxypropyl]-2'-isobutyl-2'-(methanesulphonyl)-4-methylvalerohydrazide in the form of a white solid.

MS: 542 (M+H)$^+$.

EXAMPLE 117

(E)-2(R)-[1(S)-(Hydroxycarbamoyl)-4-phenyl-3-butenyl]-2'-(methanesulphonyl)-4-methyl-2'-](3-methyl-3-oxetanyl)methyl]valerohydrazide In a manner analogous to that described in the first paragraph of Example 2, starting from 0.34 g of (E)-2(R)-[1(S)-[(tetrahydro-2(RS)-pyranyloxy)carbamoyl]-4-phenyl-3-butenyl]-2-(methanesulphonyl)-4-methyl-2'-[(3-methyl-3-oxetanyl)methyl]valerohydrazide there was obtained 0.22 g of (E)-2(R)-[(S)-(hydroxycarbamoyl)-4-phenyl-3-butenyl]-2'-(methanesulphonyl)-4-methyl-2'-[(3-methyl-3-oxetanyl)methyl]valerohydrazide in the form of a white solid.

MS: 482 (M+H)$^+$.

HPLC: Gradient elution using solvent A containing 5% solvent B increasing to 95% solvent B over 15 minutes; flow rate 1 ml/minute. Retention time: 10.76 minutes. Solvent A: H$_2$O/0.1% TFA: solvent B: CH$_3$CN/0.085% TFA. Column type: HYPERPEP 300A.

The starting material was prepared in an analogous manner to that described in Example 45, parts (i) and (ii), starting from (E)-2(R)-[1(S)-tert-butoxycarbonyl)-4-phenyl-3-butenyl]-4-methylvalerohydrazide and 3-methyl-3-oxetanecarboxaldehyde.

EXAMPLE 118

2(R)-[1(S)-Hydroxycarbamoyl)-3-butenyl]-2'-(methanesulphonyl)-4-methyl-2'-phenylvalerohydrazide In an analogous manner to that described in the first paragraph of Example 2, starting from 0.58 g of 2(R)-[1(S)-[(tetrahydro-2(RS)-pyranyloxy)carbamoyl]-3-butenyl]-2'-(methanesulphonyl)-4-methyl-2'-phenylvalerohydrazide there was obtained 0.41 g of 2(R)-[1(S)-(hydroxycarbamoyl)-3-butenyl]-2'-(methanesulphonyl)-4-methyl-2'-phenylvalerohydrazide in the form of a white solid.

MS: 398 (M+H)$^+$.

HPLC: Gradient elution using solvent A containing 5% solvent B increasing to 95% solvent B over 15 minutes; flow rate 1 ml/minute. Retention time: 9.97 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy)carbamoyl]-3-butenyl]-2'-(methanesulphonyl)-4-methyl-2'-phenylvalerohydrazide used as the starting material was prepared as follows:

In an analogous manner to that described in Example 1, part (i) and Example 2, parts (iii)–(v), starting from 2(R)-[1(S)-(tert-butoxycarbonyl)-3-butenyl-4-methylvaleric acid there was obtained 2(R)[1(S)-[(tetrahydro-2(RS)- pyranyloxy)carbamoyl]-3-butenyl]-2'-(methanesulphonyl)-4-methyl-2'-phenylvalerohydrazide in the form of a white solid.

MS: 482 (M+H)+.

EXAMPLE 119

2(R)-[1(S)-(Hydroxycarbamoyl)-butyl]-2'-(methanesulphonyl)-4-methyl-2'-phenylvalerohydrazide In an analogous manner to that described in the first paragraph of Example 65, starting from 0.50 g of 2(R)-[1(S)-[(benzyloxy)carbamoyl]-butyl]-2'-(methanesulphonyl)-4-methyl-2'-phenylvalerohydrazide there was obtained 0.36 g of 2(R)-[1(S)-(hydroxycarbamoyl)-butyl]-2'-(methanesulphonyl)-4-methyl-2'-phenylvalerohydrazide in the form of a white solid.

MS: 400 (M+H)+.

HPLC: Gradient elution using solution 5% solvent A increasing to 95% solvent B over 15 minutes; flow rate 1 ml/minute. Retention time: 10.14 minutes. Solvent A: H₂O/ 0.1% TFA; Solvent B: CH₃CN/0.085% TFA.

Column type: HYPERPEP 300A.

The 2(R)-[1(S)-[(benzyloxy)carbamoyl]-butyl]-2'-(methanesulphonyl)-4-methyl-2'-phenylvalerohydrazide used as the starting material was prepared as follow:

(i) A solution of 3.0 g of 2(R)-[1(S)-(tertbutoxycarbonyl)-3-butenyl]-4-methylvaleric acid in 30 ml of ethanol was hydrogenated in the presence of 0.3 g of 5% palladium-on-carbon for 4 hours. The catalyst was removed by filtration and the solvent was evaporated. The residue was dissolved in 30 ml of toluene and the solvent was evaporated again. Repetition of this procedure gave 2.83 g of 2(R)-[1(S)-(tertbutoxycarbonyl)-butyl]-4-methyl-valeric acid as a colourless oil.

(ii) In an analogous manner to that described in Example 1, part (i) and Example 65, parts (ii)–(iv), starting from 2(R)-[1(S)-(tertbutoxycarbonyl)-butyl]-4-methyl-valeric acid there was obtained 2(R)-[1(S)-[(benzyloxy)carbamoyl]-butyl]-2'-(methanesulphonyl)-4-methyl-2'-phenylvalerohydrazide in the form of a white solid.

MS: 490 (M+H)+.

EXAMPLE 120

(E)-2(R)-[1(S)-(Hydroxycarbamoyl)-4-phenyl-3-butenyl]-4-methyl-N-phthalimidovaleramide In an analogous manner to that described in the first paragraph of Example 45, starting from 0.126 g of (E)-2(R)-[(tetrahydro-2(RS)-pyranyloxy)carbamoyl]-4-phenyl-3-butenyl]-4-methyl-N-phthalimidovaleramide there was obtained 0.034 g of (E)-2(R)-[1(S)-(hydroxycarbamoyl)-4-phenyl-3-butenyl]-4-methyl-N-phthalimidovaleramide in the form of a white solid.

MS: 450 (M+H)+.

HPLC: Gradient elution using solvent A containing 5% solvent B increasing to 95% solvent B over 15 minutes; flow rate 1 ml/minute. Retention time: 12.00 minutes. Solvent A: H₂O/0.1% TFA; solvent B: CH₃CN/0.85% TFA.

Column type: HYPERPEP 300A.

The (E)-2(R)-[(tetrahydro-2(RS)-pyranyloxy)carbamoyl]-4-phenyl-3-butenyl]-4-methyl-N-phthalimidovaleramide used as the starting material was prepared as follow.

(i) A solution of 1.0 g of (E)-2(R)-[1(S)-(tertbutoxycarbonyl)-4-phenyl-3-butenyl]-4-methylvalerohydrazide and 0.41 g of phthalic anhydride in 50 ml of toluene was heated at reflux for 2 hours. The mixture was cooled and the solvent was evaporated and replaced with ethyl acetate. The ethyl acetate solution was washed with 2M aqueous hydrochloric acid, 5% aqueous sodium hydrogen carbonate and then with brine. The ethyl acetate phase was dried over anhydrous magnesium sulphate and the solvent was evaporated. The residue was trituated with diethyl ether to give 0.60 g of (E)-2(R)-[1(S)-(tertbutoxycarbonyl)-4-phenyl-3-butenyl]-4-methyl-N-phthalimidovaleramide in the form of a white solid.

MS: 443 (M+H)+.

(ii) In an analogous manner that described in Example 2, parts (iv) and (v), starting from 0.44 g of (E)-2(R)-[1(S)-(tertbutoxyarbonyl)-4-phenyl-3-butenyle-4-methyl-N-phthalimidovaleramide obtained 0.13 g of (E)-2(R)-[(tetrahydro-2(RS)-pyranyloxy)carbamoyl]-4-phenyl-3-butenyl]-4-methy-N-phthalimidovaleramide in the form of a white solid.

MS: 534 (M+H)+.

EXAMPLE 121

Methyl (E)-3-[2(R)-[1(S)-(hydroxycarbamoyl)-4-phenyl-3-butenyl]-4-methylvaleryl]-2-isobutylcarbazate In an analogous manner to that described in the first paragraph of Example 2, starting from 0.27 g of methyl (E)-3-[2(R)-[1(S)-[(tetrahydro-2(RS)-pyranyloxy)carbamoyl]-4-phenyl-3-butenyl]-4-methylvaleryl]-2-isobutylcarbazate there was obtained 0.19 g of methyl (E)-3-[2(R)-[1(S)-(hydroxycarbamoyl)-4-phenyl-3-butenyl]-4-methylvaleryl]-2-isobutylcarbazate in the form of a white solid.

MS: 434 (M+H)+.

HPLC: Gradient elution using solvent A containing solvent B increasing to 95% solvent B over 15 minutes; flow rate 1 ml/minute. Retention time: 12.08 minutes. Solvent A: H₂O/0.1% TFA; solvent B: CH₃CN/0.85% TFA.

Column type: HYPERPEP 300A.

The methyl (E)-3-[2-(R)-[1(S)-[(tetrahydro-2(RS)-pyranyloxy)carbamoyl]-4-phenyl-3-butenyl]-4-methylvaleryl]-2-isobutylcarbazate used as the starting material was prepared as follows:

(i) 0.50 g of (E)-2(R)-[1(S)-(tertbutoxycarbonyl)-4-phenyl-3-butenyl]-2'-isobutyl-4-methylvalerohydrazide and 0.12 ml of pyridine were dissolved in 10 ml of dichloromethane and cooled to 0° C. under nitrogen. 0.12 ml of methyl chloroformate and a few crystals of 4-dimethylaminopyridine were added in succession and the mixture was left to come to room temperature and then stirred for 1 hour. The mixture was diluted with dichloromethane and then washed in succession with 5% aqueous sodium hydrogen carbonate solution, water, 2M aqueous hydrochloric acid and water and then dried over magnesium sulphate. The solvent was evaporated to give 0.54 g of methyl (E)-3-[2(R)-[1(S)-(tertbutoxycarbonyl)-4-phenyl-3-butenyl]-4-methylvaleryl]-2-isobutylcarbazate in the form of a white foam.

MS: 475 (M+H)+.

(ii) In an analogous manner to that described in Example 2, parts (iv) and (v), starting from 0.54 g of methyl (E)-3-[2(R)-[1(S)-tertbutoxycarbonyl)-4-phenyl-3-butenyl]-4-methylvaleryl]-2-isobutylcarbazate there was obtained 0.27 g of methyl (E)-3-[2(R)-[1(S)-[(tetrahydro-2(RS)-pyranyloxy)carbamoyl]-4-phenyl-3-butenyl]-4-methylvaleryl]-2-isobutylcarbazate in the form of a white solid.

MS: 518 (M+H)$^+$.

EXAMPLE 122

(E)-2'-Cycloheptyl-2(R)-[1(S)-(hydroxycarbamoyl)-4-phenyl-3-butenyl]-2-(methanesulphonyl)-4-methylvalerohydrazide In an analogous manner to that described in Example 45, but using cycloheptanone in place of isobutyraldehyde in step (i), there was obtained (E)-2'-cycloheptyl-2(R)-[1(S)-(hydroxycarbamoyl)-4-phenyl-3-butenyl]-2-(methanesulphonyl)-4-methylvalerohydrazide in the form of a white solid.

MS: 494 (M+H)$^+$.

HPLC: Gradient elution using solvent A containing 5% solvent B increasing to 95% solvent B over 15 minutes; flow rate 1 ml/minute. Retention time: 12.99 minutes. Solvent A: H$_2$O/0.1% TFA; solvent B: CH$_3$CN/0.085% TFA.

Column type: HYPERPEP 300A.

EXAMPLE 123

(E)-2(R)-[1(S)-(Hydroxycarbamoyl)-4-phenyl-3-butenyl]-2'-(methanesulphonyl-4-methyl)-2-neopentylvalerohydrazide In an analogous manner to that described in Example 45, but using pivalaldehyde in place of isobutyraldehyde in step (i), there was obtained (E)-2(R)-[1(S)-(hydroxycarbamoyl)-4-phenyl-3-butenyl]-2'-(methanesulphonyl-4-methyl)-2-neopentylvalerohydrazide in the form of a white solid.

MS: 468 (M+H)$^+$.

HPLC: Gradient elution using solvent A containing 5% solvent B increasing to 95% solvent B over 15 minutes; flow rate 1 ml/minute. Retention time 12.79 minutes. Solvent A: H$_2$O/0.1% TFA; solvent B: CH$_3$CN/0.085% TFA.

Column type: HYPERPEP 300A.

EXAMPLE 124

(E)-2(R)-[1(S)-(Hydroxycarbamoyl)-4-phenyl-3-butenyl]-2'-isobutyl-2'-(trifluoroacetyl)-4-methylvalerohydrazide In an analogous manner to that described in Example 59, but using trifluoroacetic anhydride in place of isobutyric anhydride in step (i), there was obtained (E)-2(R)-[1(S)-(hydroxycarbamoyl)-4-phenyl-3-butenyl]-2'-isobutyl-2'-(trifluoroacetyl)-4-methylvalerohydrazide in the form of a white solid.

MS: 472 (M+H)$^+$.

HPLC: Gradient elution using solvent A containing 5% solvent B increasing to 95% solvent B over 15 minutes; flow rate 1 ml/minute. Retention time: 13.36 minutes. Solvent A: H$_2$O/0.1% TFA; solvent B: CH$_3$CN/0.85% TFA.

Column type: HYPERPEP 300A.

EXAMPLE 125

(E)-2(R)-[1(S)-(Hydroxycarbamoyl)-4-phenyl-3-butenyl]-2'-isobuyl-4-methyl-2'-(2-phenylacetyl)valerohydrazide In an analogous manner to that described in Example 59, but using phenylacetyl chloride in place of isobutyric anhydride in step (i), there was obtained (E)-2(R)-[1(S)-(hydroxycarbamoyl)-4-phenyl-3-butenyl]-2'-isobutyl-4-methyl-2'-(2-phenylacetyl)valerohydrazide in the form of a white solid.

MS: 494 (M+H)$^+$.

HPLC: Gradient elution using solvent A containing solvent B increasing to 95% solvent B over 15 minutes; flow rate 1 ml/minute. Retention time: 13.03 minutes. Solvent A: H$_2$O/0.1% TFA; solvent B: CH$_3$CN/0.085% TFA.

Column type: HYPERPEP 300A.

EXAMPLE 126

(E)-2(R)-[1(Hydroxycarbamoyl)-4-phenyl-3-butenyl]-N-(2-isothiazolidinyl)-4-methylvaleramide S,S-dioxide In an analogous manner to that described in the first paragraph of Example 2, starting from 0.12 g of (E)-2(R)-[1(S)-[(tetrahydro-2(RS)-pyranyloxy)carbamoyl]-4-phenyl-3-butenyl]-N-(2-isothiazolidinyl)-4-methylvaleramide S,S-dioxide there was obtained 0.03 g of (E)-2(R)-[1(S)-(hydroxycarbamoyl)-4-phenyl-3-butenyl]-N-(2-isothiazolidinyl)-4-methylvaleramide S,S-dioxide in the form of a white solid.

MS: 424 (M+H)$^+$.

HPLC: Gradient elution using solvent A containing 5% solvent B increasing to 95% solvent B over 15 minutes; flow rate 1 ml/minute. Retention time: 9.90 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy)carbamoyl]-4-phenyl-3-butenyl]-N-(2-isothiazolidinyl)-4-methylvaleramide S,S-dioxide used as the starting material was prepared as follows:

(i) 1.85 g of 3-chloropropylsulphonyl chloride and 0.85 g of pyridine were added to a solution of 3.0 g of (E)-2(R)-[1(S)-(tertbutoxycarbonyl)-4-phenyl-3-butenyl]-4-methylvalerohydrazide in 40 ml of dichloromethane. After stirring at room temperature for 2 hours the solvent was evaporated and the residue was triturated with diethyl ether. The mixture was filtered and the solvent was evaporated to give 1.92 g of (E)-2(R)-[1(S)-(tertbutoxycarbonyl)-4-phenyl-3-butenyl]-2'-(3-chloropropylsulphonyl)-4-methylvalerohydrazide in the form of a pale yellow oil.

MS: 445 (M+H−$^t$Bu)$^+$.

(ii) 1.59 g of potassium carbonate were added to a solution of 1.92 g of (E)-2(R)-[1(S)-(tertbutoxycarbonyl)-4-phenyl-3-butenyl]-2'-(3-chloropropylsulphonyl)-4-methylvalerohydrazide in 50 ml of dry dimethylformamide. After stirring at room temperature overnight the solvent was evaporated and the residue was dissolved in diethyl ether and washed with water. The organic phase was dried over anhydrous magnesium sulphate and evaporated. The residue was purified by flash chromatography on silica gel using ethyl acetate/hexane (1:2) for the elution. There was obtained 0.93 g of (E)-2(R)-[1(S)-(tertbutoxycarbonyl)-4-phenyl-3-butenyl]-N-(2-isothiazolidinyl)-4-methylvaleromide S,S-dioxide in the form of a pale yellow oil.

MS: 409 (M+H−$^t$Bu)$^+$.

(iii) In an analogous manner to that described in Example 2, parts (iv) and (v), starting from 0.90 g of (E)-2(R)-[1(S)-(tertbutoxycarbonyl)-4-phenyl-3-butenyl-N-(2-isothiazolidinyl)-4-methylvaleramide S,S-dioxide there was obtained 0.12 g of (E)-2(R)-[1(S)-[(tetrahydro-2(RS)-pyranyloxy)carbamoyl]-4-phenyl-3-butenyl-N-(2-isothiazolidinyl)-4-methylvaleramide S—S-dioxide in the form of a white solid.

MS: 508 (M+H)+.

EXAMPLE 127

(E)-2(R)-[1(S)-(Hydroxycarbamoyl)-4-phenyl-3-butenyl]-4-methyl-N-(2-oxo-3-oxazolidinyl) valeramide In an analogous manner to that described in Example 126, but using 2-bromoethyl chloroformate in place of 3-chloropropylsulphonyl chloride in step (i), there was obtained (E)-2(R)-[1(S)-(hydroxycarbamoyl)-4-phenyl-3-butenyl]-4-methyl-N-(2-oxo-3-oxazolidinyl)valeramide in the form of a white solid.

MS: 390 (M+H)+.

HPLC: Gradient elution using solvent A containing 5% solvent B increasing to 95% solvent B over 15 minutes; flow rate 1 ml/minute. Retention time: 9.79 minutes. Solvent A: H$_2$O/0.1% TFA; solvent B: CH$_3$CN/0.085% TFA. Column type: HYPERPEP 300A.

EXAMPLE 128

2(S)-[1(RS)-(Hydroxycarbamoyl)(phenylthio)methyl]-2'-isobutyl-2'-(methanesulphonyl)-4-methylvalerohydrazide In an analogous manner to that described in the first paragraph of Example 2, starting from 2.98 g of 2(S)-[1(RS)-(phenylthio)[(tetrahydro-2(RS)-pyranyloxy)carbamoyl]methyl]-2'-isobutyl-2'-(methanesulphonyl)-4-methylvalerohydrazide there were obtained 1.92 g of 2(S)-[1(RS)-(hydroxycarbamoyl)(phenylthio)methyl]-2'-isobutyl-2'-(methanesulphonyl)-4-methylvalerohydrazide in the form of a white solid.

MS: 446 (M+H)+.

HPLC: Gradient elution using solvent A containing solvent B increasing to 95% solvent B over 15 minutes. Flow rate 1 ml/min. Retention times 11.36 and 12.64 minutes. Solvent A: H$_2$O/0.1% TFA; solvent B: CH$_3$/CN/0.085% TFA. Column type: HYPERPEP 300A.

The 2(S)-[1(RS)-(phenylthio)[(tetrahydro-2(RS)-pyranyloxy)carbamoyl]methyl]-2'-isobutyl-2'-(methanesulphonyl)-4-methylvalerohydrazide used as the starting material was prepared as follows:

In an analogous manner to that described in Example 131, part (v), Example 1, part (iii), and Example 2(iii), part (v), starting from 3.45 g of 2(S)-isobutyl-3(RS)-phenylthiobutane-1.4-dioic acid 4tert.butyl ester (prepared as described in W097/42168) there was obtained 2.98 g of 2(S)-[1(RS)-(phenylthio)[(tetrahydro-2(RS)(phenylthio)[(tetrahydro-2(RS)-pyranyloxy)carbamoyl]methyl]-2'-isobutyl-2'-(methanesulphonyl)-4-methylvalerohydrazide in the form of a white solid.

MS: 530 (M+H)+.

EXAMPLE 129

2(R)-[1(S)-(Hydroxycarbamoyl)-4-methylpenyl]-2'-isobutyl-2'-(methanesulphonyl)-4-methylvalerohydrazide In an analogous manner to that described in the first paragraph of Example 2, starting from 0.77 g of 2(R)-[1(S)-[(tetrahydro-2(RS)-pyranyloxy)carbamoyl]-4-methylpentyl]-2'-isobutyl-2'-(methanesulphonyl)-4-methylvalerohydrazide there was obtained 0.48 g of 2(R)-[1(S)-(hydroxycarbamoyl)-4-methylpentyl]-2'-isobutyl-2'-(methanesulphonyl)-4-methylvalerohydrazide in the form of a white solid.

MS: 408 (M+H)+.

HPLC: Accelerating gradient elution using solvent A containing 40% solvent B for 5 minutes then increasing to 80% solvent B over 10 minutes; flow rate 1 ml/minute. Retention time: 5.61 minutes. Solvent A: H$_2$O/0.1% TFA; solvent B: CH$_3$CN/0.085% TFA. Column type: HYPERSIL 120A.

The 2(R)-[1(S)-[(tetrahydro-2(RS)-pyranyloxy)carbamoyl]-4-methylpentyl]-2'-isobutyl-2'-(methanesulphonyl)-4-methylvalerohydrazide used as the starting material was prepared as follows:

(i) A solution of 1.5 g of 2(R)-[1(S)-(tertbutoxycarbonyl)-4-methyl-3-pentenyl]-2'-isobutyl-2'-(methanesulphonyl)-4-methylvalerohydrazide in 50 ml of methanol was hydrogenated in the presence of 0.15 g of 10% palladium-on-carbon for 6 hours. The catalyst was removed by filtration and the solvent was evaporated to give 1.5 g of 2(R)-[1(S)-(tertbutoxycarbonyl)-4-methylpentyl]-2'-isobutyl-2-(methanesulphonyl)-4-methylvalerohydrazide in the form of a colourless oil.

MS: 449 (M+H)+.

(ii) In an analogous manner to that described in Example 1, part (iii), and Example 2, part (v), starting from 1.5 g of 2(R)-[1(S)-(tertbutoxycarbonyl)-4-methylpentyl]-2'-isobutyl-2-(methanesulphonyl)-4-methylvalerohydrazide there was obtained 0.77 g of 2(R)-[1(S)-[(tetrahydro-2(RS)-pyranyloxy)carbamoyl]-4-methylpentyl]-2'-isobutyl-2'-(methanesulphonyl)-4-methyl-valerohydrazide in the form of a white solid.

MS: 492 (M+H)+.

EXAMPLE 130

2(R)-[1(S)-(Hydroxycarbamoyl)-4-methyl-3-pentenyl]-2'-isobutyl-2'-(methanesulphonyl)-4-methylvalerohydrazide In an analogous manner to that described in the first paragraph of Example 2, starting from 0.25 g of 2(R)-[1(S)-[(tetrahydro-2(RS)-pyranyloxy)carbamoyl]-4-methyl-3-pentenyl]-2'-isobutyl-2'-(methanesulphonyl)-4-methylvalerohydrazide there was obtained 0.16 g of 2(R)-[1(S)-(hydroxycarbamoyl)-4-methyl-3-pentenyl]-2'-isobutyl-2'-(methanesulphonyl)-4-methylvalerohydrazide in the form of a white solid.

MS: 406 (M+H)+.

HPLC: Gradient elution using solvent A containing 5% solvent B increasing to 98% solvent B over 15 minutes; flow rate 1 ml/minute. Retention time: 11.59 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy)carbamoyl]-4-methyl-3-pentenyl]-2'-isobutyl-2'-(methanesulphonyl)-4-methylvalerohydrazide used as the starting material was prepared as follows:

(i) A solution of 1.5 g of 2(R)-[1(S)-(tertbutoxycarbonyl)-4-methyl-3-pentenyl]-2'-isobutyl-2'-(methanesulphonyl)-4-methylvalerohydrazide, 0.51 g of triethylamine and 0.93 g trimethylsilyl triflate in 20 ml of 1,4-dioxane was heated at reflux under a nitrogen atmosphere for 4 hours. The mixture was cooled and the solvent was evaporated. The residue was dissolved in ethyl acetate and washed with 2M aqueous hydrochloric acid, water and brine. The ethyl acetate phase was then dried over anhydrous magnesium sulphate and the solvent was evaporated to give 1.31 g of 2(R)-[1(S)-(carboxy)-4-methyl-3-pentenyl]-2'-isobutyl-2'-(methanesulphonyl)-4-methylvalerohydrazide in the form of a yellow foam.
MS: 391 (M+H)+.

(ii) In an analogous manner to that described in Example 2, part (v), starting from 1.31 g of 2(R)[1(S)-(carboxy)-4-methyl-3-pentenyl]-2'-isobutyl-2'-(methanesulphonyl)-4-methylvalerohydrazide there was obtained 0.25 g of 2(R)-[1(S)-[(tetrahydro-(RS)-pyranyloxy)carbamoyl]-4-methyl-3-pentenyl]-2'-isobutyl-2'-(methanesulphonyl)-4-methylvalerohydrazide in the form of a pale yellow foam.
MS: 490 (M+H)+.

EXAMPLE 131

2(R)-[(S)-(Benzyloxy)-(hydroxycarbamoyl)methyl]-2-isobutyl-2'-(methanesulphonyl)-4-methylvalerohydrazide In an analogous manner to that described in the first paragraph of Example 45, starting from 0.12 g of 2(R)-[(S)-(benzyloxy)-[(tetrahydro-2(RS)-pyranyloxy)carbamoyl]methyl]-2'-isobutyl-2'-(methanesulphonyl)-4-methylvalerohydrazide there was obtained 0.07 g of 2(R)-[(S)-(benzyloxy)-hydroxycarbamoyl]methyl]-2'-isobutyl-2'-(methanesulphonyl)-4-methylvalerohydrazide in the form of a white solid.
MS: 444 (M+H)+.

HPLC: Gradient elution using solvent A containing 5% solvent B increasing to 98% solvent B over 15 minutes; flow rate 1 ml/minute. Retention time: 11.86 minutes. Solvent A: $H_2O$/0.1% TFA; solvent B: $CH_3CN$/0.085% TFA.
Column type: HYPERPEP 300A.

The 2(R)-[(S)-(benzyloxy)-[(tetrahydro-2(RS)-pyranyloxy)carbamoyl]methyl]-2'-isobutyl-2'-(methanesulphonyl)-4-methylvalerohydrazide used as the starting material was prepared as follow:

(i) 4.48 g of 3(R)-carboxy-2(S)-hydroxy-5-methylhexanoic acid were stirred under nitrogen in 10 ml of trifluoroacetic anhydride for 1.5 hours. The solvent was evaporated and the residue was dissolved in 20 ml of dry methanol and stirred overnight at room temperature. The solvent was evaporated to give 5.3 g of methyl 3(R)-carboxy-2(S)-hydroxy-5-methylhexanoate in the form of an orange oil.

(ii) 2.1 ml of allyl bromide were added to a solution of 4.52 g of methyl 3(R)-carboxy-2(S)-hydroxy-5-methylhexanoate and 7.9 g of caesium carbonate in 30 ml of dimethylformamide. The mixture was stirred overnight and then evaporated. The residue was dissolved in dichloromethane and washed with 2M aqueous hydrochloric acid. The dichloromethane phase was then dried over anhydrous magnesium sulphate and the solvent was evaporated. The residue was purified by flash chromatography on silica gel using ethyl acetate/hexane (1:9 increasing to 2:8) for the elution. There were obtained 2.88 g of methyl 3(R)-(allyloxycarbonyl)-2(S)-hydroxy-5-methylhexanoate in the form of a pale yellow oil.

(iii) 0.51 g of silver(I) oxide and 0.33 ml of benzyl bromide were added to a solution of 0.27 g of methyl 3(R)-(allyloxycarbonyl)-2(S)-hydroxy-5-methylhexanoate in 5 ml of dimethylformamide. After stirring the mixture for 24 hours, 0.36 g of cesium carbonate were added and stirring was continued for 3 hours. The mixture was diluted with diethyl ether and filtered. The filtrate was then washed in succession with 5% aqueous citric acid, water, 5% aqueous sodium hydrogen carbonate, water and brine. The diethyl ether phase was dried over anhydrous magnesium sulphate and the solvent was evaporated. The residue was purified by flash column chromatography on silica gel using ethyl acetate/hexane (1:19) for the elution. There was obtained 0.16 g of methyl 3(R)-(allyloxycarbonyl)-2(S)-benzyloxy-5-methylhexanoate in the form of a clear oil.

(iv) 0.39 ml of morpholine and 0.05 g of tetrakis (triphenylphosphine)palladium(0) were added to a stirred solution of 0.15 g of methyl 3(R)-(allyloxycarbonyl)-2(S)-benzyloxy-5-methylhexanoate in 5 ml of tetrahydrofuran under a nitrogen atmosphere. After stirring the mixture for 0.5 hour the solvent was evaporated. The residue was dissolved in dichloromethane and washed in succession with 2M aqueous hydrochloric acid and water. The organic phase was dried over anhydrous magnesium sulphate and the solvent was evaporated. The residue was dissolved in diethyl ether and filtered. The diethyl ether solution was evaporated to give 0.16 g of methyl 3(R)-carboxy-2(S)-benzyloxy-5-methylhexanoate in the form of a yellow oil.

(v) In an analogous manner to that described in Example 1, part (i), but using isobutylhydrazine in place of phenylhydrazine,and part (ii), starting from 0.43 g of methyl 3(R)-carboxy-2(S)-benzyloxy-5-methylhexanoate there was obtained 0.34 g of 2(R)-[(S)-(benzyloxy)-(methoxycarbonyl)methyl]-2'-isobutyl-2'-(methanesulphonyl)-4-methylvalerohydrazide in the form of a yellow oil.
MS: 443 (M+H)+.

(vi) 0.530 ml of a 2M solution of trimethylaluminium in toluene was added to a solution of 0.124 g of O-(tetrahydro-2H-pyran-2(RS)-yl)-hydroxylamine in 5 ml of dry toluene at 0° C. under a nitrogen atmosphere. The mixture was stirred at 0° C. for 0.5 hours and then 0.335 g of 2(R)-[(S)-(benzyloxy)(methoxycarbonyl) methyl]-2'-isobutyl-2'-(methanesulphonyl)-4-methylvalerohydrazide was added in one portion. The mixture was then left to warm to room temperature overnight. The mixture was diluted with ethyl acetate and washed in succession with 2M aqueous hydrochloric acid and 5% aqueous sodium hydrogen carbonate solution and then dried over anhydrous magnesium sulphate. The solvent was evaporated and the residue was triturated with hexane/diethyl ether (2:1) to give 0.119 g of 2(R)-[(S)-(benzyloxy)-[(tetrahydro-2(RS)-pyranyloxy)-carbamoyl]methyl]-2'-isobutyl-2'-(methanesulphonyl)-4-methylvalerohydrazide in the form of a white solid.
MS: 528 (M+H)+.

EXAMPLE 132

2(R)-[1(S)-(Hydroxycarbamoyl)-2-phenylethyl]-2'-isobutyl-2'-(methanesulphonyl)-4-methylvalerohydrazide In an analogous manner to that described in the first paragraph of Example 65, starting from 0.063 g of 2(R)-[1 (S)-(benzyloxycarbamoyl)-2-phenylethyl]-2'-isobutyl-2'-(methanesulphonyl)-4-methylvalerohydrazide there was obtained 0.014 g of 2(R)-[1(S)-hydroxycarbamoyl)-2- phenylethyl]-2'-isobutyl-2'-(methanesulphonyl)-4-methylvalerohydrazide in the form of a white solid.
MS: 428 (M+H)$^+$.

HPLC: Gradient elution using solvent A containing 5% solvent B increasing to 95% solvent B over 10 minutes; flow rate 2 ml/minute. Retention time: 7.55 minutes. Solvent A: H$_2$O/0.1% TFA; solvent B: H$_2$O/90% CH$_3$CN/0.085% TFA. Column type: DYNAMAX 300A.

The 2(R)-[1(S)-(benzyloxyarbamoyl)-2-phenylethyl]-2'-isobutyl-2'-(methanesulphonyl)-4-methylvalerohydrazide used as the starting material was prepared as follows:

(i) In an analogous manner to that described in Example 2, parts (i) and (ii), but using benzyl bromide in place of cinnamyl bromide in step (i), there was obtained 2(R)-[1(S)-(tertbutoxy-carbonyl)-2-phenylethyl]-4-methylvaleric acid is the form of a clear oil.
MS: 321 (M+H)$^+$.

(ii) In an analogous manner to that described in Example 131, part (v) and Example 65 parts (iii) and (iv), from 1.49 g of 2(R)-[1(S)-(tertbutoxycarbonyl)-2-phenylethyl]-4-methylvaleric acid there was obtained 0.063 g of 2(R)-[1(S)-(benzyloxy-carbamoyl)-2-phenylethyl]-2'-isobutyl-2'-(methanesulphonyl)-4-methylvalerohydrazide in the form of a white solid.
MS: 518 (M+H)$^+$.

EXAMPLE 133

2(R)-[1(S)-(Hydroxycarbamoyl)-2-(phenylthio)ethyl]-2'-isobutyl-2'-(methanesulphonyl)-4-methylvalerohydrazide In an analogous manner to that described in the first paragraph of Example 2, starting from 0.315 g of 2(R)-[1(S)-[(tetrahydro-2(RS)-pyranyloxy)carbamoyl]-2-(phenylthio)ethyl]-2'-isobutyl-2-(methanesulphonyl)-4-methylvalerohydrazide there was obtained 0.116 g of 2(R)-[1(S)-(hydroxycarbamoyl)-2-(phenylthio)ethyl]-2'-isobutyl-2'-(methanesulphonyl)-4-methylvalerohydrazide in the form of a white solid.
MS: 460(M+H)$^+$.

HPLC: Gradient elution using solvent A containing 5% solvent B increasing to 95% solvent B over 15 minutes; flow rate 1 ml/minute. Retention time: 11.95 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy)carbamoyl]-2-(phenylthio)ethyl]-2'-isobutyl-2'-(methanesulphonyl)-4-methylvalerohydrazide used as the starting material was prepared as follows:

(i) 7.8 ml of piperidine and 20 ml of a 40% aqueous formaldehyde solution were added to a solution of 6.0 g of 1-tert.butyl dihydrogen 4-methyl-1(RS),1,2(R)-pentanetricarboxylate in 80 ml of isopropyl alcohol and the mixture was stirred overnight under a nitrogen atmosphere. The solvent was evaporated and the residue was dissolved in ethyl acetate. The ethyl acetate phase was washed in succession with 1M aqueous hydrochloric acid, warm water and brine and the dried over anhydrous magnesium sulphate. The solvent was evaporated to give 3.94 g of 2(R)-[1-(tertbutoxycarbonyl)vinyl]-4-methylvaleric acid in the form of a clear oil.

(ii) In an analogous manner to that described in Example 131, part (v), starting from 3.4 g of 2(R)-[1-(tertbutoxycarbonyl)vinyl]-4-methylvaleric acid there were obtained 3.57 g of 2(R)-[1-(tertbutoxycarbonyl)vinyl]-2'-isobutyl-2'-(methanesulphonyl)-4-methylvalerohydrazide in the form of a clear oil.

(iii) 0.183 g of thiophenol and 0.356 ml of triethylamine were added to a solution of 0.500 g of 2(R)-[1(tertbutoxycarbonyl)vinyl]-2'-isobutyl-2'-(methanesulphonyl)-4-methylvalerohydrazide in 20 of toluene and stirring under a nitrogen atmosphere was continued for 48 hours. A further 0.183 ml of thiophenol was added to the mixture and stirring was continued for 48 hours at 60° C. The mixture was then cooled to room temperature and diluted with ethyl acetate. The mixture was washed in succession with 1M aqueous hyrochloric acid, 1M aqueous sodium hydroxide and brine. The organic phase was dried over anhydrous magnesium sulphate and the solvent was evaporated. Trituration with hexane gave 0.307 g of 2(R)-[1(S)-(tertbutoxycarbonyl)-2-(phenylthio)ethyl]-2'-isobutyl-2'-(methanesulphonyl)-4-methylvalerohydrazide in the form of a white solid.
MS: 501 (M+H)$^+$.

(iv) In an analogous manner to that described in Example 2, parts (iv) and (v), starting from 0.307 g of 2(R)-[1(S)-(tertbutoxycarbonyl)-2-(phenylthio)ethyl]-2'-isobutyl-2'-(methanesulphonyl)-4-methylvalerohydrazide there was obtained 0.315 g of 2(R)-[1(S)-[(tetrahydro-2(RS)-pyranyloxy)carbamoyl]-2-(phenylthio)ethyl]]-2'-isobutyl-2'-(methanesulphonyl)-4-methylvalerohydrazide in the form of a white solid.
MS: 544 (M+H)$^+$.

EXAMPLE 134

(E)-2(R)-[1(S)-(Hydroxycarbamoyl)-4-(1-naphthyl)-3-butenyl]-2'-isobutyl-2'-(methanesulphonyl)-4-methylvalerohydrazide In an analogous manner to that described in the first paragraph of Example 2, starting from 0.240 g of (E)-2(R)-[1(S)-[(tetrahydro-2(RS)-pyranyloxy)carbamoyl]-4-(1-naphthyl)-3-butenyl]-2'-isobutyl-2'-(methanesulphonyl)-4-methylvalerohydrazide there was obtained 0.155 g of (E)-2(R)-[1(S)-(hydroxycarbamoyl)-4-(1-naphthyl)-3-butenyl-2'-isobutyl-2'-(methanesulphonyl)-4-methyl-valerohydrazide in the form of a white solid.
MS: 504 (M+H)$^+$.

HPLC: Gradient elution using solvent A containing 5% solvent B increasing to 95% solvent B over 15 minutes; flow rate 1 ml/minute. Retention time: 13.19 minutes. Solvent A: H$_2$O/0.1% TFA; solvent B: CH$_3$CN/0.085% TFA.
Column type: HYPERPEP 300A.

The (E)-2(R)-[1(S)-[(tetrahydro-2(RS)-pyranyloxy)carbamoyl]-4-(1-naphthyl)-3-butenyl]-2'-isobutyl-2'-(methanesulphonyl)-4-methylvalerohydrazide used as the starting material was prepared as follows:

0.500 g of 2(R)-[1(S)-[(tetrahydro-2(RS)-pyranyloxy)carbamoyl]-3-butenyl]-2'-(methanesulphonyl)-4-methyl-2'-phenylvalerohydrazide, prepared as described in Example 118, 0.449 g of 1-bromo-naphthalene, 0.219 g of triethylamine, 0.012 g of palladium(II) acetate and 0.033 g of tri-o-tolylphosphine were dissolved in 5 ml of dimethylformnamide and stirred at 100° C. for 24 hours. The mixture was then cooled to room temperature and partitioned between water and ethyl acetate. The aqueous phase was extracted twice with ethyl acetate and then the combined organic phases were dried over anhydrous magnesium sulphate. The solvent was evaporated and the residue was purified by flash chromatography on silica gel using dichloromethane/methanol (9.5/0.5) for the elution. There was obtained 0.260 g of (E)-2(R)-[1(S)-[(tetrahydro-2(RS)-pyranyloxy)carbamoyl]-4-(1-naphthyl)-3-butenyl]-2'-isobutyl-2'-(methanesulphonyl)-4-methylvalerohydrazide in the form of a white solid.

MS: 504 (M−THP+H)$^+$.

EXAMPLE 135

(E)-2(R)-[1(S)-(Hydroxycarbamoyl)-4-(5-pyrimidinyl)-3-butenyl]-2'-isobutyl-2'-(methanesulphonyl)-4-methylvalerohydrazide In an analogous manner to that described in Example 134, but using 5-bromopyrimidine in place of 1-bromonaphthalene, there was obtained (E)-2(R)-[1(S)-(hydroxycarbamoyl)-4-(5-pyrimidinyl)-3-butenyl]-2'-isobutyl-2'-(methanesulphonyl)-4-methylvalerohydrazide in the form of a white solid.

MS: 456 (M+H)$^+$.

HPLC: Gradient elution using solvent A containing 5% solvent B increasing to 95% solvent B over 15 minutes; flow rate 1 ml/minute. Retention time: 9.89 minutes. Solvent A: H$_2$O/0.1% TFA; solvent B: CH$_3$CN/0.085% TFA. Column type: HYPERPEP 300A.

EXAMPLE 136

2(R)-[(S)-(Cyclopentyl)(hydroxycarbamoyl)methyl]-2'-isobutyl-2'-(methanesulphonyl-4-methylvalerohydrazide and 2(R)-[(S)-(cyclopentyl)(hydroxycarbamoyl)methyl]-2'-isobutyl-2'-(methanesulphonyl)-4-methyl-3-pentenohydrazide In an analogous manner to that described in the first paragraph of Example 45, starting from 0.357 g of a mixture of 2(R)-[(S)-(cyclopentyl)[(tetrahydro-2(RS)-pyranyloxy)carbamoyl]methyl]-2'-isobutyl-2'-(methanesulphonyl)-4-methylvalerohydrazide and 2(R)-[(S)-(cyclopentyl)[(tetrahydro-2(RS)-pyranyloxy)carbamoyl]methyl]-2'-isobutyl-2'-(methanesulphonyl)-4-methyl-3-pentenohydrazide there was obtained 0.219 g of a mixture of 2(R)-[(S)-(cyclopenyl)(hydroxycarbamoyl)methyl]-2'-isobutyl-2'-(methanesulphonyl-4-methyl-3-pentenohydrazide (compound A) and 2(R)-[(S)-(cyclopentyl)hydroxycarbamoyl)methyl]-2'-isobutyl-2'-(methanesulphonyl)-4-methyl-3-pentenohydrazide (compound B) in the form of a white solid. The compounds were then separated by preparative high-performance liquid chromatography on a DYNAMAX 5 mm C18 300A column with dimensions of 21.4×50 mm using the gradient elution method specified below:

Compound A: MS: 405 (M+H)$^+$.

HPLC: Gradient elution using solvent B over 15 minutes; flow rate 1 ml/minute. Retention time; 11.00 minutes.

Compound B: MS: 403 (M+H)$^+$.

HPLC: Gradient elution as described for compound A. Retention time; 10.77 minutes.

The mixture of 2(R)-(R)-[(S)-(cyclopentyl)[(tetrahydro-2(RS)-pyranyloxy)carbamoyl]methyl]-2'-isobutyl-2'-(methanesulphonyl)-4-methylvalerohydrazide and 2(R)-[(S)-(cyclopentyl)[(tetrahydro-2(RS)-pyranyloxy)carbamoyl]methyl]-2'-isobutyl-2'-(methanesulphonyl)-4-methyl-3-pentenohydrazide used as the starting material was prepared as follows.

(i) In an analogous manner to that described in Example 131, part (v), starting from 1.1 g of 2(S)cyclopentyl-3(R)-(2-methylally)succinate acid 4-benzyl ester (prepared as described in WO 97/19053) there was obtained 1.14 g of 2(R)-[(S)-(benzyloxycarbonyl)(cyclopentyl)methyl]-2'-isobutyl-2'-(methanesulphonyl)-4-methyl-4-pentenohydrazide in the form of a white foam which could be recrystallized from hexane.

(ii) A solution of 1.14 g of 2(R)-[(S)-(benzyloxycarbonyl)(cyclopentyl)methyl]-2'-isobutyl-2'-(methanesulphonyl)-4-methyl-4-pentenohydrazide in 10 ml of ethanol was hydrogenated in the presence of 0.05 g of 10% palladium-on-carbon for 48 hours. The catalyst was removed by filtration and the solvent was evaporated to give 0.91 g of a mixture of 2(R)-[(S)-(carboxy)cyclopentyl)methyl]-2'-isobutyl-2'-(methanesulphonyl)-4-methylvalerohydrazide and 2(R)-[(S)-(carboxy)(cyclopentyl)methyl]-2'-isobutyl-2'-(methanesulphonyl)-4-methyl-3-pentenohydrazide in the form of a white foam.

(iii) In an analogous manner to that described in Example 2, part (v), starting from 0.91 g of a mixture of 2(R)-[(S)-(carboxy)(cyclopentyl)methyl]-2'-isobutyl-2'-(methanesulphonyl)-4-methylvalerohydrazide and 2(R)-[(S)-(carboxy)(cyclopentyl)methyl]-2'-isobutyl-2'-(methanesulphonyl)-4-methyl-3-pentenohydrazide there was obtained 0.357 g of a mixture of 2(R)-[(S)-(cyclopentyl)[(tetrahydro-2(RS)-pyranyloxy)carbamoyl]methyl]-2'-isobutyl-2'-(methanesulphonyl)-4-methylvalerohydrazide and 2(R)-[(S)-(cyclopentyl)[(tetrahydro-2(RS)-pyranyloxy)carbamoyl]methyl]-2'-isobutyl-2'-2'-(methanesulphonyl)-4-methyl-3-pentenohydrazide in the form of a white solid.

MS: 512 (M+Na)$^+$ and 510 (M+Na)$^+$.

EXAMPLE 137

In an analogous manner to that described in the first paragraph of Example 45, starting from (E)-2(R)-[1(S)-[(tetrahydro-2(RS)-pyranyloxy)carbamoyl]-4-phenyl-3-butenyl]-2'-[2-( 1-imidizolyl)ethyl]-2'-(methanesulphonyl)-4-methylvalerohydrazide there was obtained (E)-2(R)-[1(S)-(hydroxycarbamoyl)-4-phenyl-3-butenyl]-2'-[2-(1-imidazoyl)ethyl]-2'-(methanesulphonyl)-4-methylvalerohydrazide methanesulphonic acid salt in the form of a white solid.

MS: 492 (M+H)$^+$.

HPLC: Gradient elution using solvent A containing 5% solvent B increasing to 95% solvent B over 15 minutes; flow rate 1 ml/minute. Retention time: 9.84 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-[2-(1imidizolyl)ethyl]-2'-(methanesulphonyl)-4-methylvalerohydrazide used as starting material was prepared in an analogous manner to that described in Example 15, part (iii), starting from (E)-2(R)-[(S)-[(tetrahydro-2(RS)-pyranyloxy)carbamoyl]-4-phenyl-3-butenyl]-2'-(methanesulphonyl)-4-methylvalerohydrazide by reaction with 1-(2-bromoethyl) imidazole.

EXAMPLE 138

(Z)-2(R)-[1(S)-(Hydroxycarbamoyl)-4-phenyl-3-butenyl]-2'-isobutyl-2'-(methanesulphonyl)-4-methylvalerohydrazide In a manner analogous to that described in the first paragraph of Example 2, starting from 0.075 g of (Z)-2(R)-

[1(S)-[(tetrahydro-2(RS)-pyranyloxy)carbanoyl]-4-phenyl-3-butenyl]-2'-isobutyl-2'-(methanesulphonyl)-4-methylvalerohydrazide there was obtained 0.047 g of (Z)-2(R)-[1(S)-(hydroxycarbamoyl)-4-phenyl-3-butenyl]-2'-isobutyl-2'-(methanesulphonyl)-4-methylvalerohydrazide in the form of a white solid.
MS: 454 (M+H)+.

HPLC: Gradient elution using solvent A containing 5% solvent B increasing to 95% solvent B over 15 minutes; flow rate 1 ml/minute. Retention time: 12.19 minutes. Solvent A: H₂O/0.1% TFA; solvent B: CH₃CN/0.085% TFA. Column type: HYPERPEP 300A.

The starting material was prepared as follows:

(i) A solution of 0.1 g of 2(R)-[1(S)-tert-butoxycarbonyl)-4-phenyl-3-butynyl]-2'-isobutyl-4-methylvalerohydrazide in 10 ml of pyridine was shaken in a hydrogen atmosphere in the presence of 5% palladium-on-barium sulphate catalyst. After 45 minutes the catalyst was filtered off and the pyridine was evaporated. The residue was evaporated a further three times from toluene and there was obtained 0.1 g of (Z)-2(R)-[1(S)-(tert-butoxyarbonyl)-4-phenyl-3-butenyl]-2'-isobutyl-4-methylvalerohydrazide in the form of a straw coloured solid.
MS: 417 (M+H)+.

(ii) In an analogous manner to that described in Example 2, parts (iv) and (v) from (Z)-2(R)-[1(S)-(tert-butoxycarbonyl)-4-phenyl-3-butenyl]-2'-isobutyl-4-methylvalerohydrazide there was obtained 0.075 g of (Z)-2(R)-[1(S)-[(tetrahydro-2(RS)-pyranyloxy)carbamoyl]-4-phenyl-3-butenyl-2'-isobutyl-2'-(methanesulphonyl)-4-methylvalerohydrazide in the form of a white solid.
MS: 538 (M+H)+.

EXAMPLE 139

(E)-2(R)-[1(S)-(Hydroxycarbamoyl)-4-phenyl-3-butenyl]-2'-(methansulphonyl)-4-methyl-2'-[(2-pyridinyl)methyl[valerohydrazide methanesulphonate In an analogous manner to that described in the first paragraph of Example 2, but using methanesulphonic acid in place of p-toluenesulphonic acid, starting from 0.266 g of (E)-2(R)-[1(S)-[(tetrahydro-2(RS)-pyranyloxy)carbamoyl]-4-phenyl-3-butenyl-2'-isobutyl-2'-(methanesulphonyl)-4-methyl-2'-[(2-pyridyl)methyl]valerohydrazide there was obtained 0.24 g of (E)-2(R)-[1(S)-(hydroxycarbamoyl)-4-phenyl-3-butenyl]-2'-(methansulphonyl)-4-methyl-2'-[(2-pyridinyl)methyl]valerohydrazide methanesulphonate in the form of an off-white solid.
MS: 489 (M+H)+.

HPLC: Gradient elution using solvent A containing 5% solvent B increasing to 95% solvent B over 15 minutes; flow rate 1 ml/minute. Retention time: 9.95 minutes. Solvent A: H₂O/0.1% TFA; solvent B: CH₃CN/0.085% TFA.
Column type: HYPERPEP 300A.

The starting material was prepared in an analogous manner to that described in Example 15, part (iii), starting from (E)-2(R)-[1(S)-(tetrahydro-2(RS)-pyranyloxy)carbamoyl]-4-phenyl-3-butenyl]-2'-(methanesulphonyl)-4-methylvalerohydrazide and 2-bromomethylpyridine hydrobromide.

EXAMPLE 140

(E)-2(R)-[1(S)-(Hydroxycarbamoyl)-4-phenyl-3-butenyl]-2'-(methanesulphonyl)-4-methyl-2'-(2,6-dimethyl-4-pyrimidinyl)valerohydrazide methanesulphonate In a manner to that described in the first paragraph of Example 2, but using methanesulphonic acid in place of p-toluenesulphonic acid, starting from 0.049 g of (E)-2(R)-[1(S)-[(tetrahydro-2-(RS)pyranyloxy)carbamoyl]-4-phenyl-3-butenyl]-2'-(methanesulphonyl)-4-methyl-2'-(2,6-dimethyl-4-pyrimidinyl)valerohydrazide there was obtained 0.039 g of (E)-2(R)-[1(S)-(hydroxycarbamoyl)- 4-phenyl-3-butenyl]-2'-(methanesulphonyl)-4-methyl-2'-(2,6-dimethyl-4-pyrimidinyl)valerohydrazide methanesulphonate in the form of an off-white solid.
MS: 504 (M+H)+.

HPLC: Gradient elution using solvent A containing 5% solvent B increasing to 95% solvent B over 15 minutes; flow rate 1 ml/minute. Retention time: 12.00 minutes. Solvent A: H₂O/0.1% TFA; solvent B: CH₃CN/0.085% TFA. Column type: HYPERPEP 300A.

The starting material was prepared in an analogous manner to that described in Example 2, parts (iii)–(v), starting from (E)-2(R)-[1(S)-(tert-butoxycarbonyl)-4-phenyl-3-butenyl]-4-methylvaleric acid and 2,4-dimethyl-6-hydrazinopyrimidine.

EXAMPLE A

Tablets containing the following ingredients may be produced in a conventional manner:

| Ingredient | Per tablet |
| --- | --- |
| Hydrazine derivative | 10.0 mg |
| Lactose | 125.0 mg |
| Corn starch | 75.0 mg |
| Talc | 4.0 mg |
| Magnesium stearate | 1.0 mg |
| Total weight | 215.0 mg |

EXAMPLE B

Capsules containing the following ingredients may be produced in a conventional manner:

| Ingredient | Per capsule |
| --- | --- |
| Hydrazine derivative | 10.0 mg |
| Lactose | 165.0 mg |
| Corn starch | 20.0 mg |
| Talc | 5.0 mg |
| Capsule fill weight | 200.0 mg |

What is claimed is:
1. Compounds of the general formula:

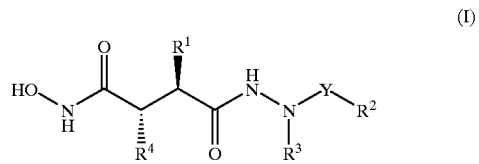

(I)

wherein
Y is CO or SO₂;
R¹ is lower alkyl, lower alkenyl, lower cycloalkyl, lower cycloalkyl-lower alkyl, aryl or aryl-lower alkyl;
R² is lower alkyl, halo-lower alkyl, aryl-lower alkyl, aryl-lower alkenyl or aryl when Y is SO₂ and is lower alkyl, halo-lower alkyl, lower alkoxy, lower alkoxycarbonyl, acyl, lower cycloalkyl, aryl, aryl-lower alkyl, aryl-lower alkoxy or $NR^5R^6$ when Y is CO; and $R^3$ is hydrogen, lower alkyl optionally substituted by cyano, amino, hydroxy, lower alkoxy, lower alkoxycarbonyl, heterocyclyl or heterocyclylcarbonyl, lower alkenyl, lower alkynyl, lower cycloalkyl, lower cycloalkyl-lower alkyl, aryl-lower alkyl, aryl-lower alkenyl, aryl or heterocyclyl; or $R^2$ and $R^3$ together form the residue of a 5-, 6- or 7-membered cyclic amide, cyclic imide, cyclic sulphonamide or cyclic urethane group;

$R^4$ is lower alkyl, lower alkenyl, lower cycloalkyl, lower cycloalkyl-lower alkyl or a group of the formula X-aryl, X-heteroaryl or —$(CH_2)_{1-2}$—CH=$CR^7R^8$;

X is a spacer group;

$R^5$ and $R^6$ each individually are hydrogen, lower alkyl or aryl-lower alkyl; and $R^7$ and $R^8$ together represent a lower alkylene group in which one methylene group is optionally replaced by a hetero atom;

and pharmaceutically acceptable salts thereof.

2. Compounds of claim 1, wherein Y is CO or $SO_2$; $R^1$ is lower alkyl, lower cycloalkyl, lower cycloalkyl-lower alkyl, aryl or aryl-lower alkyl; $R^2$ is lower alkyl, aryl-lower alkyl or aryl when Y is $SO_2$ and is lower alkyl, lower alkoxy, lower cycloalkyl, aryl-lower alkoxy or $NR^5R^6$ when Y is CO; and $R^3$ is hydrogen, lower alkyl optionally substituted by cyano or amino, lower alkenyl, lower alkynyl, lower cycloalkyl, lower cycloalkyl-lower alkyl, aryl-lower alkyl, aryl or heterocyclyl; or $R^2$ and $R^3$ together form the residue of a 5-, 6- or 7-membered cyclic amide, cyclic imide or cyclic sulphonamide group; $R^4$ is a group of the formula X-aryl or X-heteroaryl; X is a spacer group; heteroaryl is C-bonded; and $R^5$ and $R^6$ each individually are hydrogen, lower alkyl or aryl-lower alkyl; and pharmaceutically acceptable salts thereof.

3. Compounds of claim 2, wherein Y is CO; $R^1$ is lower alkyl; $R^2$ is lower alkoxy; $R^3$ is lower alkyl, lower alkenyl, aryl-lower alkyl or aryl; $R^4$ is X-aryl; and X is a group of the formula —$(CH_2)_{1-5}$—; —$CH_2$—CH=CH—, —$CH_2$—C≡C—, —$CH_2NHCO$—, —$(CH_2)_{1\ or\ 2}NHCONH$—, —$(CH_2)_{1-5}$—S—, —$CH_2NHSO_2$—, —$CH_2NHCH_2$—, —$(CH_2)_{1-5}$—O—, —O—$(CH_2)_{1-5}$— or —S—.

4. A compound of claim 3, wherein $R^1$ and $R^3$ are isobutyl; $R^2$ is methoxy; $R^3$ is isobutyl, 2-methylbutyl, 2-methylallyl, unsubstituted benzyl or unsubstituted phenyl; $R^4$ is phenyl, and X is —$CH_2$—CH=CH—.

5. Compounds of claim 2 wherein Y is $SO_2$; $R^1$ is lower alkyl; $R^2$ is lower alkyl; $R^3$ is lower alkyl, lower alkenyl, aryl-lower alkyl or aryl; $R^4$ is X-aryl; and X is a group of the formula —$(CH_2)_{1-5}$—; —$CH_2$—CH=CH—, —$CH_2$—C≡C—, —$CH_2NHCO$—, —$(CH_2)_{1\ or\ 2}NHCONH$—, —$(CH_2)_{1-5}$—S—, —$CH_2NHSO_2$, —$CH_2NHCH_2$—, —$(CH_2)_{1-5}$—O—, —O—$(CH_2)_{1-5}$— or —S—.

6. A compound of claim 5, wherein $R^1$ is isobutyl; $R^2$ is methyl; $R^3$ is isobutyl, 2-methylbutyl, 2-methylallyl, unsubstituted benzyl or unsubstituted phenyl; $R^4$ is phenyl, and X is —$CH_2$—CH=CH—.

7. Compounds of claim 2, wherein Y is CO and $R^2$ is lower alkoxy.

8. Compounds of claim 2, wherein Y is $SO_2$ and $R^2$ is lower alkyl.

9. Compounds of claim 7, wherein $R^2$ is methoxy.

10. Compounds of claim 8, wherein $R^2$ is methyl.

11. Compounds of claim 2, wherein $R^1$ is lower alkyl.

12. Compounds of claim 11, wherein $R^1$ is isobutyl.

13. Compounds of claim 2, wherein $R^3$ is lower alkyl, lower alkenyl, aryl-lower alkyl or aryl.

14. Compounds of claim 13, wherein $R^3$ is isobutyl, 2-methylbutyl, 2-methylallyl, unsubstituted benzyl or unsubstituted phenyl.

15. Compounds of claim 2, wherein X is a group of the formula —$(CH_2)_{1-5}$—, —$CH_2$—CH=CH—, —$CH_2$—C≡C—, —$CH_2NHCO$—, —$(CH_2)_{1\ or\ 2}NHCONH$—, —$(CH_2)_{1-5}$—S—, —$CH_2NHSO_2$—, —$CH_2NHCH_2$—, —$(CH_2)_{1-5}$—O—, —O—$(CH_2)_{1-5}$— or —S—.

16. Compounds of claim 15, wherein X is a group of the formula —$(CH_2)_{1-5}$—, —$CH_2$—CH=CH—, —$CH_2$—C≡C—, —$CH_2NHCO$—, —$(CH_2)_{1\ or\ 2}NHCONH$—, —$CH_2S$—, —$CH_2NHSO_2$— or —$CH_2NHCH_2$—.

17. Compounds of claim 2, wherein $R^4$ is a group of the formula X-aryl.

18. Compounds of claim 16, wherein X is a group of the formula —$CH_2$—CH=CH—.

19. Compounds of claim 17, wherein $R^4$ is X-phenyl.

20. Compounds of claim 19, where X is —$CH_2$—CH=CH—.

21. A compound of claim 2 selected from the group consisting of:

(E)-2(R)-[1(S)-(Hydroxycarbamoyl)-4-phenyl-3-butenyl]-2'-isobutyl-2'-(methanesulphonyl)-4-methylvalerohydrazide, (E)-2(R)-[1(S)-(hydroxycarbamoyl)-4-phenyl-3-butenyl]-2'-(methanesulphonyl)-4-methyl-2'-phenylvalerohydrazide, (E)-2(R)-[1(S)-(hydroxycarbamoyl)-4-phenyl-3-butenyl]-2'-(methanesulphonyl)-4-methyl-2'-[2(S)-methylbutyl]valerohydrazide, (E)-2(R)-[1(S)-(hydroxycarbamoyl)-4-phenyl-3-butenyl]-2'-(methanesulphonyl)-4-methyl-2'-(2-methylallyl)valerohydrazide, and methyl (E)-3-[2(R)-[1(S)-(hydroxycarbamoyl)-4-phenyl-3-butenyl]-4-methylvaleryl]-2-isobutylcarbazate.

22. Compounds of the general formula:

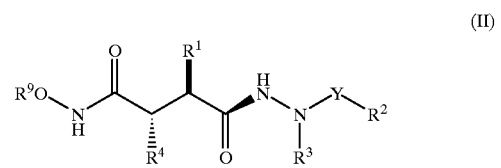

(II)

wherein Y, $R^1$, $R^2$, $R^3$ and $R^4$ have the significance given of claim 1 and $R^9$ is a protecting group.

23. Compounds of claim 22, wherein $R^9$ is tetrahydropyranyl, 4-methoxybenzyl, benzyl or tri(lower alkyl)silyl.

24. A compound of claim 23 wherein $R^9$ is tert-butyldimethylsilyl.

25. Carboxylic acids of the general formula:

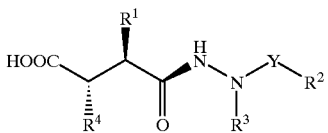
(IX)

wherein Y, $R^1$, $R^2$, $R^3$ and $R^4$ have the significance given in claim 1.

26. A process for the manufacture of the compounds of formula (I) which process comprises deprotecting a compound of the general formula:

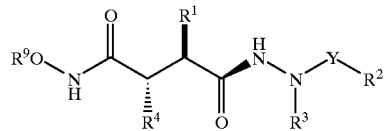
(II)

wherein Y, $R^1$, $R^2$, $R^3$ and $R^4$ have the significance given in claim 1 and $R^9$ is a protecting group, and, if desired, converting a compound of formula I obtained into a pharmaceutically acceptable salt.

27. A pharmaceutical composition which comprises a compound of claim 1 and a therapeutically inert carrier material.

28. A method of treating inflammation, fever, haemorrhage, sepsis, rheumatoid arthritis, osteoarthritis, multiple sclerosis or psoriasis which comprises providing to a patient an amount of the compound of formula I effective to alleviate the inflammation, fever, haemorrhage, sepsis, rheumatoid arthritis, osteoarthritis, multiple sclerosis or psoriasis.

* * * * *